(12) United States Patent
Inagaki et al.

(10) Patent No.: US 9,050,453 B2
(45) Date of Patent: Jun. 9, 2015

(54) ELECTROSTIMULATION SYSTEM, AND ELECTROSTIMULATION ELECTRODE ASSEMBLY AND BIOLOGICAL IMPLANTABLE ELECTRODE THEREFORE

(71) Applicants: National Cerebral and Cardiovascular Center, Osaka (JP); OLYMPUS CORPORATION, Tokyo (JP)

(72) Inventors: Masashi Inagaki, Osaka (JP); Hiroyuki Imabayashi, Tokyo (JP); Takeshi Arai, Tokyo (JP)

(73) Assignees: National Cerebral and Cardiovascular Center, Osaka (JP); OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/624,347

(22) Filed: Sep. 21, 2012

(65) Prior Publication Data

US 2013/0110208 A1    May 2, 2013

Related U.S. Application Data

(63) Continuation-in-part of application No. 13/048,287, filed on Mar. 15, 2011, now abandoned.

(30) Foreign Application Priority Data

Mar. 19, 2010   (JP) ................ P2010-064646
Mar. 19, 2010   (JP) ................ P2010-064648
Mar. 26, 2010   (JP) ................ P2010-072586

(51) Int. Cl.
*A61N 1/05*    (2006.01)
*A61N 1/36*    (2006.01)
(Continued)

(52) U.S. Cl.
CPC ................ *A61N 1/05* (2013.01); *A61N 1/0551* (2013.01); *A61N 1/0558* (2013.01); *A61N 1/056* (2013.01); *A61N 1/36114* (2013.01); *A61B 5/042* (2013.01); *A61B 5/4836* (2013.01)

(58) Field of Classification Search
CPC ...... A61B 17/12109; A61B 17/1214; A61B 18/1492; A61B 2017/00243; A61B 2017/003; A61B 2017/0034; A61B 2017/00358; A61B 2017/1205; A61B 2017/2929; A61B 2018/00214; A61B 2018/144; A61L 2300/41; A61L 31/16; A61M 1/1053; A61M 1/1068; A61M 1/127; A61M 2001/1055; A61M 2001/122; A61M 2025/0681; A61M 2025/09083; A61M 2039/0633; A61M 2039/0646; A61M 2039/242; A61M 2039/2426; A61M 2039/2433; A61M 2205/3515; A61M 25/0017
See application file for complete search history.

(56) References Cited

U.S. PATENT DOCUMENTS 4,357,946 A   11/1982   Dutcher et al.
4,424,818 A   1/1984    Doring et al.
(Continued)

FOREIGN PATENT DOCUMENTS

JP    2003-230635 A    8/2003
JP    2004-173790      6/2004
(Continued)

OTHER PUBLICATIONS

U.S. Office Action dated Nov. 14, 2012 received in related U.S. Appl. No. 13/048,287.
(Continued)

*Primary Examiner* — Brian T Gedeon
*Assistant Examiner* — Ankit Tejani
(74) *Attorney, Agent, or Firm* — Scully, Scott, Murphy & Presser, P.C.

(57) ABSTRACT

An electrostimulation system includes a connector connected to an electrostimulation device, a conducting wire pair electrically connected to the connector, an electrical stimulation lead having a sheathing body configured to insulate the conducting wire pair and installed to be inserted into the vein, an electrical stimulus block portion installed at a leading end side of the electrical stimulation lead and having an electrode portion electrically connected to the conducting wire pair and a fixing block configured to bias the electrode portion to the inner wall of the vein, and a rotary member having an engaging groove detachably engaged with the electrical stimulus block portion and configured to rotate the electrical stimulus block portion disposed in the vein about a central axis of the vein disposed in the vein via the engaging groove.

4 Claims, 62 Drawing Sheets

(51) Int. Cl.
  *A61B 5/042* (2006.01)
  *A61B 5/00* (2006.01)

(56) References Cited

U.S. PATENT DOCUMENTS

| | | | |
|---|---|---|---|
| 6,006,122 A | 12/1999 | Smits | |
| 6,876,885 B2 | 4/2005 | Swoyer et al. | |
| 6,966,914 B2 | 11/2005 | Abe | |
| 7,072,720 B2 | 7/2006 | Puskas | |
| 2002/0103522 A1 | 8/2002 | Swoyer et al. | |
| 2005/0251239 A1* | 11/2005 | Wallace et al. | 607/126 |
| 2006/0041244 A1 | 2/2006 | Hohmann et al. | |
| 2006/0111767 A1 | 5/2006 | Olson et al. | |
| 2007/0293923 A1 | 12/2007 | Soltis et al. | |
| 2008/0161894 A1* | 7/2008 | Ben-David et al. | 607/116 |
| 2008/0215008 A1 | 9/2008 | Nance et al. | |
| 2009/0024195 A1* | 1/2009 | Rezai et al. | 607/116 |
| 2009/0069624 A1* | 3/2009 | Rioux | 600/2 |

FOREIGN PATENT DOCUMENTS

| | | |
|---|---|---|
| JP | 2004-173790 A | 6/2004 |
| JP | 2005-058456 | 3/2005 |
| JP | 2005-58456 A | 3/2005 |
| JP | 2007-535984 A | 12/2007 |
| JP | 2008-067978 | 3/2008 |
| JP | 2008-67978 A | 3/2008 |
| JP | 2008-539006 A | 11/2008 |
| WO | 2005/110528 A1 | 11/2005 |
| WO | 2006/116205 A1 | 11/2006 |
| WO | 2008/092246 A1 | 8/2008 |
| WO | 2008/094789 A1 | 8/2008 |

OTHER PUBLICATIONS

U.S. Office Action dated Jun. 19, 2013 received in related U.S. Appl. No. 13/048,287.
Notice of Reasons for Rejection dated Jan. 7, 2014 from related Japanese Application No. 2010-064648, together with an English language translation.
Notice of Reasons for Rejection dated Jan. 7, 2014 from related Japanese Application No. 2010-072586, together with an English language translation.
U.S. Office Action dated Sep. 24, 2013 from related U.S. Appl. No. 13/048,287.
Notice of Reasons for Rejection dated Nov. 26, 2013 from related Japanese Application No. 2010-064646, together with an English language translation.
Notice of Allowance dated Sep. 2, 2014 from related Japanese Application No. 2010-064648, together with an English language translation.

* cited by examiner

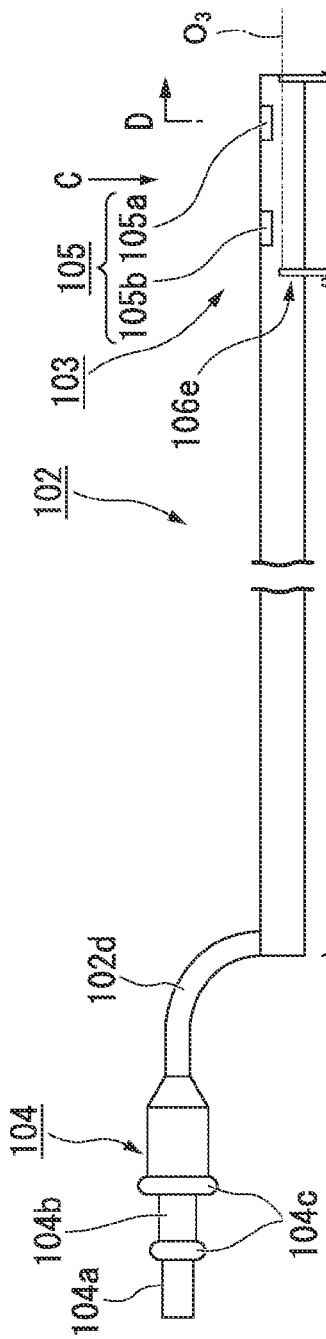
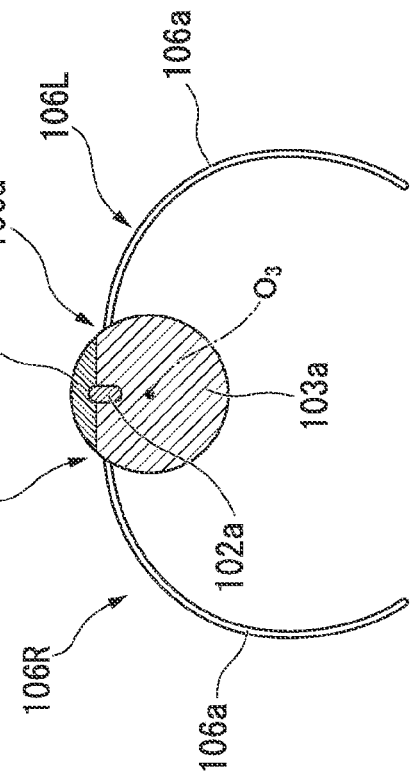
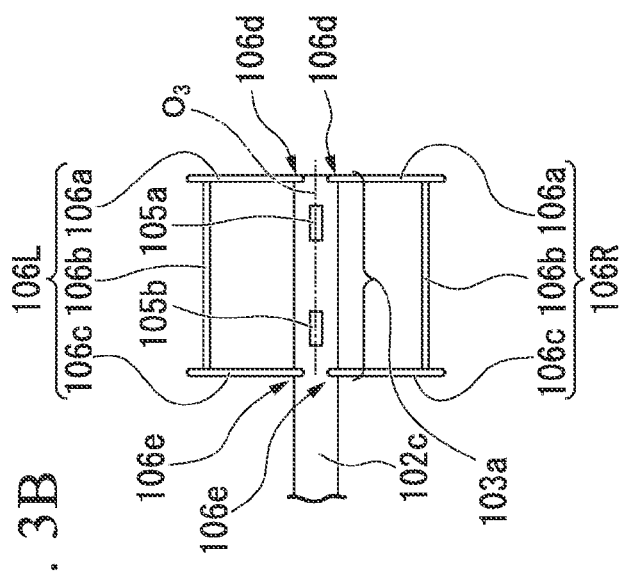
FIG. 3A
FIG. 3B
FIG. 3C

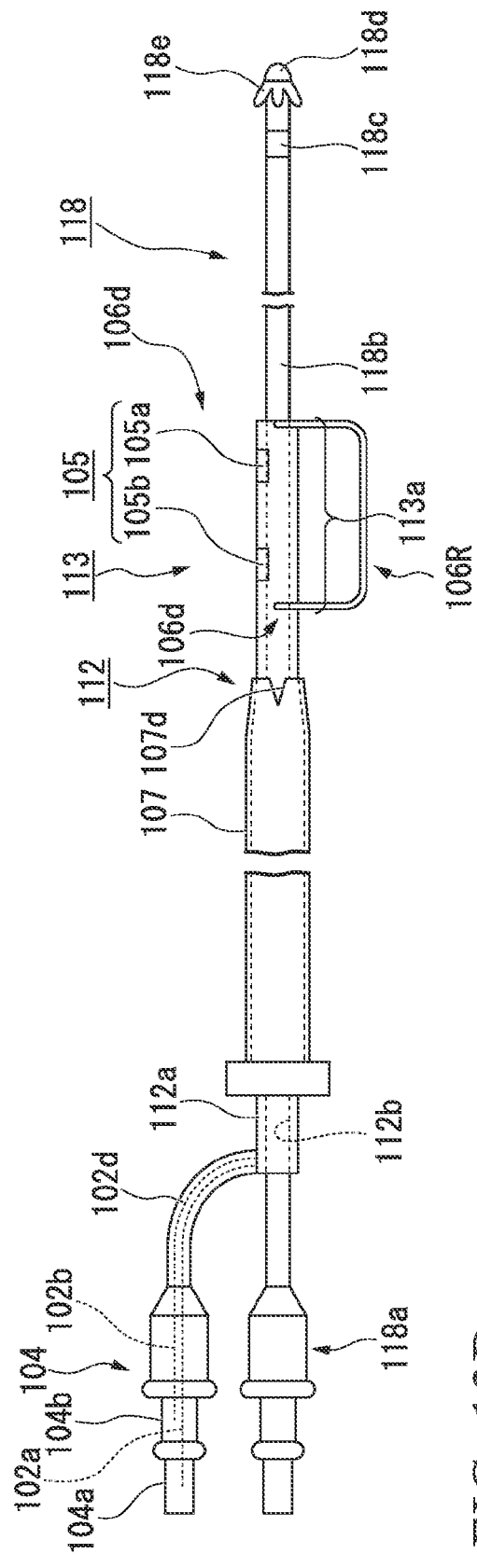
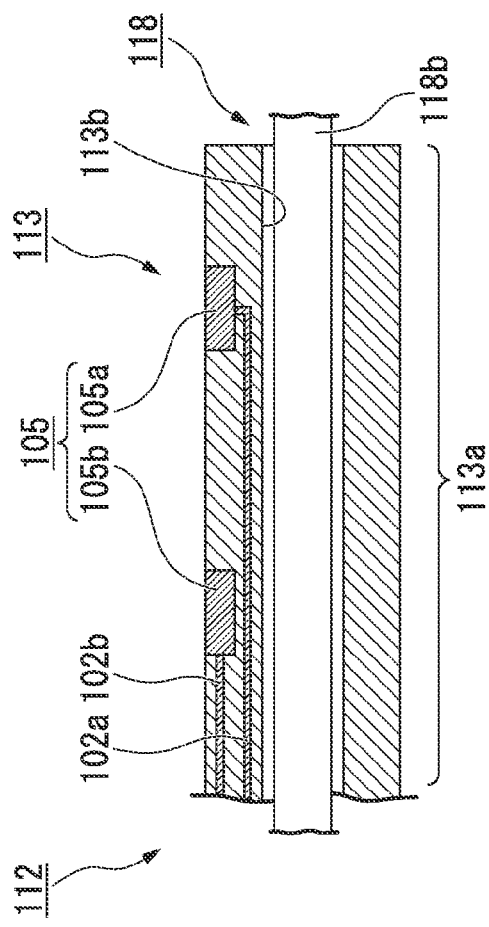
FIG. 13A
FIG. 13B

ELECTROSTIMULATION SYSTEM, AND ELECTROSTIMULATION ELECTRODE ASSEMBLY AND BIOLOGICAL IMPLANTABLE ELECTRODE THEREFORE

Priority is claimed on Japanese Patent Application No. 2010-064646 filed on Mar. 19, 2010, Japanese Patent Application No. 2010-064648 filed on Mar. 19, 2010, and Japanese Patent Application No. 2010-072586 filed on Mar. 26, 2010, and this application is a continuation-in-part application of U.S. patent application Ser. No. 13/048,287 filed on Mar. 15, 2011, the contents of which are incorporated herein by reference.

BACKGROUND OF THE INVENTION

1. Field of the Invention

The present invention relates to an electrostimulation system, and an electrostimulation electrode assembly and a biological implantable electrode therefor. In particular, the present invention relates to an electrostimulation system which applies electrical stimulus to the nervous tissue, an electrostimulation electrode assembly which applies electrical stimulus to the nervous tissue, and a biological implantable electrode which is connected to an electrical stimulus generation device placed in a biological body to apply electrical stimulus to the biological tissue, such as muscles, nerves, or heart, which requires electrical stimulus.

2. Description of Related Art

In the related art, a stimulus generation device is known which applies electrical stimulus for treatment to the nervous tissue or the biological tissue (linear tissue), such as muscles. Examples of the stimulus generation device include a nervous stimulation device, a pain relief device, an epilepsy treatment device, a muscle stimulation device, and the like.

In the stimulus generation device, a conducting wire which transmits electrical stimulus is implanted in the biological body for use so as to bring the conducting wire into close contact with a stimulation target in the biological body.

In general, the conducting wire has at least one electrode portion which applies electrical stimulus to the biological tissue or detects electrical excitation in the biological tissue, an electrical connector which is used for electrical connection to the stimulus generation device, and a lead body which is provided between the electrode portion and the stimulus generation device and transmits electrical stimulus.

For example, Japanese Unexamined Patent Application, First Publication No. 2004-173790 describes an implanted heart treatment device which stimulates the heart when the heart produces bradycardia to increase the heart rate, stimulates the vagus nerve when the heart produces tachycardia or fibrillation to decrease the heart rate. In the heart treatment device, a heart stimulation electrode is arranged inside the myocardium or the atrium, and a nerve stimulation electrode is arranged to be wound around the vagus nerve in the cervical region.

Japanese Unexamined Patent Application, First Publication No. 2008-67978 describes a biological implantable electrode lead which includes an electrode support having at least one arm portion, in which an electrode is formed, the arm portion being loaded to be wound around the biological tissue, such as the cervical vagus nerve.

Heretofore, a device, such as a heart pacemaker, an implantable defibrillation device, a nervous stimulation device, or a deep brain stimulation device, is known which applies electrical stimulus for treatment to the biological tissue, which requires stimulation. The device includes an electrical stimulus generation device which has an internal power supply and an electrical circuit necessary for electrostimulation, an electrode which is loaded in the biological tissue, which requires stimulation, to apply electrical stimulus to the biological tissue, and a conducting wire which transmits electrical information from the stimulus generation device to the electrode.

Of these, the biological implantable electrode placed in the body includes at least one electrode which applies electrical stimulus to the biological tissue, such as the heart, nervous tissue, or muscles, or detects electrical excitation in the biological tissue; a conducting wire sheathing body which has an electrical conductor and a biocompatible insulating sheath connected to the electrode; a connector which electrically connects various electrical stimulus generation devices, such as a heart pacemaker, an implanted defibrillation device, a nervous stimulation device, and a deep brain simulation device, to the conducting wire sheathing body; and the like.

As the biological implantable electrode of the related art, electrodes are known which are described in Japanese Unexamined Patent Application, First Publication Nos. 2008-67978 and 2005-58456. Japanese Unexamined Patent Application, First Publication No. 2008-67978 describes an electrode assembly for nervous stimulation which is implantable into the biological body. In the electrode assembly, an electrode at the tip of a conducting wire sheathing body has an arm portion, and the arm portion is loaded to be wound around the nerve. In the biological implantable electrode described in Japanese Unexamined Patent Application, First Publication No. 2005-58456, a lubricating coated layer is provided in a portion of the surface of an insulating sheath.

SUMMARY OF THE INVENTION

A first aspect of the present invention provides an electrostimulation system. The electrostimulation system includes a sheathed conducting wire member which has a terminal portion to be connected to an electrostimulation device, a conducting wire pair electrically connected to the terminal portion, and a sheathing body insulating the conducting wire pair, and is provided to pass through a vein, an electrostimulation block which is provided on the leading end side of the sheathed conducting wire member, and has an electrode pair electrically connected to the conducting wire pair and an electrode urging member urging the electrode pair toward the inner wall of the vein, and a rotary member which has an engagement portion detachably engaged with the electrostimulation block and rotates the electrostimulation block arranged inside the vein around the center line of the vein through the engagement portion.

According to a second aspect of the present invention, in the electrostimulation system, the electrostimulation block may have a convex portion protruding outside the outer circumference of the sheathed conducting wire member, and the rotary member may be formed in a tubular shape through which the sheathed conducting wire member passes and may have a groove portion provided at the leading end thereof to be engageable with the convex portion in a circumferential direction of rotation.

In the electrostimulation system, the electrostimulation block may have a groove portion formed inside the outer circumference of the sheathed conducting wire member, and the rotary member may be formed in a shaft shape or tubular shape which is passable through the sheathed conducting wire member and may have a convex portion provided to be engageable with the groove portion in a circumferential direction of rotation.

According to a third aspect of the present invention, in the electrostimulation system, the sheathed conducting wire member and the electrostimulation block may have a hollow structure in which hollow portions communicate with each other, a pacing lead which is placed inside a heart may be put in the hollow portions, and the sheathed conducting wire member and the electrostimulation block may be provided rotatably at least in a circumferential direction with respect to the outer circumferential surface of the pacing lead.

The electrode urging member may include an elastic member which has an arc portion having a diameter greater than the inner diameter of the vein in a natural state.

The elastic member may be constituted by a superelastic wire having shape reversibility.

According to a fourth aspect of the present invention, the electrode urging member may be constituted by a cylindrical balloon whose outer diameter is enlargeable and reducible through fluid pressure.

A fifth aspect of the present invention provides an electrostimulation electrode assembly. The electrostimulation electrode assembly includes an electrode which is inserted into a vein and applies electrical stimulus through the inner wall of the vein, an insulating support which supports the electrode in a state where a portion of the electrode is exposed to the surface as an exposed electrode surface, a conducting wire member which is electrically connected to the electrode in the support and extends outside the support, a sheathing member which has a linear shape to pass through the vein and one end portion of which is connected to the support, ensuring that the conducting wire member extending from the support passes therethrough in an insulation state and guided to the other end portion thereof, a terminal portion which is electrically connected to the conducting wire member guided to the other end portion of the sheathing member and provided to be connectable to a stimulus generation device generating electrical stimulus, and an electrode urging member which is connected to the support and urges the electrode exposed from the support toward the inner wall of the vein.

The support may be provided to have a shape so as to cover the entire electrode when viewed from the rear side of the exposed electrode surface.

The support may be provided so as to extend from the one end portion of the sheathing member along the axial direction of the sheathing member, and the electrode urging member may be connected to the support at a position with the exposed electrode surface sandwiched therebetween in the extension direction of the support.

The electrode urging member may include an elastic body which is fixed to the lateral surface of the support at a position with the exposed electrode surface sandwiched therebetween when viewed from the extension direction of the support, extends to both lateral sides of the support in an arc shape such that a direction in which the exposed electrode surface is formed is made convex when viewed from the extension direction of the support, and has a curved portion being curvable along the circumferential direction of the inner wall of the vein.

The elastic body may be constituted by a plurality of linear curved bodies which are arranged to be separated in the extension direction of the support, and a linear leading end connection portion may be provided to connect the leading ends of the plurality of linear curved bodies in the extension direction of the support.

The leading end connection portion may be bent so as to protrude outwardly in the radial direction of curvature from a curved surface in which the plurality of curved bodies are arrayed.

The curved portion may have a U-shaped bent shape in an intermediate portion thereof.

The electrode urging member may have an elastic body which is fixed to the lateral surface of the sheathing member at a position in the one end portion of the sheathing member with the exposed electrode surface sandwiched therebetween when viewed from the axial direction of the sheathing member, extends to both lateral sides of the sheathing member in an arc shape such that a direction in which the exposed electrode surface is formed is made convex when viewed from the axial direction of the sheathing member, and has a curved portion being curvable along the circumferential direction of the inner wall of the vein. The support may be provided on the electrode urging member.

According to a sixth aspect of the present invention, the elastic body may be made of a conductive material and may double as the conducting wire member in the support.

A seventh aspect of the present invention provides a biological implantable electrode. The biological implantable electrode includes an electrode portion which applies electrical stimulus to a biological tissue, an elongated conductive wire sheathing body which connects the electrode portion and the electrical stimulus generation device, and an electrode support which supports the electrode portion in the biological body. The electrode support is reversibly deformable to a first shape suitable for supporting the electrode portion in the biological body and a second shape suitable for introducing and removing the electrode portion with respect to the biological body.

According to an eighth aspect of the present invention, the biological implantable electrode may further include a deformation mechanism which deforms the electrode support to the second shape. The electrode support may be maintained in the first shape in a natural state where external force is not applied.

The deformation mechanism may have a tubular member through which the conducting wire sheathing body passes, and the electrode support may be accommodated inside the tubular member to be deformed to the second shape.

A ninth aspect of the present invention provides a method of adjusting an electrostimulation system. The method includes an electrostimulation block insertion step of passing an electrostimulation block formed at the leading end of a sheathed conducting wire member through a vein and urges an electrode the pair of electrostimulation block toward the inner wall of the vein, an electrode alignment step of rotating and adjusting the electrostimulation block on the basis of the behavior of an electrostimulation pulse of a nervous tissue around the vein, and an electrostimulation step of applying an electrostimulation pulse to the nervous tissue around the vein.

The method according to the ninth aspect of the present invention may further include an electrostimulation block ejection step of ejecting the electrostimulation block from the vein after a desired electrostimulation pulse is applied.

A tenth aspect of the present invention provides a method of deforming a biological implantable electrode. The method includes a second shape deformation step of deforming an electrode support so as to pass through a vein, a first shape deformation step of deforming the electrode support for support in the vein, and a second shape re-deformation step of deforming the electrode support to the second shape again so as to be removed from the vein.

An eleventh aspect of the present invention provides a method of placing an electrostimulation system. The method includes an electrode unit insertion step of inserting an electrode unit into a vein, an electrode unit disposition step of disposing the electrode unit in a superior vena cava in the vicinity of a vagus nerve, an electrode unit biasing step of biasing a stimulation electrode included in the electrode unit in a direction of the vagus nerve, and an electrical stimulation step of applying electrical stimulus energy to the vagus nerve.

A twelfth of the present invention provides a method of placing the electrostimulation system. The method further includes a thrombus formation prevention step after the electrode unit disposition step.

The thrombus formation prevention step may be an anticoagulant agent discharge step of discharging an anticoagulant agent from a liquid feed tube opening formed in the electrode unit.

A thirteenth aspect of the present invention provides a method of placing the electrostimulation system. The method further includes an electrode ejection unit ejection step of ejecting an electrode unit from a vein after application of desired electrical stimulus energy.

BRIEF DESCRIPTION OF THE DRAWINGS

FIG. 3A is a schematic front view of a sheathed conducting wire member and an electrostimulation block which are used in the electrostimulation system according to the first embodiment of the present invention.

FIG. 3B is a diagram when viewed from a direction indicated by an arrow C of FIG. 3A.

FIG. 3C is a sectional view taken along the D-D of FIG. 3A.

FIG. 13A is a schematic front view of the electrostimulation system according to the second embodiment of the present invention.

FIG. 13B is a sectional view taken along the axial direction of an electrostimulation block which is used in the electrostimulation system according to the second embodiment of the present invention.

DETAILED DESCRIPTION OF THE INVENTION

Figure 1A:
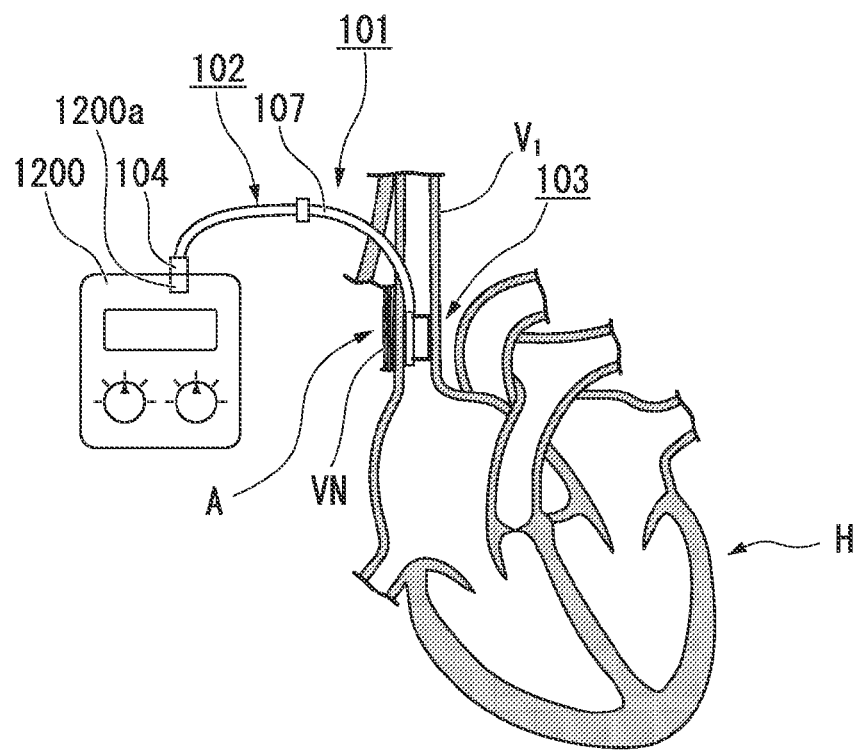
FIG. 1A is a schematic sectional view showing a state when an electrostimulation system according to a first embodiment of the present invention is loaded in a superior vena cava.

Hereinafter, embodiments of the present invention will be described with reference to the accompanying drawings. In all the drawings, even when embodiments are different, the same or similar members are represented by the same reference numerals, and common description will be omitted.

[First Embodiment]

An electrostimulation system according to a first embodiment of the present invention will be described.

Figure 1B:
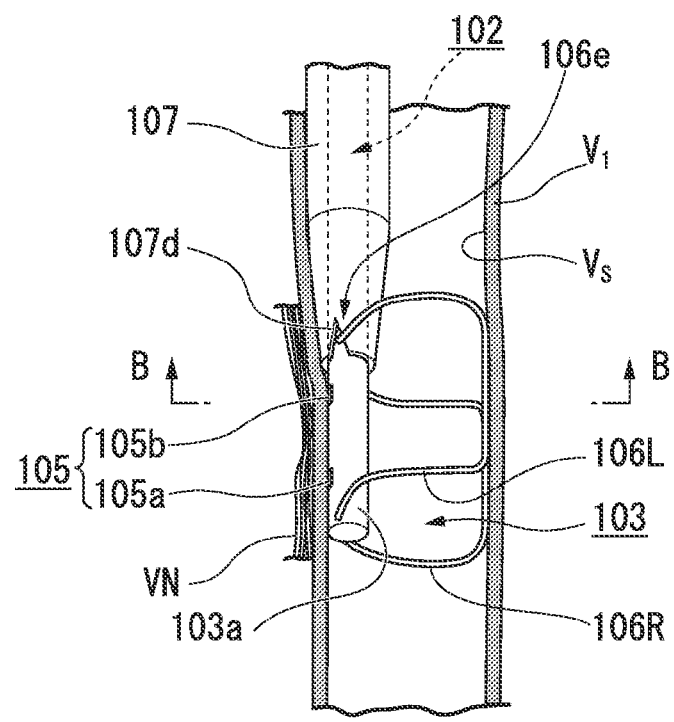
FIG. 1B is a schematic perspective view of an A portion of FIG. 1A on a magnified scale.
Figure 2:
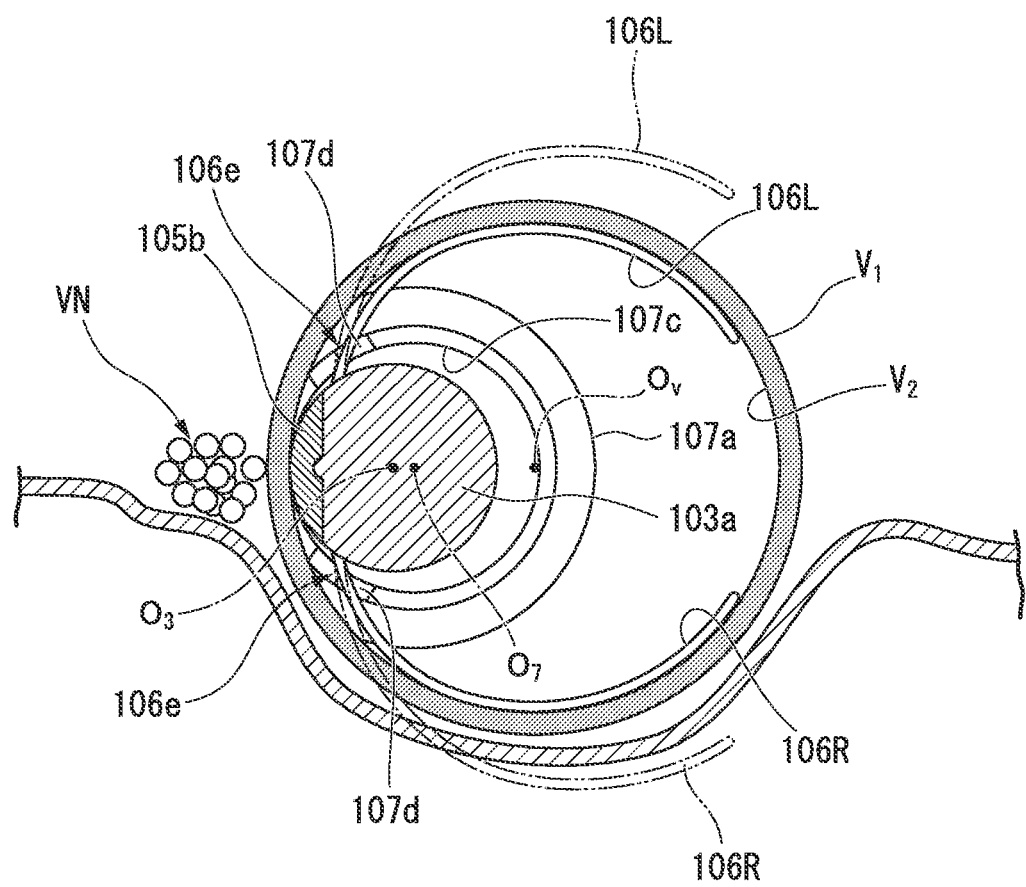
FIG. 2 is a sectional view taken along the line B-B of FIG. 1B.
Figure 4:
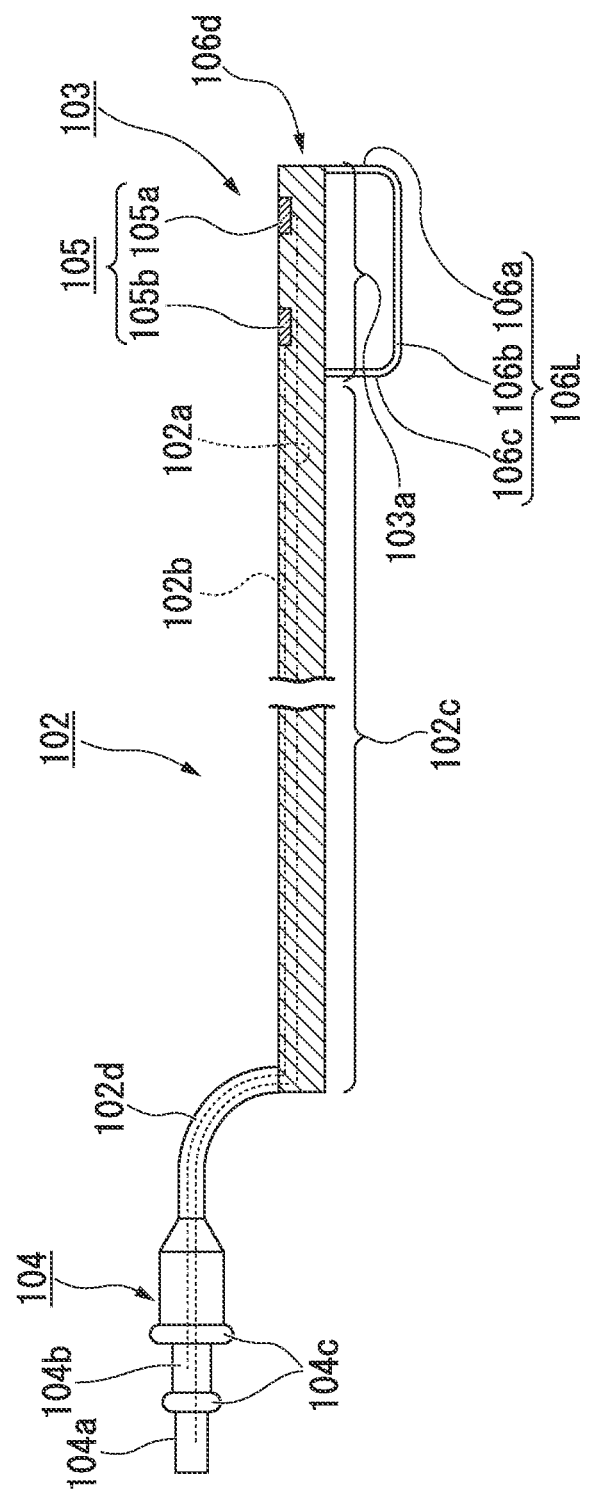
FIG. 4 is a partial sectional view taken along the axial direction of the sheathed conducting wire member and the electrostimulation block which are used in the electrostimulation system according to the first embodiment of the present invention.
Figure 5A:
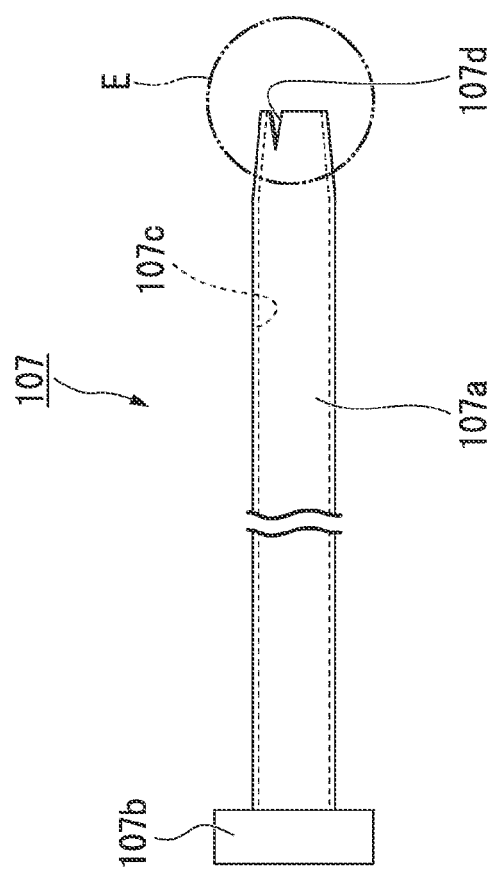
FIG. 5A is a schematic front view of a rotary member which is used in the electrostimulation system according to the first embodiment of the present invention.
Figure 5B:
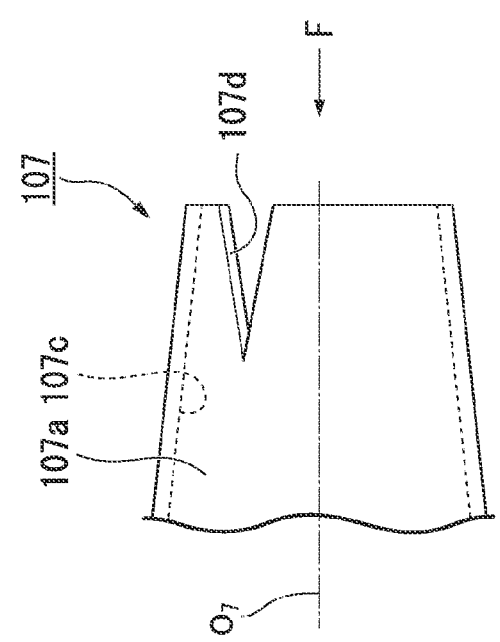
FIG. 5B is an enlarged view of an E portion of FIG. 5A.
Figure 5C:
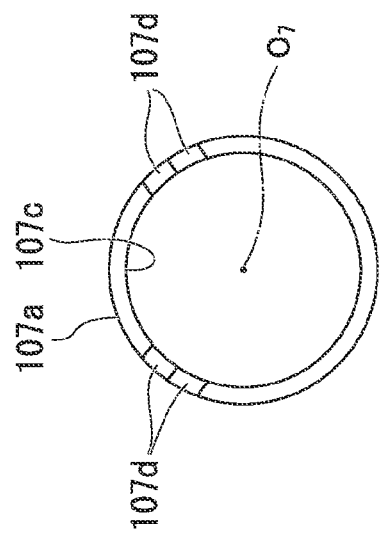
FIG. 5C is a diagram when viewed from a direction indicated by an arrow F of FIG. 5B.

FIG. 1A is a schematic sectional view showing a state when an electrostimulation system according to a first embodiment of the present invention is loaded in a superior vena cava. FIG. 1B is a schematic perspective view of an A portion of FIG. 1A on a magnified scale. FIG. 2 is a sectional view taken along the line B-B of FIG. 1B. FIG. 3A is a schematic front view of a sheathed conducting wire member and an electrostimulation block which are used in the electrostimulation system according to the first embodiment of the present invention. FIGS. 3B and 3C are respectively a diagram when viewed from a direction indicated by an arrow C of 3A and a sectional view taken along the line D-D of FIG. 3A. FIG. 4 is a partial sectional view taken along the axial direction of the sheathed conducting wire member and the electrostimulation block which are used in the electrostimulation system according to the first embodiment of the present invention. FIG. 5A is a schematic front view of a rotary member which is used in the electrostimulation system according to the first embodiment of the present invention. FIG. 5B is an enlarged view of an E portion of FIG. 5A. FIG. 5C is a diagram when viewed from a direction indicated by an arrow F of FIG. 5B.

The drawings are schematic views, thus the shape or dimension is magnified (the same is applied to the following description).

As shown in FIGS. 1A and 1B, an electrostimulation system 101 of this embodiment includes an electrostimulation lead 102 (sheathed conducting wire member), an electrostimulation block portion 103 (electrostimulation block), and a rotary member 107.

The electrostimulation system 101 includes the electrostimulation lead 102 which is connected to an electrostimulation device 1200 implanted in or provided outside a biological body, and the electrostimulation block portion 103 which is provided at the leading end of the electrostimulation lead 102. For example, the electrostimulation system 101 is configured such that the electrostimulation block portion 103 is inserted into a vein, such as a superior vena cava $V_1$, along with the electrostimulation lead 102, and electrically stimulates a nervous tissue, for example, a vagus nerve VN, outside the vein from the electrostimulation block portion 103.

In recent years, in the field of a treatment of cardiac failure, it becomes clear that, when chronic cardiac failure is exacerbated, the prognosis becomes worse. It is known that a nervous stimulation device is used to apply electronic intervention directly to an automatic nerve, thereby correcting circulation dysregulation.

The electrostimulation system 101 of the embodiment can be particularly appropriate for a treatment in which electrical stimulus is applied to a nervous tissue near a heart H.

Hereinafter, as shown in FIGS. 1A, 1B, and 2, an example will be described where the electrostimulation block portion 103 of the electrostimulation system 101 is inserted from the superior vena cava $V_1$ and placed in the inner wall portion of a vein near the vagus nerve VN, and applies electrical stimulus to the vagus nerve VN.

Although the sectional shape of a vein inner wall $V_s$ of the superior vena cava $V_1$ is different from a geometrically true circle, for convenience, description will be provided assuming a circular shape because the vein inner wall $V_s$ is maintained in a shape capable of being approximated to a circular shape due to a blood pressure. That is, hereinafter, when the vein inner wall $V_s$ is regarded as a circle, this indicates an approximate circle, and an inner diameter indicates the diameter of the approximate circle.

Hereinafter, in expressing the positional relationship of a member to be inserted into a vein along the axial direction, if there is no room for misunderstanding, the leading end side in the insertion direction may be simply referred to as the leading end side, and the opposite side to the leading end side may be referred to as the base end side. The terms leading end, leading end portion, and the like may be used to mean the same positional relationship.

The electrostimulation system 101 can apply electrical stimulus to any nervous tissue insofar as the nervous tissue is near the vein, and is not limited to the purpose for an electrostimulation treatment of the vagus nerve VN.

The electrostimulation device 1200 which is connected to the electrostimulation system 101 uses a battery as a power source and generates an electrostimulation pulse set in advance. In particular, when the electrostimulation device 1200 is provided outside the body, a liquid crystal screen for set value display may be provided. Wireless communication with an exclusive-use controller (not shown) may be performed to remotely change the setting of the electrostimulation conditions or acquire the operation history.

The electrostimulation conditions of the electrostimulation device 1200 include the magnitude of the electrostimulation pulse voltage, frequency, pulse width, stimulation end time, stimulation start time, stimulation duration time, electrostimulation stoppage, and the like.

The schematic configuration of the electrostimulation lead 102 is as shown in FIGS. 3A, 3B, 3C, and 4. That is, the electrostimulation lead 102 includes a connector 104 (terminal portion), a sheathing tube 102d, a pair of conducting wires 102a and 102b, and a sheathing member 102c (sheathing body). As a whole, the electrostimulation lead 102 is an elongated linear body.

The connector 104 is a terminal portion which is connected to a connection terminal 1200a (see FIG. 1A) provided on the surface of the electrostimulation device 1200. The connector 104 is provided on the base end side in the insertion direction of the electrostimulation lead 102 into the vein.

As the connector type of the connector 104, an appropriate connector type according to the shape of the connection terminal 1200a of the electrostimulation device 1200 may be used.

In this embodiment, an IS1 connector is used which is used when the electrostimulation device 1200 is provided inside the body. That is, the connector 104 includes a connector pin 104a for a negative electrode and a connector pin 104b for a positive electrode, and a pair of rubber rings 104c. The rubber rings 104c insulate the connector pin 104a for a negative electrode and a connector pin 104b for a positive electrode and also remain watertight at the time of connection to the connection terminal 1200b.

The connector pin 104a for a negative electrode and the connector pin 104b for a positive electrode are both made of stainless steel. The rubber rings 104c are formed of silicone rubber having biocompatibility.

As another connector type of the connector 104, a waterproof connector may be used which is used when the electrostimulation device 1200 is provided outside the body.

The conducting wire 102a is a linear or coil-like electrical conductor which electrically connects the connector pin 104a for a negative electrode and a negative electrode 105a (described below) of the electrostimulation block portion 103. The shape or material of the conducting wire 102a is not particularly limited insofar as the conducting wire 102a is resistant to bending in the vein into which the electrostimulation lead 102 is inserted. In this embodiment, for example, a twisted wire made of nickel-cobalt alloy is used.

The conducing wire 102b is a linear or coil-like electrical conductor which electrically connects the connector pin 104b for a positive electrode and a positive electrode 105b (described below) of the electrostimulation block portion 103. With regard to the conducting wire 102b, the same shape and material as the conducting wire 102a may be used. In this embodiment, for example, a twisted wire made of nickel-cobalt alloy is used.

As shown in FIG. 4, the conducting wires 102a and 102b which are respectively connected to the connector pin 104a for a negative electrode and the connector pin 104b for a positive electrode pass through the sheathing tube 102d which sheaths the conducting wires 102a and 102b in a state of being insulated from each other, are guided to the base end portion of the sheathing member 102c to which the sheathing tube 102d is connected, and pass through the sheathing member 102c.

As the material of the sheathing tube 102d, for example, polyurethane resin may be used.

As shown in FIGS. 3A and 4, the sheathing member 102c is a solid linear member through which the conducting wires 102a and 102b are passed from the base end side, to which the sheathing tube 102d is connected, and is wired toward the negative electrode 105a and the positive electrode 105b which sheathes the conducting wires 102a and 102b so as not to come into contact with each other and not to be exposed to the outside.

The outer shape in the sectional shape of the sheathing member 102c is formed by a smooth curved surface which comes into smooth contact with the inner wall of the vein, such as the superior vena cava $V_1$, and is rotatable in the circumferential direction. For example, a circular shape, an elliptical shape, an oval shape, or an approximate shape may be used.

In this embodiment, the sectional shape of the sheathing member 102c is a circular shape having an outer diameter sufficiently smaller than the inner wall of the superior vena cava $V_1$ so as not to interfere with the blood flow at the time of insertion into the superior vena cava $V_1$. As described below, the sheathing member 102c has an outer diameter so as to pass through the rotary member 107 which has an outer diameter so as to pass through the superior vena cava $V_1$. For example, it is preferable that the diameter of the sheathing member 102c is set in a range of φ1 mm to φ2.5 mm. In this embodiment, the diameter of the sheathing member 102c is φ2 mm.

The sheathing member 102c is made of a material having electrical insulation, flexibility, and biocompatibility in the vein. As the material of the sheathing member 102c, in this embodiment, a polyurethane resin is used.

The outer surface of the sheathing member 102c may be subjected to thrombus prevention coating.

The electrostimulation block portion 103 includes a columnar support 103a which is provided coaxially with the sheathing member 102c connected to the leading end side of the sheathing member 102c, an electrode portion 105 which is supported by the support 103a, and fixing hooks 106R and 106L (electrode urging member) which are attached to the outer circumferential surface of the support 103a to urge the electrode portion 105 toward the vein inner wall $V_s$, such as the superior vena cava $V_1$.

The support 103a is provided on the leading end side of the sheathing member 102c, and supports the electrode portion 105 and the fixing hooks 106R and 106L in the lateral surface. The support 103a has passes therethrough the conducting wires 102a and 102b extending from the sheathing member 102c in a state of being insulated from each other and guides the conducting wires 102a and 102b to the electrode portion 105.

In this embodiment, the support 103a has a columnar outer shape having the same diameter as the sheathing member 102c, and is molded as a single body with the sheathing member 102c by using the same insulating material as the sheathing member 102c.

The electrode portion 105 is constituted by an electrode the pair of negative electrode 105a which is electrically connected to the conducting wire 102a inside the support 103a and the positive electrode 105b which is electrically connected to the conducting wire 102b inside the support 103a.

As shown in FIGS. 3A and 3B, the negative electrode 105a and the positive electrode 105b are such that a rectangular electrode surface in side view is exposed from the lateral surface of the support 103a. With regard to the arrangement position on the lateral surface of the support 103a, the negative electrode 105a and the positive electrode 105b are arranged in a column with a space in the axial direction of the support 103a. In this embodiment, the negative electrode 105a and the positive electrode 105b are arranged in that order from the leading end side of the support 103a. The length of each electrode surface of the negative electrode 105a and the positive electrode 105b is, for example, 2 mm, and the gap (separation interval) in the axial direction between the negative electrode 105a and positive electrode 105b is set to, for example, 5 mm.

As shown in FIG. 3C, the shape of the negative electrode 105a in the cross-section perpendicular to a central axis $O_3$ of the support 103a is an arch shape in which the exposed electrode surface substantially follows the outer shape of the support 103a or slightly protrudes. That is, the exposed electrode surface of the negative electrode 105a is constituted by a partial cylindrical surface.

The internal shape of the support 103a is not particularly limited insofar as the support can be fastened to the support 103a. For example, in FIG. 3C, the internal shape is substantially a flat plate shape, and the sectional shape including the electrode surface is a D shape. The internal shape may be a V shape which is made convex toward the central axis $O_3$ of the support 103a, a U shape, or the like. A reverse T shape or an arrow shape protruding downward in the drawing may be provided or an external screw shape or a multi-ring shape may be provided in the outer circumferential portion such that the withdrawal resistance outwardly in the radial direction with respect to the support 103a increases.

The positive electrode 105b has the same shape as the negative electrode 105a.

The length (the exposed length in the circumferential direction) of an arc in each electrode surface of the negative electrode 105a and the positive electrode 105b is set such that electrical stimulus can be efficiently applied to the nervous tissue outward in the radial direction through the vein inner wall in close contact therewith when each electrode is pressed against the superior vena cava $V_1$.

While depending on the ratio between the radius of curvature of the vein inner wall $V_s$ and the radius of the arc of the electrode surface, for example, if the center angle (hereinafter, referred to as an electrode exposure angle) of the arc of the electrode surface is greater than 180°, electricity is likely to leak to another peripheral tissue. For this reason, a semicircular shape or a minor arcuate shape is preferably used such that the electrode surface can be directed outward in the radial direction of the vein.

In this embodiment, because the vagus nerve VN around the superior vena cava $V_1$ is stimulated, there is possibility that electricity may leak and stimulate a nearby phrenic nerve or the like.

In the case of a major arc or a near-circular minor arc, the negative electrode 105a and the positive electrode 105b easily come into contact with blood. For this reason, electrical energy flows through blood, and electrical energy which is applied to a vascular tissue facing the vagus nerve VN decreases, making it difficult to stimulate the vagus nerve VN.

For this reason, in this embodiment, it is preferable that the electrode exposure angle is equal to or smaller than 120°.

If the electrode exposure angle is excessively small, the range in which electrical stimulus is applied in the circumferential direction is excessively narrowed, so a high voltage should be applied for electrostimulation.

For this reason, it is preferable that the electrode exposure angle is equal to or greater than 30°.

In this embodiment, for example, when the outer radius of the support 103a is 1 mm, the electrode surface of the negative electrode 105a has a radius of 1 mm and an electrode exposure angle of 90°.

In this embodiment, each of the fixing hooks 106R and 106L is formed by bending a linear elastic member in a U shape (angulated U shape) and has arcuate arm portions 106a and 106c and a hook leading end portion 106b.

As shown in FIGS. 3B and 3C, the fixing hooks 106R and 106L are formed and arranged so as to be plane-symmetric to the plane including the center line in the axial direction, which is common to the electrode surfaces of the negative electrode 105a and the positive electrode 105b arranged in the axial direction of the support 103a, and the central axis $O_3$ of the support 103a. The fixing hook 106R is located on the right when viewed from the base end side of the support 103a to the leading end side in a state where the electrode surface of the electrode portion 105 turns upward, and the fixing hook 106L is located on the left side in the same manner.

As the material of the fixing hooks 106R and 106L, an appropriate elastic material may be used which can press the vein inner wall $V_s$ by elastic restoring force.

More preferably, a shape-restorable elastic material is used which has flexibility so as to be a little foldable when inserted into the vein and can urge the inner wall of the vein. Examples of such a material include a superelastic alloy which has shape-reversibility so as to be easily elastically deformed by external force and to return to the state before deformation if external force is removed, for example, a nickel-titanium-based alloy. In this embodiment, as an example, a member is used which is formed by molding a superelastic wire having a diameter $\phi 0.3$ mm made of a nickel-titanium-based alloy in a U shape.

Though not particularly shown, the fixing hooks 106R and 106L are configured such that the outer circumferential surface of the superelastic wire is covered with polyurethane tube coating or fluorine resin-based coating. For this reason, the superelastic wire does not come into direct contact with blood in the vein or the vein inner wall $V_s$. Since polyurethane or fluorine resin has small frictional resistance against the vein inner wall $V_s$ the polyurethane tube coating or fluorine resin-based coating allow smooth sliding along the vein inner wall $V_s$.

Similarly to the sheathing member 102c, the tube is preferably subjected to thrombus prevention coating.

Hereinafter, unless specially noted, description will be provided assuming that the shapes of the arcuate arm portions 106a and 106c and the hook leading end portion 106b which are common to the fixing hooks 106R and 106L are in the natural state where no external force is applied.

The arcuate arm portion 106a is configured such that a fixed shaft end 106d (convex portion) protrudes from the leading end side compared to the negative electrode 105a in the lateral surface of the support 103a. The arcuate arm portion 106a is constituted by a linear body which protrudes obliquely from the fixed shaft end 106d outwardly in the radial direction is curved toward the opposite side to the electrode surface of the negative electrode 105a so as to substantially have an arc shape when viewed from the axial direction.

The position in the circumferential direction of the fixed shaft end 106d is set to a position distant from the end portion in the circumferential direction of the negative electrode 105a outwardly in the circumferential direction. For this reason, as shown in FIG. 3C, when the electrode surface of the negative electrode 105a turns upward, the fixed shaft end 106d protrudes from the lower lateral surface compared to the electrode surface of the negative electrode 105a.

As indicated by a two-dot-chain line of FIG. 2, the radius of curvature of the arc shape of the arcuate arm portion 106a is set to be greater than the radius of the vein inner wall $V_s$ of the superior vena cava $V_1$.

The length of the arcuate arm portion 106a is equal to or greater than ¼ of the circumferential length of the vein inner wall $V_s$ at a position in the superior vena cava $V_1$ where the electrostimulation block portion 103 is provided.

The arcuate arm portion 106c is configured such that a fixed shaft end 106e protrudes from the base end side compared to the positive electrode 105b in the lateral surface of the support 103a. The arcuate arm portion 106c is constituted by a linear body which protrudes obliquely from the fixed shaft end 106e outward in the radial direction in the same direction as the arcuate arm portion 106a and is curved toward the opposite side to the electrode surface of the positive electrode 105b so as to substantially have an arc shape when viewed from the axial direction.

The position in the circumferential direction of the fixed shaft end 106e and the curved shaped of the arcuate arm portion 106c are set so as to overlap the arcuate arm portion 106a when viewed from the axial direction of the support 103a.

For this reason, similarly to the fixed shaft end 106d, when the electrode surface of the positive electrode 105b turn upward, the position in the circumferential direction of the fixed shaft end 106e is set such that the fixed shaft end 106e protrudes from the lower lateral surface compared to the electrode surface of the positive electrode 105b. FIG. 2 shows a state where the positional relationship is rotated left by 90°.

As shown in FIGS. 3A and 3B, the hook leading end portion 106b is a linear body which extends in the axial direction of the support 103a while connecting the leading ends in the protrusion direction of the arcuate arm portions 106a and 106c. Both end portions of the hook leading end portion 106b and the leading ends in the protrusion direction of the arcuate arm portions 106a and 106c form corner portions having an R shape. Thus, the fixing hooks 106R and 106L can come into smooth contact with and slide along the vein inner wall $V_s$.

The fixing hooks 106R and 106L are respectively constituted by the arcuate arm portions 106a and 106c and the hook leading end portion 106b so as to be arrayed on the cylindrical surface having a diameter greater than the vein inner wall $V_s$ extending laterally from the lateral surface of the support 103a and to have a U shape with the fixed shaft ends 106d and 106e as an opening end.

Thus, when the electrostimulation block portion 103 is inserted into the superior vena cava $V_1$, as shown in FIG. 2, the fixing hooks 106R and 106L can be elastically deformed along the vein inner wall $V_s$ and can urge the vein inner wall $V_s$ outward in the radial direction in accordance with the deformation amount.

In this embodiment, the sheathing member 102c and the support 103a have the same outer diameter, such that the fixed shaft end 106e constitutes a convex portion which protrudes to a position outside the outer circumference of the sheathing member 102c.

As described above, the electrostimulation block portion 103 is provided on the leading end side of the electrostimulation lead 102. The electrostimulation block portion 103 has the negative electrodes 105a and 105b which are an electrode pair electrically connected to the conducting wires 102a and 102b as an conducting wire pair, and the fixing hooks 106R and 106L which urge the electrode pair toward the vein inner wall $V_s$.

The length of each of the arcuate arm portions 106a and 106c is equal to or greater than ½ of the circumferential length in the cross-section perpendicular to the central axis $O_V$ of the vein inner wall $V_s$ such that in urging toward the vein inner wall $V_s$, the fixing hooks 106R and 106L are deformed in a shape following the arcuate curved shape of the vein inner wall $V_s$. For this reason, the fixing hooks 106R and 106L and the support 103a connected to the fixing hooks 106R and 106L are arranged along the vein inner wall $V_s$, the flow of blood in the superior vena cava $V_1$ is not easily inhibited. As a result, even when the electrostimulation block portion 103 is placed in the vein, it is possible to suppress the occurrence of thrombus.

As shown in FIG. 1B, the rotary member 107 has engagement grooves 107d (engagement portions) which are detachably engaged with the electrostimulation block portion 103, and rotates the electrostimulation block portion 103 inserted into the superior vena cava $V_1$ around the central axis $O_v$ of the superior vena cava $V_1$ through the engagement groove 107d. In this embodiment, the rotary member 107 serves as an introducer which is a tubular member for guiding insertion of the electrostimulation block portion 103 and the electrostimulation lead 102 into the superior vena cava $V_1$.

The schematic configuration of the rotary member 107 is as shown in FIGS. 5A, 5B, and 5C. That is, the rotary member 107 includes a tubular portion 107a which substantially has a cylindrical tubular shape, a pair of engagement grooves 107d (engagement portions) which are provided at the leading end of the tubular portion 107a, and an insertion slot portion 107b which is provided at the base end of the tubular portion 107a, into which the electrostimulation block portion 103 and the electrostimulation lead 102 will be inserted, and is embedded with a blood leakage prevention valve (not shown).

The outer diameter of the tubular portion 107a is smaller than the inner diameter of the superior vena cava $V_1$. In particular, the leading end portion of the tubular portion 107a is tapered such that the diameter is reduced toward the leading end side.

The inner diameter of a through hole 107c which passes through the tubular portion 107a is greater than the outer diameter of the sheathing member 102c and is set such that the fixing hooks 106R and 106L of the electrostimulation block portion 103 can pass therethrough in a folded state. That is, the through hole 107c has an inner diameter which is greater than at least a diameter obtained by adding two times the wire diameter of the fixing hooks 106R and 106L to the outer diameter of the support 103a.

In this embodiment, the shape of each engagement groove 107d is constituted by a V-shaped cutout which is opened in the circumferential direction in the leading end portion of the tubular portion 107a with a decreasing width toward the base end side in the lateral surface of the leading end portion.

The size of the V shape of each engagement groove 107d is set such that the opening is greater than the wire diameter of the fixed shaft end 106e of each of the fixing hooks 106R and 106L, and the groove depth is greater than at least half of the wire diameter of the fixed shaft end 106e. Thus, the engagement groove 107d can be engaged with the corresponding fixed shaft end 106e in the circumferential direction of the tubular portion 107a.

In this embodiment, the position in the circumferential direction of each engagement groove 107d is set at a position where the circumference is divided unequally. For this reason, a virtual line which connects the center of each engagement groove 107d constitutes a chord which does not pass through a central axis $O_7$ in the circumference at the leading end of the tubular portion 107a.

Thus, when each engagement groove 107d is engaged with the corresponding fixed shaft end 106e, as shown in FIG. 2, engagement can be made in a state where the central axis $O_3$ of the support 103a is decentered toward the electrode portion 105 with respect to the central axis $O_7$ of the through hole 107c. In this embodiment, the lateral surface of the support 103a on the electrode portion 105 side is decentered to an extent so as to be inscribed in the through hole 107c at the leading end.

When the lateral surface of the support 103a on the electrode portion 105 can be inscribed in the through hole 107c at the leading end in accordance with the position where the fixed shaft end 106e is provided, the engagement groove 107d may be arranged to face the diameter direction of the through hole 107c.

As described above, the rotary member 107 is formed in a tubular shape through which the electrostimulation lead 102 passes, and includes the engagement grooves 107d which are groove portions provided to be engageable with the fixed shaft ends 106e as the convex portions of the electrostimulation block portion 103 in the circumferential direction of rotation.

The rotary member 107 can be configured by providing a pair of engagement grooves 107d at the leading end of an appropriate introducer which is used when a catheter-like member is inserted into the vein. For this reason, the shape of a portion of the rotary member 107 excluding the engagement grooves 107d can be similar to an appropriate introducer in the related art. That is, an introducer in the related art is of a peel-off type (tearing elimination type) or the like, and this shape type may be used.

For example, as an introducer which can be used as the rotary member 107 when the engagement grooves 107d are provided, Radifocus (Registered Trademark) introducer IIH (Product Name: manufactured by Terumo Medical Products) is an exemplary example.

Next, an operation to apply electrical stimulus to the vagus nerve VN in the electrostimulation system 101 will be described focusing on a method which places the electrostimulation block portion 103 in the superior vena cava $V_1$.

Figures 6A, 6B, 6C:
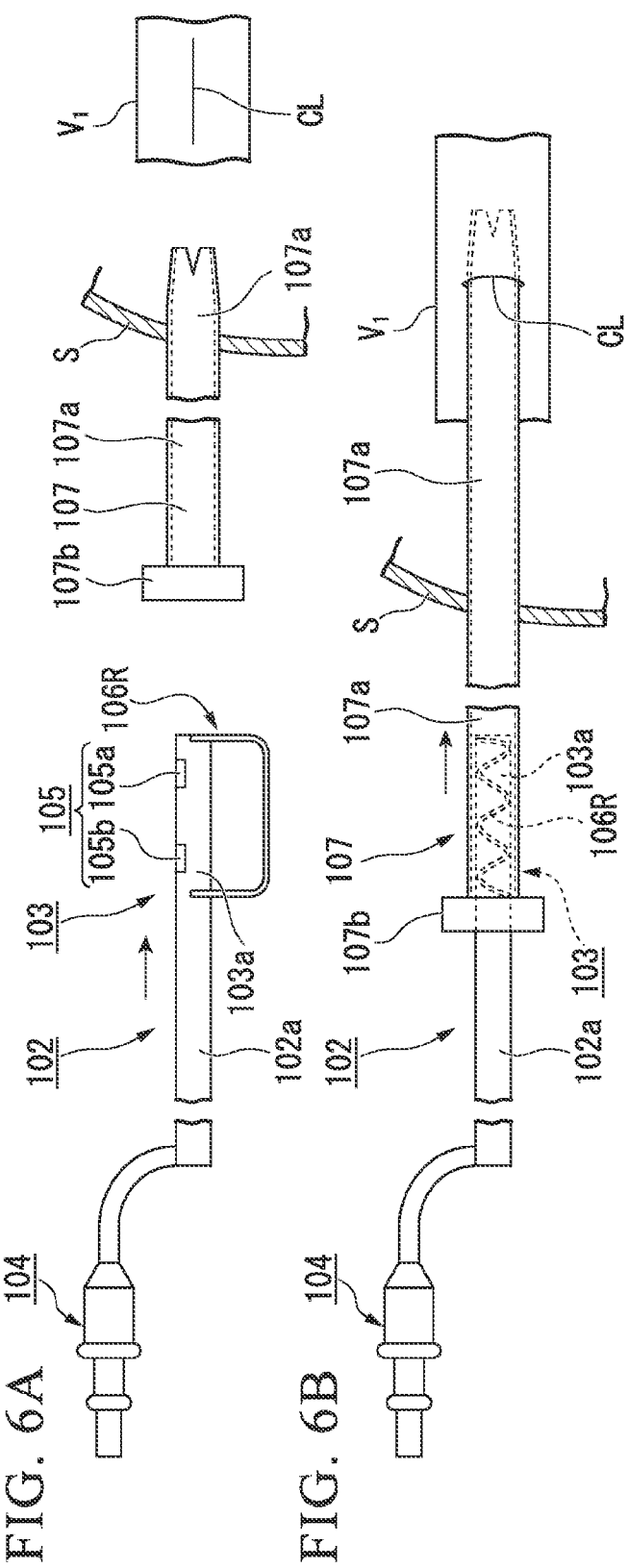
FIG. 6A is a process explanatory view showing an electrostimulation block insertion process in the electrostimulation system according to the first embodiment of the present invention.
FIG. 6B is a process explanatory view showing the electrostimulation block insertion process in the electrostimulation system according to the first embodiment of the present invention.
FIG. 6C is a process explanatory view showing the electrostimulation block insertion process in the electrostimulation system according to the first embodiment of the present invention.
Figure 7:
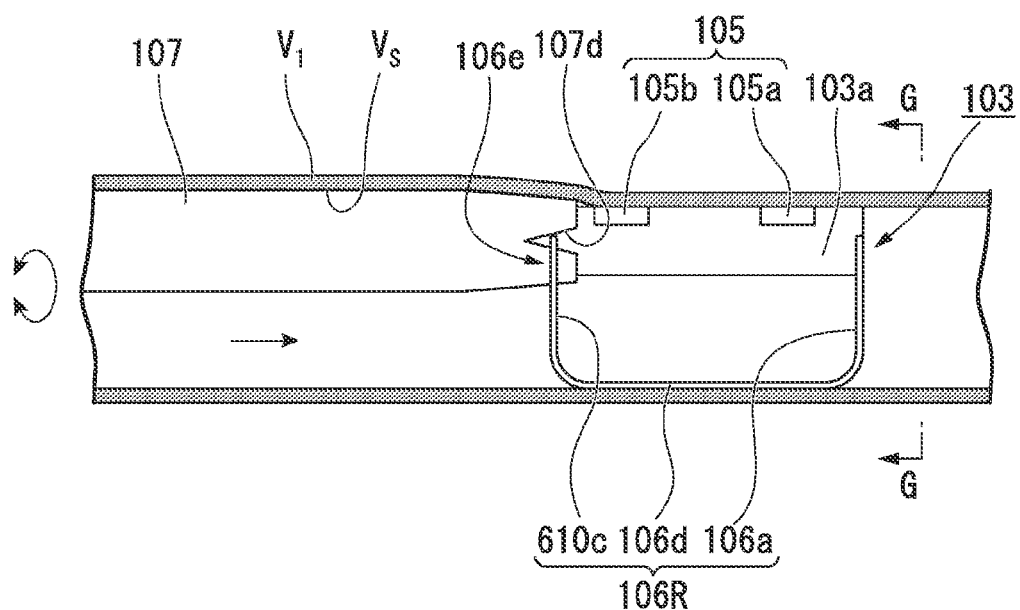
FIG. 7 is a process explanatory view showing an electrode alignment process in the electrostimulation system according to the first embodiment of the present invention.
Figure 8A:
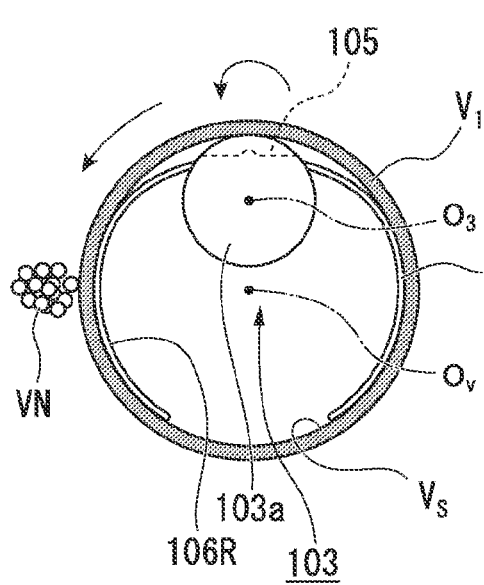
FIG. 8A is an operation explanatory view in a cross-section taken along the line G-G of FIG. 7.
Figure 8B:
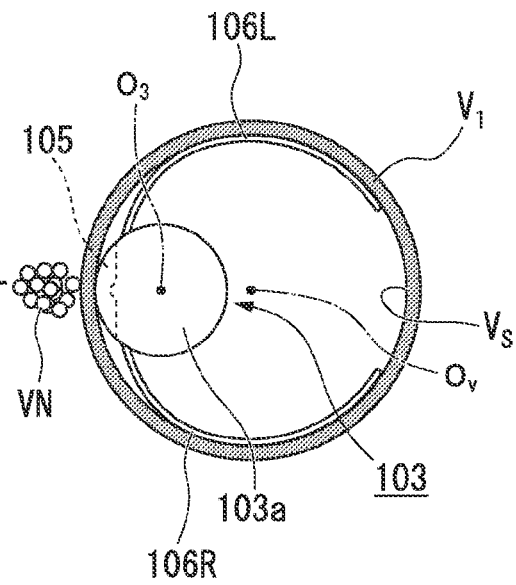
FIG. 8B is an operation explanatory view in a cross-section taken along the line G-G of FIG. 7.

FIGS. 6A, 6B, and 6C are process explanatory views showing an electrostimulation block insertion process in the electrostimulation system according to the first embodiment of the present invention. FIG. 7 is a process explanatory view showing an electrode alignment process in the electrostimulation system according to the first embodiment of the present invention. FIGS. 8A and 8B are operation explanatory views in a cross-section taken along the line G-G of FIG. 7.

In applying electrical stimulus to the vagus nerve VN by the electrostimulation system 101, an electrostimulation block insertion process, an electrode alignment process, and an electrostimulation process are performed sequentially.

The electrostimulation block insertion process is a process in which the electrostimulation block portion 103 of the electrostimulation system 101 is inserted into the superior vena cava $V_1$ along with the electrostimulation lead 102.

In this process, as shown in FIG. 6A, an operator makes an incision on a skin S in the cervical region to form an incision portion CL for inserting the rotary member 107 into the superior vena cava $V_1$.

Next, as shown in FIG. 6B, the operator inserts the tubular portion 107a into the incision portion CL from the leading end side and moves the leading end of the rotary member 107 toward the heart H in the superior vena cava $V_1$ so as to be placed near the vein portion in the vicinity of the vagus nerve VN, which will be subjected to electrostimulation.

At this time, the blood leakage prevention valve is embedded in the insertion slot portion 107b of the rotary member 107, such that, during the insertion process, it is possible to reduce blood leakage outside the body and also to realize insertion into the vein in a short time.

Next, the operator inserts the electrostimulation block portion 103 and the electrostimulation lead 102 from the insertion slot portion 107b in a state where the position of the rotary member 107 is fixed. At this time, the fixing hooks 106R and 106L have excellent flexibility, such that, when the electrostimulation block portion 103 is inserted into the rotary member 107, bending deformation occurs in a range of a gap between the through hole 107c and the support 103a and the through hole 107c and the sheathing member 102c, and the electrostimulation block portion 103 is folded. The fixing hooks 106R and 106L are constituted by a linear member which is bent so as to have an R shape in the corner portion, and do not have a shape to be caught by the inner circumferential surface of the through hole 107c. Thus, the fixing hooks 106R and 106L can smoothly slide in the axial direction in a folded state.

When the operator further inserts the electrostimulation lead 102, as shown in FIG. 6C, the electrostimulation block portion 103 emerges from the leading end of the rotary member 107 and is moved into the superior vena cava $V_1$.

When the electrostimulation block portion 103 emerges from the rotary member 107, external force from the through hole 107c which folds the fixing hooks 106R and 106L does not apply to the fixing hooks 106R and 106L, such that the fixing hooks 106R and 106L try to return to the shape in the natural state.

The shape in the natural state of the fixing hooks 106R and 106L is greater than the inner diameter of the vein inner wall $V_s$ of the superior vena cava $V_1$ (see the two-dot-chain line of FIG. 2). For this reason, the fixing hooks 106R and 106L come into contact with the vein inner wall $V_s$ and urge the vein inner wall $V_s$ outward in the radial direction.

In the cross-section perpendicular of the central axis $O_v$ of the vein inner wall $V_s$, the arcuate arm portions 106a and 106c of each of the fixing hooks 106R and 106L have a length equal to or greater than half of the circumferential length of the vein inner wall $V_s$ such that the electrode portion 105 in the support 103a is reliably urged outward in the radial direction. For this reason, the electrode portion 105 is urged to the vein inner wall $V_s$, and each electrode surface comes into close contact with the vein inner wall $V_s$. Thus, even when the base end of the electrostimulation lead 102 is rotated, the electrostimulation block portion 103 is fixed in a state where the position of the electrode portion 105 in the circumferential direction is not changed.

With the above, the electrostimulation block insertion process ends.

Next, the electrode alignment process is performed. This process is a process in which the electrode portion 105 is aligned at a position where the vagus nerve VN in the vicinity of the superior vena cava $V_1$ can be efficiently stimulated.

First, as shown in FIG. 7, the operator fixes the position of the electrostimulation block portion 103 to feed the rotary member 107 toward the electrostimulation block portion 103 and rotates rotary member 107 while the leading end of the rotary member 107 comes into contact with the arcuate arm portions 106c, such that the engagement grooves 107d are engaged with the fixed shaft ends 106e of the fixing hooks 106R and 106L. Thus, when the rotary member 107 is rotated, rotational force is transmitted to the electrostimulation block portion 103 through the fixed shaft ends 106e, thereby rotating the position of the electrostimulation block portion 103 against frictional force between the fixing hooks 106R and 106L and the vein inner wall $V_s$. Even during the rotation, urging force is applied from the fixing hooks 106R and 106L to the vein inner wall $V_s$. For this reason, the electrostimulation block portion 103 is rotated while maintaining the state along the circumferential direction in the vein inner wall $V_s$ along with the electrode portion 105.

As shown in FIG. 8A, if the position of the electrode portion 105 is excessively distant from the vagus nerve VN in the circumferential direction of the vein inner wall $V_s$, the vagus nerve VN is not electrically stimulated. For this reason, the operator rotates the rotary member 107 to carry out rotation adjustment of the electrostimulation block portion 103 such that, as shown in FIG. 8B, the electrode portion 105 is placed to face the vagus nerve VN in the radial direction with the vein inner wall $V_s$ sandwiched therebetween.

Determination on whether or not the electrode portion 105 is at the facing position may be made, for example, by connecting the connector 104 of the electrostimulation lead 102 to the electrostimulation device 1200 and monitoring the heart rate using an external electrocardiogram while applying electrostimulation pulses. If the electrode portion 105 goes to the position facing the vagus nerve VN, a decrease in the heart rate is observed. Thus, a position where the heart rate decreases the most may be found.

When the electrode portion 105 is adjusted with respect to a sympathetic nerve, a position where the heart rate increases may be found.

When the electrode portion 105 faces the vagus nerve VN, the rotation of the rotary member 107 stops and the alignment ends. Then, the rotary member 107 is withdrawn to the base end side to disengage the rotary member 107 from the electrostimulation block portion 103.

When the electrostimulation block portion 103 is implanted in the body or placed in the body for a long time, similarly to the introducer in the related art, the rotary member 107 is, for example, torn or the like and removed outside the vein or the body.

With the above, the electrode alignment process ends.

Next, the electrostimulation process is performed. This process is a process in which electrostimulation pulses set in advance are applied from the electrostimulation device 1200 to the electrode portion 105 of the electrostimulation block portion 103 facing the vagus nerve VN through the vein inner wall $V_s$ in the vicinity of the vagus nerve VN to carry out an electrostimulation treatment of the vagus nerve VN.

As described above, according to the electrostimulation system 101 of this embodiment, the electrostimulation block portion 103 can be inserted into the vein and the position thereof can be adjusted in the circumferential direction with respect to the vein inner wall $V_s$ by the rotary member 107 and can urge the electrode portion 105 to be attached to the vein inner wall $V_s$ by the fixing hooks 106R and 106L. For this reason, electrical stimulus can be indirectly applied to a nervous tissue in the vicinity of a vein without being in direct contact with the nervous tissue.

The fixing hooks 106R and 106L are provided, such that each electrode surface of the electrode portion 105 can be reliably urged to the vein inner wall $V_s$ and electrostimulation energy can be applied to a stimulation target (nerve or the like) outside the vein, into which the electrostimulation block portion 103 is inserted. At this time, since the electrode exposure angle is set in a range of 30° to 120°, the urged electrode surface comes into close contact with the vein inner wall $V_s$, such that the electrode surface is not in contact with blood. For this reason, electrostimulation energy is efficiently transmitted to the stimulation target without leaking into blood.

The electrostimulation block portion 103 can be aligned by the rotary member 107 so as to accurately face the stimulation target, minimizing the inter-electrode distance with respect to the stimulation target. As a result, electrostimulation can be carried out at a low voltage, and unnecessary stimulation to a portion which will not be stimulated, such as a phrenic nerve or a heart, can be reduced.

The rotary member 107 of this embodiment is a tubular member into which the electrostimulation block portion 103 and the electrostimulation lead 102 are insertable, and serves as an introducer which passes the electrostimulation block portion 103 and the electrostimulation lead 102 through the vein. For this reason, even when an introducer or the like is not separately prepared, insertion into the vein or removal from the vein can be easily carried out.

Since the electrostimulation block portion 103 is insertable into the vein in a state of being folded in the rotary member 107, it is possible to insert the electrostimulation block portion 103 greater than the cross-section of the vein with a load similar to the introducer of the related art. For this reason, for example, there is no case where the flow of blood is inhibited or the vein inner wall is damaged at the time of insertion into the vein.

As described above, according to this embodiment, in the electrostimulation for a linear tissue, such as a nervous tissue, nervous stimulation can be realized without causing surgical invasion to a nervous tissue as a target. The placement of the electrostimulation lead can be realized by a general transvenous approach which is in heavy usage at the time of catheter operation. In this case, electrostimulation is done indirectly, and the placement of the electrostimulation lead can be completed in a short time without regard to damage of a nervous tissue.

Next, first to third modifications of the electrostimulation system of this embodiment will be described.

In these modifications, only the shape of the engagement grooves 107d of the rotary member 107 which is used in the electrostimulation system of the first embodiment is changed.

With regard to the engagement grooves 107d, an example has been described where the sides which transmit rotational force for rotating the fixed shaft ends 106e are constituted by obliquely intersecting sides in the axial direction. However, the engagement portion of the rotary member is not particularly limited insofar as a cutout is provided to be of a size to accommodate the fixed shaft ends 106e and to have sides which intersect in the rotation direction to transmit rotational force. Hereinafter, these modifications will be described focusing on the differences from the first embodiment.

Figures 9A, 9B, 9C:
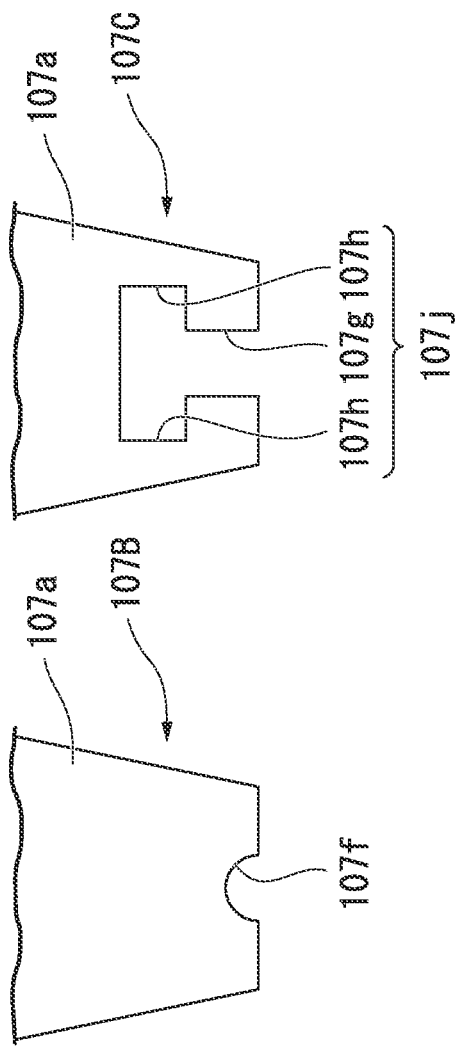
FIG. 9A is a partial enlarged view showing a main part of a first modification of the rotary member in the electrostimulation system according to the first embodiment of the present invention in front view.
FIG. 9B is a partial enlarged view showing a main part of a second modification of the rotary member in the electrostimulation system according to the first embodiment of the present invention in front view.
FIG. 9C is a partial enlarged view showing a main part of a third modification of the rotary member in the electrostimulation system according to the first embodiment of the present invention.

FIGS. 9A to 9C are partial enlarged views showing a main part of a modification (first to third modifications) of the rotary member in the electrostimulation system according to the first embodiment of the present invention in front view.

[First Modification]

As shown in FIG. 9A, a rotary member 107A of the first modification includes rectangular grooves 107e (engagement portions), instead of the engagement grooves 107d of the rotary member 107 of the first embodiment.

The rectangular grooves 107e are cutouts which are formed in a rectangular shape in side view to have a groove width greater than the wire diameter of the fixed shaft ends 106e and a groove depth greater than half of the wire diameter of the fixed shaft ends 106e.

According to this modification, since the groove width is uniform in the axial direction, even in a state where the fixed shaft ends 106e do not reach the groove bottom, rotational force can be transmitted to the electrostimulation block portion 103. For this reason, even when the position of the rotary member 107A is shifted in the axial direction during the rotation, the rotary member 107A can be continuously rotated. The rotation can be made without urging the fixed shaft ends 106e in the axial direction of the support 103a, reducing a load on the operator and reducing the possibility that the electrostimulation block portion 103 is moved in the axial direction of the vein inner wall $V_s$.

[Second Modification]

As shown in FIG. 9B, a rotary member 107E of the second modification includes semicircular grooves 107f (engagement portions), instead of the engagement grooves 107d of the rotary member 107 of the first embodiment.

The semicircular grooves 107f are semicircular cutouts which have a diameter slightly greater than the wire diameter of the fixed shaft ends 106e so as to be detachably engageable with the fixed shaft ends 106e.

According to this modification, since the semicircular grooves are detachably engageable with the fixed shaft ends 106e, transmission efficiency of rotational force to the fixed shaft ends 106e increases, and thus efficient working can be done.

In this modification, the cutouts may be modified to cutouts which are formed in a U shape in side view with a parallel groove slightly greater than the wire diameter of the fixed shaft ends 106e.

[Third Modification]

As shown in FIG. 9C, a rotary member 107C of the third modification includes T-shaped grooves 107j (engagement portions), instead of the engagement grooves 107d of the rotary member 107 of the first embodiment.

The T-shaped grooves 107j are cutouts which are formed in a T shape in side view, and have an axial slit 107g on a parallel groove formed on the leading end side to extend in the axial direction and a circumferential groove 107h provided to be bent from the base end side of the axial slit 107g to both outer sides in the circumferential direction.

The opening width of the axial slit 107g and the width in the axial direction of the circumferential groove 107h are set to be greater than the wire diameter of the fixed shaft ends 106e.

According to this modification, each fixed shaft end 106e is inserted on the leading end side within the range of the axial slit 107g to collide against the distal side, and the rotary member 107C is rotated, such that the fixed shaft end 106e is moved into the circumferential groove 107h extending to the opposite side to the rotation direction. Thus, during the rotation, in a state where the positions in the axial direction of the fixed shaft end 106e is regulated within the range of the groove width in the axial direction of the circumferential groove 107h, the fixed shaft end 106e can be rotated in the circumferential direction.

For this reason, the position in the axial direction of the electrostimulation block portion 103 during rotation can be stabilized. The operator operates the rotary member 107C in the axial direction to move the electrostimulation block portion 103 in the axial direction, such that the placement in the axial direction of the electrostimulation block portion 103 in the vein inner wall $V_s$ can be easily done.

In this modification, the circumferential groove 107h may be modified to a semicircular shape, a U shape, a V shape, or the like. The shape in side view is not limited to the T shape, and an appropriate key shape may be used.

[Fourth Modification]

Next, a fourth modification of the electrostimulation system of this embodiment will be described.

Figure 10A:
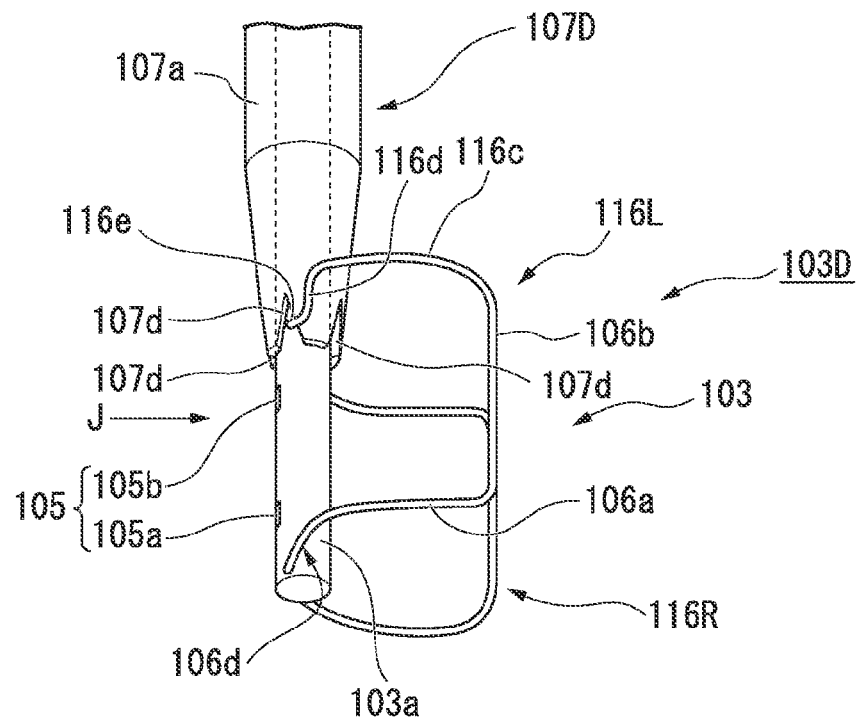
FIG. 10A is a schematic perspective view showing a main part of a modification (fourth modification) of the rotary member and the electrode urging member in the electrostimulation system according to the first embodiment of the present invention.
Figure 10B:
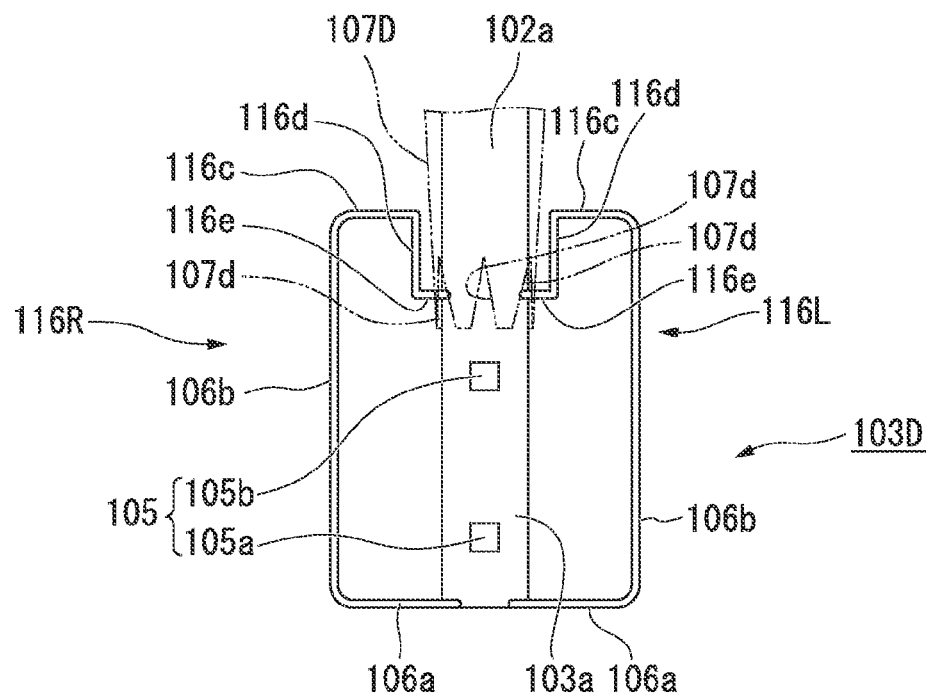
FIG. 10B is a side view when viewed from a direction indicated by an arrow of FIG. 10A.

FIG. 10A is a schematic perspective view showing a main part of a modification (fourth modification) of the rotary member and the electrode urging member in the electrostimulation system according to the first embodiment of the present invention. FIG. 10B is a side view when viewed from a direction indicated by an arrow J of FIG. 10A.

In this modification, as shown in FIGS. 10A and 10B, a rotary member 107D and an electrostimulation block portion 103D (electrostimulation block) are provided, instead of the rotary member 107 and the electrostimulation block portion 103 of the first embodiment.

The rotary member 107D is provided with the engagement grooves 107d of the rotary member 107 at three places or more. FIG. 10A shows an example where the engagement grooves are provided at four places at regular intervals in the circumferential direction.

The electrostimulation block portion 103D includes fixing hooks 116R and 116L (electrode urging member) which have a shape to be plane-symmetric in the same manner as the fixing hooks 106R and 106L, instead of the fixing hooks 106R and 106L of the electrostimulation block portion 103.

The fixing hook 116R (116L) includes a fixed shaft end 116e (convex portion) which protrudes obliquely from the same position as the fixed shaft end 106e outward in the radial direction, an axial arm portion 116d which extends from the leading end of the fixed shaft end 116e toward the base end along the axial direction of the support 103a, and an arcuate arm portion 116c which is connected to the axial arm portion 116d through an R-shaped bent portion and extends so as to overlap the arcuate arm portion 106a when viewed from the axial direction of the support 103a, instead of the fixed shaft end 106e and the arcuate arm portion 106c of the fixing hook 106R (106L). The arcuate arm portion 116c and the hook leading end portion 106b are connected to each other through a bent portion having an R shape in side view.

The length of the fixed shaft end 116e is set to a length such that a gap which is slightly wider than a thickness of the tubular portion 107a of the rotary member 107D on the leading end side is formed between the support 103a and the axial arm portion 116d.

According to this modification, the engagement grooves 107d at two adjacent places from among the engagement grooves 107d at the four places are engaged with a pair of fixed shaft ends 116e, such that, similarly to in the first embodiment, the electrostimulation block portion 103D can be rotated.

At this time, the axial arm portion 116d, which forms a gap slightly wider than the thickness of the tubular portion 107a on the leading end side between the support 103a and the axial arm portion 116d, is connected to the fixed shaft end 116e. Thus, the leading end of the rotary member 107D is guided while being sandwiched by a pair of axial arm portions 116d as approaching the fixed shaft ends 116e.

For this reason, even when the inner diameter of the through hole 107c is greater than the outer diameter of the support 103a, and there is a large amount of looseness in the radial direction, the position of the leading end of the rotary member 107D is centered by the axial arm portions 116d in the vicinity of the fixed shaft ends 116e. For this reason, it becomes more easy to engage the engagement grooves 107d with the fixed shaft ends 116e.

In disengaging the rotary member 107D in the circumferential direction after the rotary member 107D has been engaged with the electrostimulation block portion 103D, the rotary member 107D is urged to the opposite side of the circumferential direction by the axial arm portions 116d, such that the rotary member 107D is disengaged in the circumferential direction.

At the leading end of the rotary member 107D, since the engagement grooves 107d are provided at the four places, the engagement grooves 107d at two places closest to the positions of the fixed shaft ends 116e may be engaged with the fixed shaft ends 116e. For this reason, the rotary member 107D can be engaged with the fixed shaft ends 116e with a smaller rotation amount on the average compared to the first embodiment.

In this modification, these are combined with each other, such that the engagement of the rotary member 107D and the electrostimulation block portion 103D can be done smoothly and rapidly.

[Second Embodiment]

Next, an electrostimulation system according to a second embodiment of the present invention will be described.

Figure 11A:
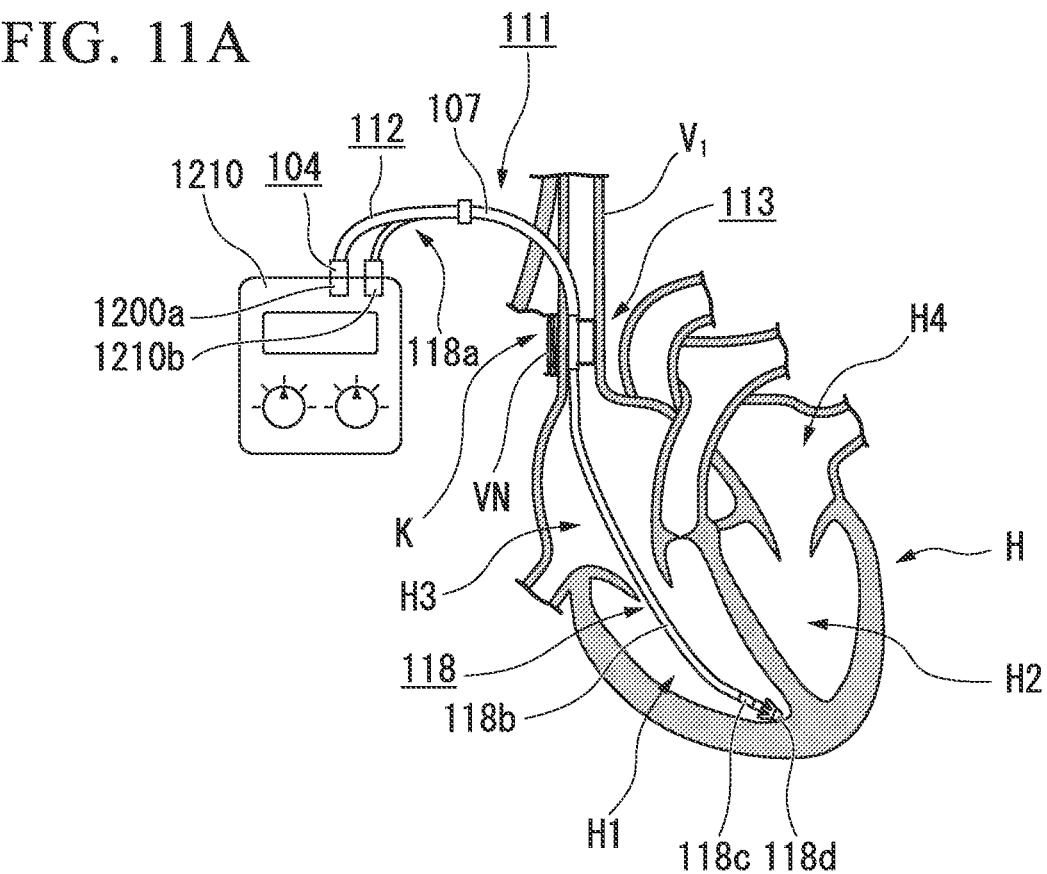
FIG. 11A is a schematic sectional view showing a state when an electrostimulation system according to a second embodiment of the present invention is loaded in a superior vena cava.
Figure 11B:
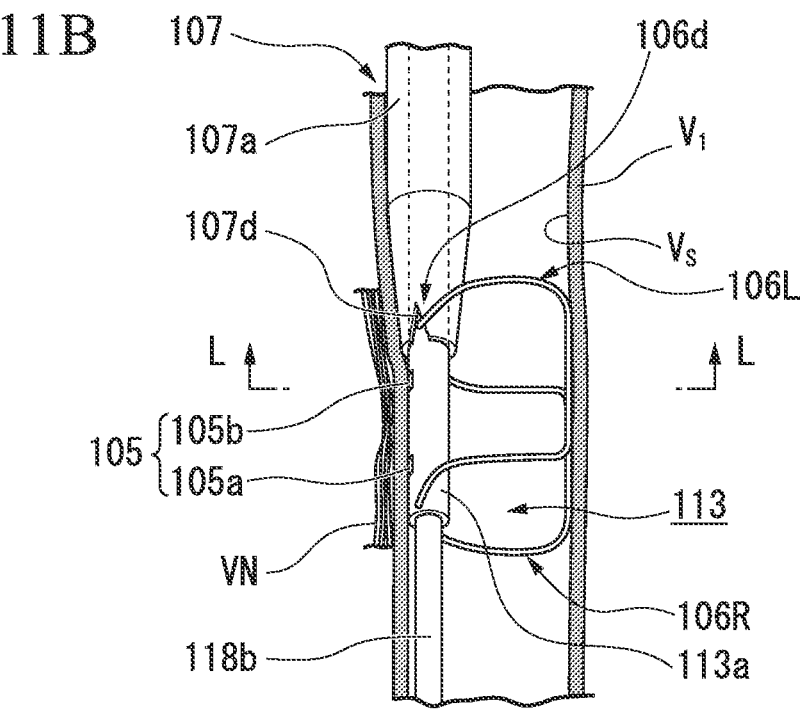
FIG. 11B is a schematic perspective view of a K portion of FIG. 11A on a magnified scale.
Figure 12:
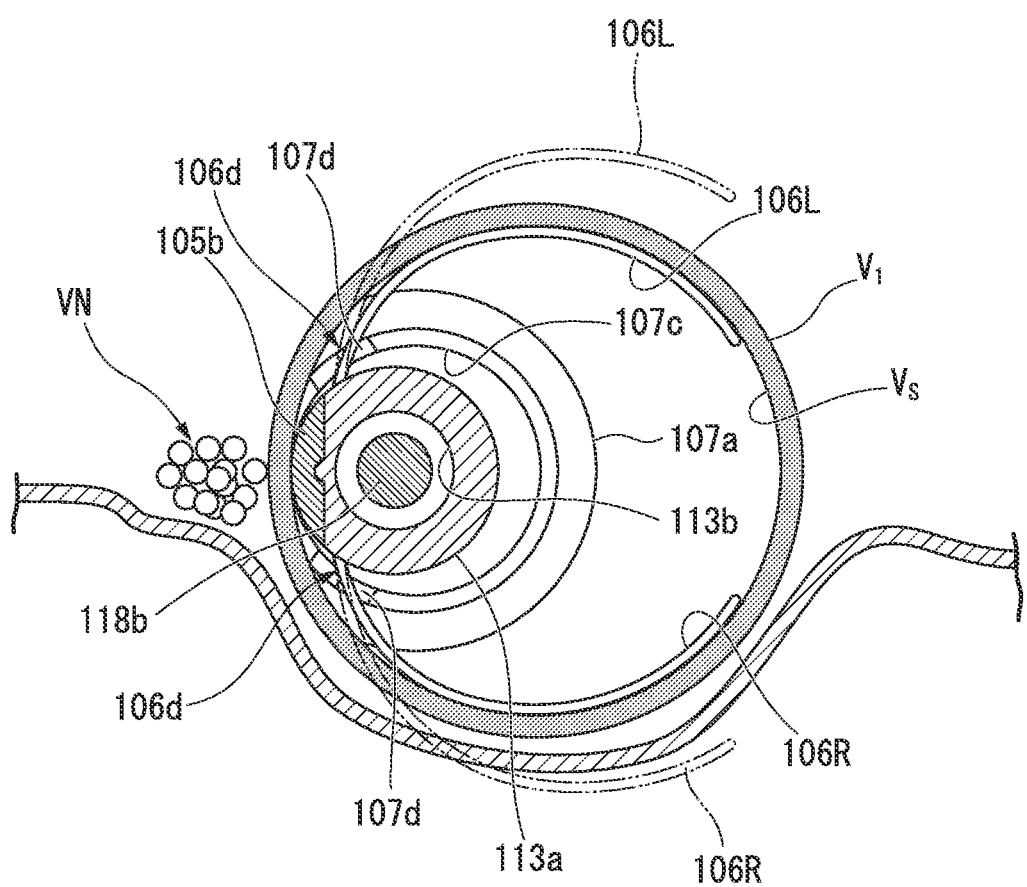
FIG. 12 is a sectional view taken along the line L-L of FIG. 11B.

FIG. 11A is a schematic sectional view showing a state when an electrostimulation system according to a second embodiment of the present invention is loaded in a superior vena cava. FIG. 11B is a schematic perspective view of a K portion of FIG. 11A on a magnified scale. FIG. 12 is a sectional view taken along the line L-L of FIG. 11B. FIG. 13A is a schematic front view of the electrostimulation system according to the second embodiment of the present invention. FIG. 13B is a sectional view taken along the axial direction of an electrostimulation block which is used in the electrostimulation system according to the second embodiment of the present invention.

As shown in FIGS. 11A and 11B, in an electrostimulation system 111 of this embodiment, a pacing lead 118 is further provided, and instead of the electrostimulation lead 102 and the electrostimulation block portion 103 of the first embodiment, an electrostimulation lead 112 (sheathed conducting wire member) and an electrostimulation block portion 113 (electrostimulation block) are provided. Hereinafter, a description will be provided focusing on the differences from the first embodiment.

The electrostimulation lead 112 and the pacing lead 118 of the electrostimulation system 111 are electrically connected to an electrostimulation device 1210 through connectors 104 and 118a provided at the base end side thereof.

Similarly to the first embodiment, the electrostimulation lead 112 and the electrostimulation block portion 113 provided at the leading end of the electrostimulation lead 112 are inserted into the superior vena cava $V_1$ to apply the same electrical stimulus to the vagus nerve VN.

The pacing lead 118 applies electrical stimulus to the heart H from the electrode arranged in the heart H or detects electrical excitation.

Although the pacing lead 118 may have the common configuration of a type which is used in a heart treatment of the related art, hereinafter, as shown in FIG. 13A, an example has been described where a connector 118a, a lead portion 118b, a positive electrode 118c, a blade-shaped member 118e, and a negative electrode 118d are provided in that order from the base end side.

Similarly to the connector 104, the connector 118a may be an IS1 connector or a waterproof connector in accordance with whether the electrostimulation device 1210 is provided inside or outside the body.

The lead portion 118b is connected to the positive and negative electrodes of the connector 118a. The lead portion 118b insulates a pair of conducting wires, which are constituted by twisted wires made of for example, nickel-cobalt alloy, from each other, and insulates and sheathes the outer circumferential surfaces of the conducting wires. As the lead portion 118b, for example, a polyurethane tube having two lumens may be used. The outer circumferential surface of the polyurethane tube may be subjected to thrombus prevention coating.

In this embodiment, the outer diameter of the lead portion 118b is about φ1 mm.

The positive electrode 118c and the negative electrode 118d are respectively connected to the conducting wires which pass through the lead portion 118b.

The surface of the negative electrode 118d is subjected to porous platinum coating, porous iridium coating, iridium oxide coating, or titanium nitride coating. Thus, the electrode surface area increases compared to a case where no coating is carried out.

The electrode surface area is adjusted in such a manner, such that, in order to apply electrical stimulus from the negative electrode 118d or to detect electrical excitation, biological impedance between the negative electrode 118d and the positive electrode 118c is adjusted to an appropriate value.

The blade-shaped member 118e is a member for locking to the shape of the heart H, and is a blade-shaped protrusion which protrudes from the lead portion 118b near the negative electrode 118d outward in the radial direction between the positive electrode 118c and the negative electrode 118d. Thus, a structure is formed such that the negative electrode 118d easily comes into contact with a heart tissue.

In this embodiment, the circumscribed circle diameter of the leading end in the protrusion direction of the blade-shaped member 118e is set so as not to exceed φ2 mm.

The pacing lead 118 passes through the electrostimulation lead 112, is inserted into the superior vena cava $V_1$, and is arranged such that the negative electrode 118d comes into contact with the inner wall of a right ventricle H1 through a right atrium H3.

The electrostimulation device 1210 is provided with a connection terminal 1200a which is connected to the connector 104 to apply the same electrostimulation pulses as in the electrostimulation device 1200 of the first embodiment to the connector 104, and a connection terminal 1210b which is connected to the connector 118a to transfer electrical signals between the negative electrode 118d and the positive electrode 118c of the pacing lead 118.

Though not particularly shown, the electrostimulation device 1210 has a circuit which sends electrical stimulus to the electrostimulation lead 112, a circuit which sends electrical stimulus to the pacing lead 118, and a circuit which detects electrical excitation of the heart H transmitted through the positive electrode 118c and the negative electrode 118d.

The electrostimulation device 1210 is provided with a heart rate measurement section which measures the heart rate by using the pacing lead 118, an electrostimulation pulse voltage supply section which supplies an electrostimulation pulse voltage to the electrostimulation lead 112 and the pacing lead 118, and a control section which controls the supply of the electrostimulation pulse voltage on the basis of the state of the heart H.

The heart rate measurement section can detect the potential of the positive electrode 118c with respect to the potential of the negative electrode 118d to obtain a potential change according to the electrical activity of the heart H, that is, an electrocardiographic signal. The heart rate measurement section can measure the heart rate from a time interval, in which the potential of the electrocardiographic signal or a change rate becomes greater than a predetermined threshold value, on the basis of the waveform of the obtained electrocardiographic signal.

When the heart H is in the bradycardiac state and the heart rate decreases, the electrostimulation pulse voltage supply section supplies the electrostimulation pulse voltage having comparatively large energy between the negative electrode 118d and the positive electrode 118c of the pacing lead 118. Thus, the heart H is stimulated and the heart rate increases.

Meanwhile, similarly to the electrostimulation lead 102 of the first embodiment, the electrostimulation lead 112 is provided with a negative electrode 105a and a positive electrode 105b (see FIGS. 13A and 13B). With this, when the heart H is in the tachycardiac state or the fibrillation state and the heart rate increases, the electrostimulation pulse voltage having comparatively small energy can be supplied between the negative electrode 105a and the positive electrode 105b. Thus, the vagus nerve VN in the vicinity of the superior vena cava $V_1$ is stimulated and the heart rate decreases.

Although the conditions for electrostimulation of the electrostimulation lead 112 and the pacing lead 118 are different, as the conditions, the magnitude of the electrostimulation pulse voltage, frequency, pulse width, stimulation end time, stimulation start time, stimulation duration time, electrostimulation stoppage, and the like are exemplified.

As shown in FIGS. 13A and 13B, the electrostimulation lead 112 includes a tubular sheathing member 112a, instead of the sheathing member 102c of the electrostimulation lead 102 of the first embodiment.

The tubular sheathing member 112a is provided with a hollow portion 112b which passes therethrough in the central portion in the radial direction of the sheathing member 102c.

The outer diameter of the tubular sheathing member 112a is of a size so as to pass through the through hole 107c of the rotary member 107, and in this embodiment, is φ2 mm.

In this embodiment, as the hollow portion 112b, a cylindrical hole is used which has an inner diameter such that the pacing lead 118 excluding the connector 118a can pass therethrough. In this embodiment, the inner diameter of the hollow portion 112b is φ1.5 mm.

The conducting wires 102a and 102b which are introduced from the sheathing tube 102d connected to the base end of the electrostimulation lead 112 pass through the tubular sheathing member 112a in a range of the thickness of the tubular sheathing member 112a, are insulated from each other, and pass through the electrostimulation lead 112 in the axial direction without being exposed to the outer circumferential surface of the tubular sheathing member 112a and the inner circumferential surface of the hollow portion 112b.

The electrostimulation block portion 113 is provided with a tubular support 113a, instead of the support 103a of the electrostimulation block portion 103 of the first embodiment.

The tubular support 113a is provided on the leading end side of the tubular sheathing member 112a, and supports the electrode portion 105 and the fixing hooks 106R and 106L in the lateral surface. The tubular support 113a has passed therethrough the conducting wires 102a and 102b extending from the tubular sheathing member 112a in a state of being insulated from each other and guides the conducting wires 102a and 102b to the electrode portion 105. The tubular support 113a includes a hollow portion 113b, which communicates with the hollow portion 112b and has the same diameter as the hollow portion 112b, in the central portion thereof.

In this embodiment, the tubular support 113a has a columnar outer shape having the same diameter as the tubular sheathing member 112a, and is formed of the same insulating material as the tubular sheathing member 112a so as to be combined with the tubular sheathing member 112a.

The electrode portion 105 and the fixing hooks 106R and 106L are provided in the tubular support 113a at the same positions as the support 103a.

As shown in FIG. 13B, similarly to the tubular sheathing member 112a, the conducting wires 102a and 102b pass through the tubular support 113a in a range of the thickness of the tubular support 113a and are respectively electrically connected to the negative electrode 105a and the positive electrode 105b.

As described above, in the electrostimulation lead 112 and the electrostimulation block portion 113 of the embodiment, the tubular sheathing member 112a and the tubular support 113a are provided, and the hollow portions 112b and 113b communicate with each other in the central portions, such that the pacing lead 118 can pass therethrough. This is different from the first embodiment.

For this reason, according to the electrostimulation system 111, similarly to the first embodiment, the electrostimulation block insertion process can be performed in which the electrostimulation block portion 113 and the electrostimulation lead 112 are inserted into the superior vena cava $V_1$ through the rotary member 107.

In the electrostimulation block insertion process of this embodiment, the pacing lead 118 passes through the hollow portion 112b and 113b in the electrostimulation lead 112 and the electrostimulation block portion 113 which are inserted into the superior vena cava $V_1$, such that the leading end portion of the pacing lead 118 can be inserted into the right ventricle H1 and the positive electrode 118c and the negative electrode 118d can be close to or come into contact with the inner wall of the right ventricle H1.

Next, the electrode alignment process can be performed in which the engagement grooves 107d of the rotary member 107 are engaged with the fixed shaft ends 106e to rotate the rotary member 107, and the position in the circumferential direction of the electrostimulation block portion 103 is aligned in the vein inner wall $V_s$.

In this embodiment, since the pacing lead 118 is provided, the heart rate is monitored by using the pacing lead 118 while the electrostimulation pulses are applied to the electrostimulation lead 112, making it possible to determine whether or not the electrode portion 105 is at the position facing the vagus nerve VN.

In order to facilitate the adjustment, the electrostimulation device 1210 may produce sound in accordance with the heart rate, and a change in the heart rate may be expressed by, for example, the high and low levels or the tone of sound. In this case, the operator can hear sound to confirm a change in the heart rate, efficiently advancing working. The heart rate may be displayed on a liquid crystal monitor or the like in the form of numerical value, graph, or the like.

Thus, as shown in FIGS. 11B and 12, the vagus nerve VN and the electrode portion 105 can be arranged to face each other with the vein sandwiched therebetween.

The connectors 104 and 118a are connected to the electrostimulation device 1210, such that electrical stimulus can be applied to the vagus nerve VN through the electrostimulation lead 112, and electrical stimulus can be applied to the heart H or electrical excitation can be detected through the pacing lead 118.

As described above, according to this embodiment, electrostimulation can be carried out for a linear tissue, such as a nervous tissue, placement can be made without causing damage to a nervous tissue as a target, and pacing or sensing of the heart H can be carried out along with electrostimulation to the nervous tissue.

In this embodiment, the pacing lead 118 is embedded in the electrostimulation lead 112 as a single body and can be inserted into the vein. For this reason, it is possible to reduce the number of vein insertion slots and to reduce blood flow inhibition since multiple leads are arranged in parallel in the vein.

Although in this embodiment, an example has been described where the pacing lead 118 is placed in the right ventricle H1, the pacing lead 118 may be formed as a single body with another lead placed in the right atrium H3, or another lead placed in a tubular vein of the surface layer of the left ventricle H2 and the electrostimulation lead 112 may be formed as a single body. In this case, electrostimulation of a nervous tissue may be carried out on the basis of the electrocardiographic monitor of tissues in which these leads are placed.

[Third Embodiment]

Next, an electrostimulation system according to a third embodiment of the present invention will be described.

Figure 14A:
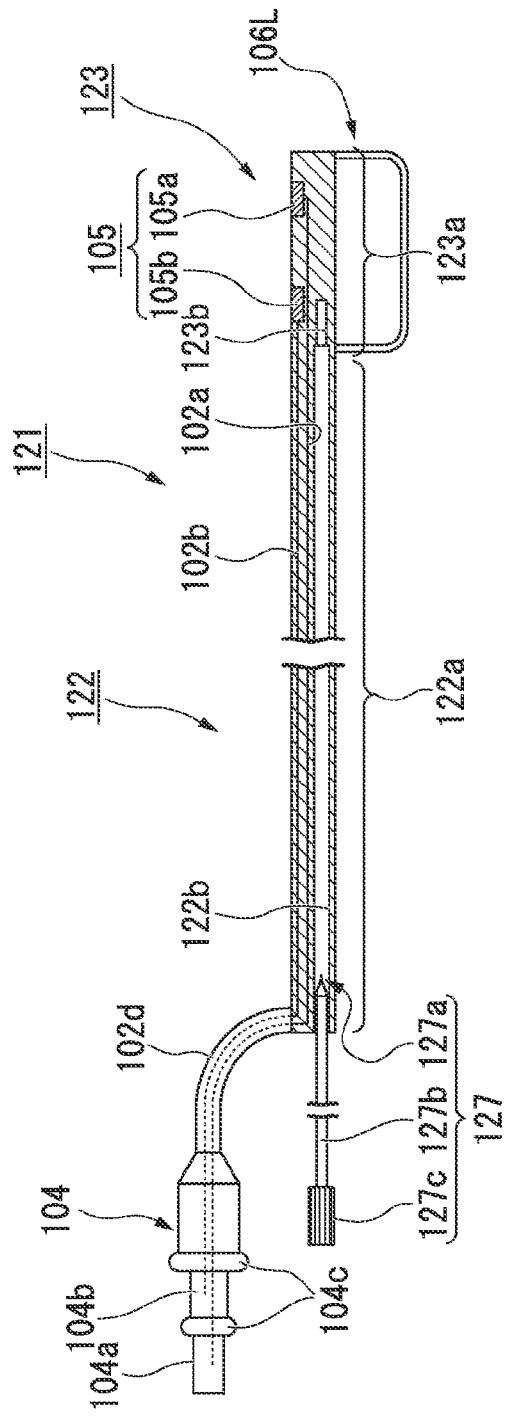
FIG. 14A is a schematic partial sectional view taken along the axial direction of an electrostimulation system according to a third embodiment of the present invention.
Figure 14B:
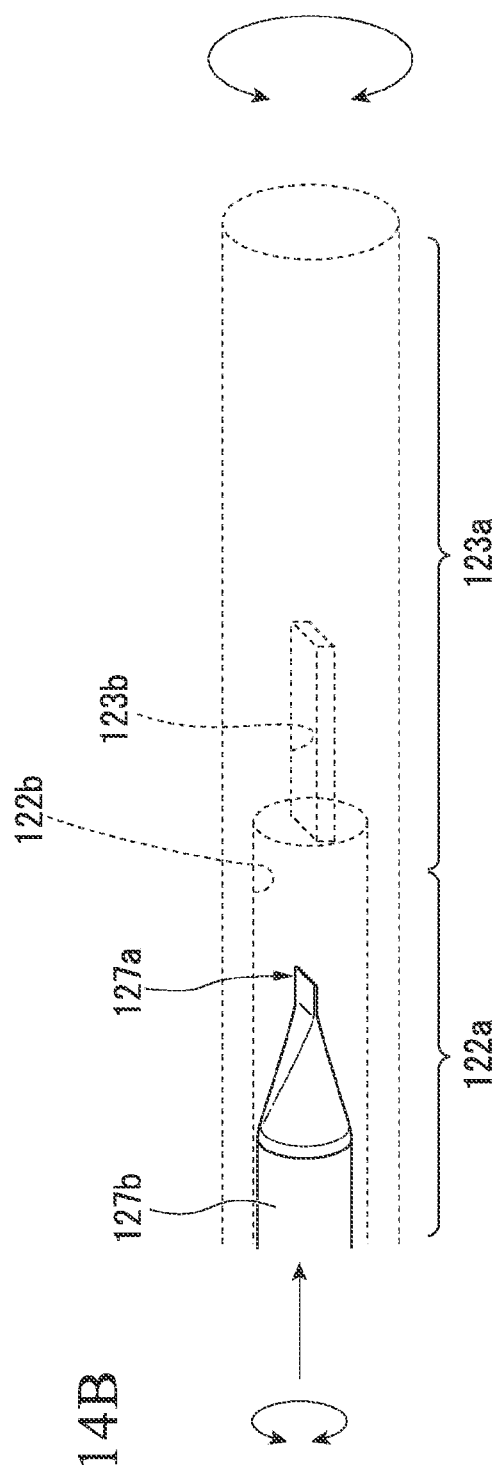
FIG. 14B is a schematic perspective view of the leading end of a rotary member according to the third embodiment of the present invention.

FIG. 14A is a schematic partial sectional view taken along the axial direction of an electrostimulation system according to a third embodiment of the present invention. FIG. 14B is a schematic perspective view of the leading end of a rotary member according to the third embodiment of the present invention.

As shown in FIGS. 14A and 14B, an electrostimulation system 121 of this embodiment includes an electrostimulation lead 122 (sheathed conducting wire member) an electrostimulation block portion 123 (electrostimulation block), and a rotary member 127, instead of the electrostimulation lead 102, the electrostimulation block portion 103, and the rotary member 107 in the electrostimulation system 101 of the first embodiment. Hereinafter, a description will be provided focusing on the difference from the first embodiment.

The electrostimulation lead 122 is provided with a hollow portion 122b, through which the rotary member 127 described below passes, inside the electrostimulation lead 102 of the first embodiment.

The electrostimulation block portion 123 includes a support 123a, which has an angular groove portion 123b at a position, at which the hollow portion 122b communicates therewith, on the base end side of the support 103a, instead of the support 103a of the electrostimulation block portion 103 of the first embodiment.

The angular groove portion 123b has an elongated angular cross-section along one diameter of the hollow portion 122b and extends to the leading end side.

Similarly to the support 103a of the first embodiment, the support 123a includes an electrode portion 105 and fixing hooks 106R and 106L (FIG. 14A is a sectional view, thus the fixing hook 106R is not shown). In this embodiment, however, the fixed shaft ends 106e have only a function as the fixed ends of the fixing hooks 106R and 106L, not having a function as a convex portion which is engaged with the rotary member.

The rotary member 127 is a flexible member which can pass through the hollow portion 122b, and is constituted by a stylet which has a shaft portion 127b having rigidity so as to transmit torque to the leading end side, a plate-shaped portion 127a (engagement portion) provided to be inserted into the angular groove portion 123b at the leading end of the shaft portion 127b and to be engageable in the circumferential direction, and a handle portion 127c rotating the shaft portion 127b at the base end of the shaft portion 127b.

The length of the shaft portion 127b is set to a length such that the plate-shaped portion 127a is insertable into the angular groove portion 123b in a state where the handle portion 127c is placed outside the body.

As the material of the shaft portion 127b, for example, a superelastic wire made of nickel-titanium may be used. For example, in the case of the electrostimulation lead 122 in which the outer diameter of a hollow sheathing member 122a is about ϕ2 mm, a superelastic wire having an outer diameter in a range of ϕ0.3 mm to ϕ1 mm is preferably used. Thus, satisfactory torque transmissibility can be obtained.

In this embodiment, since the shaft portion 127b passes through the hollow portion 122b, the shaft portion 127b does not come into contact with blood, the vein inner wall $V_s$, or the like. For this reason, the shaft portion 127b may be made of a material having no biocompatibility. Sheathing processing for biocompatibility or the like may be omitted.

Although in this embodiment, the handle portion 127c is provided for ease of the rotation operation, when the rotation operation may be easily made even with no handle portion 127c because of the shaft diameter of the shaft portion 127b or the like, the handle portion 127c may not be provided.

In this embodiment, the angular groove portion 123b as a groove portion is formed in the electrostimulation block portion 123 at a position inside the outer circumference of the electrostimulation lead 122. The rotary member 127 is formed in a shaft shape so as to pass through the electrostimulation lead 122, and has, at the leading end thereof, the plate-shaped portion 127a as a convex portion which is provided to be engageable with the angular groove portion 123b of the electrostimulation block portion 123 in the circumferential direction of rotation.

According to the electrostimulation system 121 of this embodiment, after the electrostimulation lead 122 is assembled in a state where the rotary member 127 passes through the hollow portion 122b and the plate-shaped portion 127a is engaged with the angular groove portion 123b, the electrostimulation block insertion step into the superior vena cava $V_1$ may be performed by using an introducer (not shown) of the related art with no engagement portions, such as the engagement grooves 107d at the leading end, instead of the rotary member 107 of the first embodiment, in the same manner as in the first embodiment.

At this time, the operator operates the rotary member 127 straight, the electrostimulation block portion 123 and the electrostimulation lead 122 can be moved in the superior vena cava $V_1$ along the axial direction of the superior vena cava $V_1$. For this reason, buckling rigidity of the electrostimulation lead 122 which is necessary for moving the electrostimulation block portion 103 in the vein in the axial direction in a state where the fixing hooks 106R and 106L are open may satisfy combined rigidity of the sheathing member 122a and the rotary member 127. In this way, a portion of rigidity of the electrostimulation lead 122 is imposed on the rotary member 127, making it possible to achieve the reduction in the diameter of the hollow sheathing member 122a compared to a case where no rotary member 127 is provided.

Next, the electrode alignment process is performed in which the electrostimulation block portion 123 in the vicinity of the vagus nerve VN is placed to face the vagus nerve VN in the superior vena cava $V_1$.

In the electrode alignment process of this embodiment, the operator rotates the handle portion 127c, such that torque is transmitted to the support 123a through the angular groove portion 123b engaged with the plate-shaped portion 127a of the rotary member 127. Thus, the electrostimulation block portion 123 is rotated in the circumferential direction.

After the electrode alignment process ends, the rotary member 127, and the introducer if necessary, is removed from the body, and the electrostimulation is carried out in the same manner as in the first embodiment.

As described above, according to the embodiment, as in the first embodiment, the electrostimulation block portion 123 can be aligned in the vein.

The veins have various sectional shapes, and there is also a vein which has a modified sectional shape far from a circular shape. The insertion length into the vein may be extended depending on the position of a nervous tissue.

Meanwhile, an introducer has an inner diameter significantly greater than the outer diameter of the electrostimulation lead 122. For this reason, as in the first embodiment, if an introducer is used as the rotary member, frictional force in the vein may increase at the time of rotation, making it difficult to carry out rotation adjustment.

In this embodiment, in such a case, the rotary member 127 does not come into contact with the vein inner wall $V_s$, such that with friction against the hollow portion 122b, rotation adjustment can be stably carried out without being influenced by the shape of the vein or the like. The electrostimulation lead 122 which rotates in the vein has a diameter smaller than the introducer, thus the frictional resistance decreases.

For this reason, it is possible to reduce a load imposed on a patient at the time of insertion or the placement time of the electrostimulation block portion 123, and to improve the QOL (Quality of Life) of the patient.

[Fourth Embodiment]

Next, an electrostimulation system according to a fourth embodiment of the present invention will be described.

Figure 15:
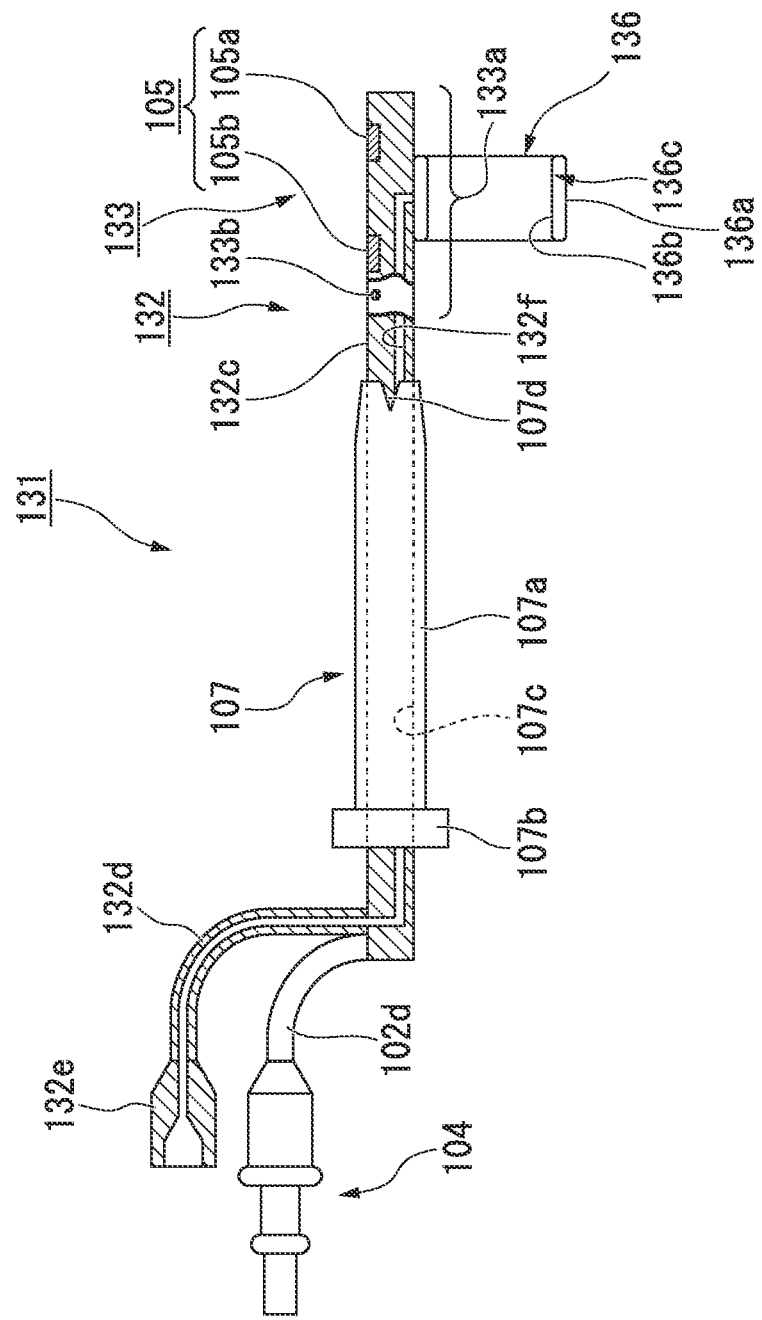
FIG. 15 is a schematic partial sectional view taken along the axial direction of an electrostimulation system according to a fourth embodiment of the present invention.
Figure 16:
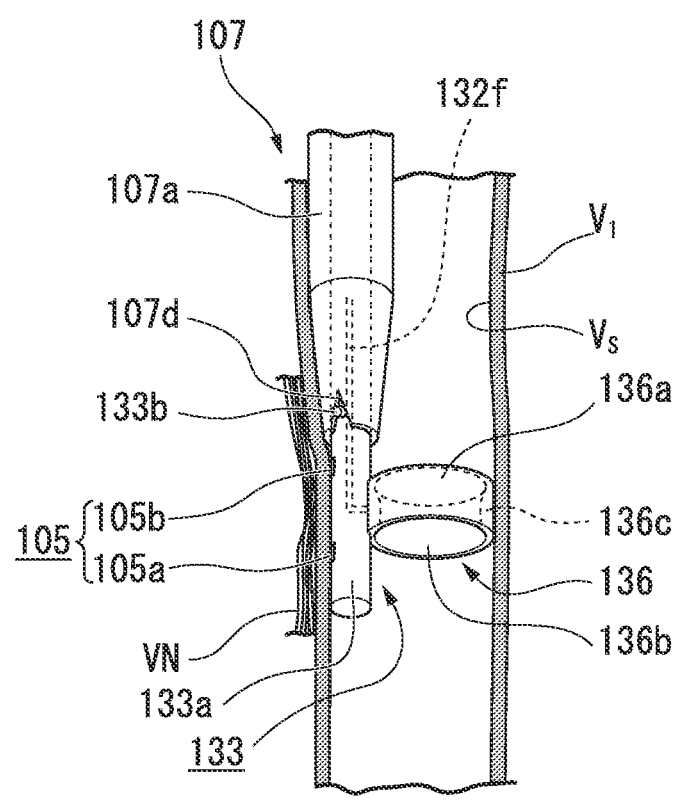
FIG. 16 is a schematic perspective view showing a state when the electrostimulation system according to the fourth embodiment of the present invention is loaded in a superior vena cava.

FIG. 15 is a schematic partial sectional view taken along the axial direction of an electrostimulation system according to a fourth embodiment of the present invention. FIG. 16 is a schematic perspective view showing a state where the electrostimulation system according to the fourth embodiment of the present invention is placed in a superior vena cava.

As shown in FIGS. 15 and 16, the electrostimulation system 131 of this embodiment includes an electrostimulation lead 132 (sheathed conducting wire member) and an electrostimulation block portion 133 (electrostimulation block), instead of the electrostimulation lead 102 and the electrostimulation block portion 103 in the electrostimulation system 101 of the first embodiment. Hereinafter, a description will be provided focusing on the differences from the first embodiment.

The electrostimulation lead 132 includes a sheathing member 132c, instead of the sheathing member 102c of the electrostimulation lead 102 of the first embodiment, and further includes, in the base end portion, a fluid supply tube 132d which has a syringe connection connector 132e connected to a syringe (not shown).

The syringe (not shown) is connected to the syringe connection connector 132e and injects a fluid, such as a normal saline solution. The syringe connection connector 132e is provided with a check valve, such that even when the syringe is pulled out after the normal saline solution is injected, the injected normal saline solution does not flow backward.

The sheathing member 132c is configured such that a flow channel 132f which communicates to the path in the fluid supply tube 132d is provided to extend in the axial direction in a linear member formed of the same material as the sheathing member 102c to have the same diameter as the sheathing member 102c. Though not shown in FIG. 15, similarly to the sheathing member 102c, the sheathing member 132c has passed therethrough the conducting wires 102a and 102b electrically connected to the connector 104.

The electrostimulation block portion 133 includes a support 133a, a cylindrical protrusion 133b (convex portion), and a cylindrical balloon 136 (electrode urging member), instead of the support 103a and the fixing hooks 106R and 106L of the electrostimulation block portion 103 of the first embodiment.

The support 133a is a shaft-like member which is provided on the leading end side of the sheathing member 132c, and has an electrode portion 105 constituted by a negative electrode 105a and a positive electrode 105b in the lateral surface in the same manner as the support 103a.

Cylindrical protrusions 133b which protrude outwardly in the radial direction are respectively provided at the same positions as the fixed shaft ends 106e of the first embodiment in the lateral surface on the based end side compared to the positive electrode 105b.

In this embodiment, the support 133a has a columnar outer shape having the same diameter as the sheathing member 132c, and is molded as a single body with the sheathing member 132c by using the same insulating material as the sheathing member 132c. The cylindrical protrusions 133b are also formed as a single body.

Inside the support 133a, the flow channel 132f in the sheathing member 132c extends and is opened toward the lateral surface opposite to the side, on which the negative electrode 105a and the positive electrode 105b are provided, at an intermediate position between the negative electrode 105a and the positive electrode 105b in the axial direction.

Though not particularly shown, similarly to the support 103a, the conducting wires 102a and 102b which pass through the electrostimulation lead 132 are respectively electrically connected to the negative electrode 105a and the positive electrode 105b.

The cylindrical balloon 136 is a member which urges the electrode portion 105 of the electrostimulation block portion 133 inserted into the superior vena cava $V_1$ toward the vein inner wall $V_s$, and a fluid filling portion 136c which communicates with the opening of the flow channel 132f in the support 133a is a saclike member which is formed of, for example, a thin film of silicone rubber.

The fluid filling portion 136c has a shape to be cylindrically swollen when the fluid supplied through the flow channel 132f is filled therein. In a state where the fluid is not filled, the fluid filling portion 136c has a thin cylindrical shape and can be appropriately folded and deformed.

With regard to the shape of the cylindrical balloon 136 when swollen, the diameter (outer diameter) of an outer circumferential surface 136a is set such that the electrode portion 105 comes into close contact with the vein inner wall $V_s$ in the superior vena cava $V_1$ in which the electrostimulation block portion 133 is placed.

The diameter (inner diameter) of an inner circumferential surface 136b is not particularly limited and is preferably as large as possible so as not to inhibit the blood flow. That is, the thickness of the fluid filling portion 136c when swollen is preferably small. When another lead is inserted in parallel to the electrostimulation lead 132, the inner diameter is set such that another lead passes therethrough.

The shape of the cylindrical balloon 136 when swollen depends on the diameter of the vein as an insertion target. For example, a thin cylindrical shape is preferably used which as an inner diameter of φ19 mm when the outer diameter is φ10 mm and an inner diameter of φ19 mm when the outer diameter is φ20 mm.

In this embodiment, the arrangement position of the cylindrical balloon 136 in the axial direction is set inside the negative electrode 105a and the positive electrode 105b.

According to such arrangement, even when the single cylindrical balloon 136 is provided, the negative electrode 105a and the positive electrode 105b can substantially press the vein inner wall $V_s$ equally. For this reason, it is possible to prevent the negative electrode 105a and the positive electrode 105b from floating from the vein inner wall $V_s$.

However, the cylindrical balloon 136 may be provided in a range so as to cover the negative electrode 105a and the positive electrode 105b in the axial direction, or the end portion on the base end side may be arranged closer to the base end compared to the positive electrode 105b.

A plurality of cylindrical balloons 136 may be arranged, for example, at the positions facing the negative electrode 105a and the positive electrode 105b, and the flow channel 132f may branch off and communicate with the fluid filling portion 136c.

As described above, in the electrostimulation system 131, the electrode urging member is constituted by a cylindrical balloon whose outer diameter is enlargeable and reducible through fluid pressure.

A convex portion which is engaged with the rotary member 107 is constituted by a member different from the electrode urging member.

According to the electrostimulation system 131, in a state where the fluid is not filled in the cylindrical balloon 136, in the same manner as in the first embodiment, the electrostimulation block insertion process can be performed. That is, the electrostimulation block portion 133 and the electrostimulation lead 132 are inserted into the superior vena cava $V_1$ through the rotary member 107. At this time, the cylindrical balloon 136 is folded inside the rotary member 107, thereby easy insertion is achieved.

Next, the electrostimulation block portion 133 extends from the leading end of the rotary member 107, and the normal saline solution is injected from the syringe connected to the syringe connection connector 132e. The normal saline solution is supplied to the fluid filling portion 136c of the cylindrical balloon 136 through the flow channel 132f, and the cylindrical balloon 136 is swollen in a cylindrical shape. At this time, the injection amount of the normal saline solution should be limited such that too much urging force toward the vein inner wall $V_s$ is not applied, so that the electrostimulation block portion 133 can go straight and rotate in the superior vena cava $V_1$.

The cylindrical balloon 136 is swollen in such a state, such that the cylindrical balloon 136 is arranged in a cylindrical shape along the vein inner wall $V_s$, and the flow of blood is not inhibited because the central portion thereof is opened.

Since the injection amount of the normal saline solution into the cylindrical balloon 136 is small, the cylindrical balloon 136 has softness and flexibility, and even when there is unevenness or meandering in the vein, can be smoothly inserted into the vein.

Next, the electrode alignment process is performed. In this process, as in the first embodiment, the position of the electrostimulation lead 132 is fixed, the rotary member 107 is moved in the axial direction, and the engagement grooves 107d are engaged with the cylindrical protrusions 133b of the support 133a. Thereafter, as in the first embodiment, the rotary member 107 is rotated while monitoring the electrocardiogram or the heart rate, such that the position of the electrostimulation block portion 133 in the circumferential direction is aligned in the vein inner wall $V_s$.

Thus, as shown in FIG. 16, the vagus nerve VN and the electrode portion 105 can be arranged to face each other with the vein sandwiched therebetween.

After the position of the electrostimulation block portion 133 in the circumferential direction is aligned, the normal saline solution is further injected from the syringe, such that the swollen amount of the cylindrical balloon 136 is maximized. Thus, the outer circumferential surface 136a of the cylindrical balloon 136 urges the vein inner wall $V_s$ and the lateral surface of the support 133a on the rear side of the electrode portion 105, the electrode portion 105 and the vein inner wall $V_s$ come into close contact with each other, and the position of the electrostimulation block portion 133 with respect to the vein inner wall $V_s$ is fixed. The rotary member 107 is withdrawn to the base end side and disengaged with the cylindrical protrusions 133b.

Since the syringe connection connector 132e has the check valve, even when the injection of the normal saline solution stops and the syringe is removed, the shape of the cylindrical balloon 136 is maintained.

Next, as in the first embodiment, if necessary, the rotary member 107 is removed, and the electrostimulation process is further performed.

According to this embodiment, the cylindrical balloon 136 having excellent flexibility is used so as to be easily aligned with respect to veins of various sizes or modified cross-sections. Since the cylindrical balloon 136 is excellent in softness, there is no case where vascular endothelium is damaged at the time of insertion or placement.

A metallic mesh structure which is used in a stent may be provided on the outer circumference of the cylindrical balloon 136. In this case, the position after the alignment in the vein can be more firmly stabilized.

Although in the above description, an example has been described where the electrostimulation block is provided at the leading end of the sheathed conducting wire member, the position of the electrostimulation block is not limited to the leading end and may be provided in the intermediate portion of the sheathed conducting wire member on the leading end side of the sheathed conducting wire member.

Although in the description of the first to third embodiments, an example has been described where the electrode urging member is constituted by an elastic member having an arc portion, the shape before deformation is not limited to the arc shape insofar as the electrode urging member is arranged in the circumferential direction of the vein, and urging can be done outwardly in the radial direction. For example, a curved shape which forms a portion of an ellipse, a parabola, a hyperbola, or the like may be used.

The shape of the electrode urging member in side view is not limited to the U shape, and may be, for example, a corrugated shape, an arc shape, a comb-teeth shape, or the like.

The electrode urging member is not limited to the linear elastic member, and may be an elastic member which comes into surface contact with the vein inner wall.

Although in the description of the fourth embodiment, an example has been described where the electrode urging member is a cylindrical balloon, the electrode urging member may have a shape, such as a C sectional shape.

Although in the description of the first embodiment or the like, an example has been described where the rotary member serves as an introducer having a check valve, the rotary member is not limited to an introducer insofar as the rotary member is arranged on the outer circumference of the sheathed conducting wire member and has a cylindrical shape with a base end portion extending outside the body, and an engagement mechanism rotating the electrostimulation block is provided in the vicinity of the leading end. For example, a guide sheath having no check valve may be used.

Although in the description of the third embodiment, an example has been described where the rotary member 127 is a solid shaft-like member, the rotary member which can pass through the sheathed conducting wire member may be a tubular member. For example, a tubular member with engagement grooves at the leading end may be used so as to be engaged with convex portions protruding toward the inner circumferential surface of the sheathed conducting wire member.

In this case, if a structure is made such that the hollow portion of the sheathed conducting wire member pass through the electrostimulation block, as in the second embodiment, the pacing lead and the like can pass through the hollow portion.

[Fifth Embodiment]

As a fifth embodiment of the present invention, an electrostimulation electrode assembly will be described which can be used in combination with the electrostimulation system according to each of the first to fourth embodiments of the invention.

Figure 17A:
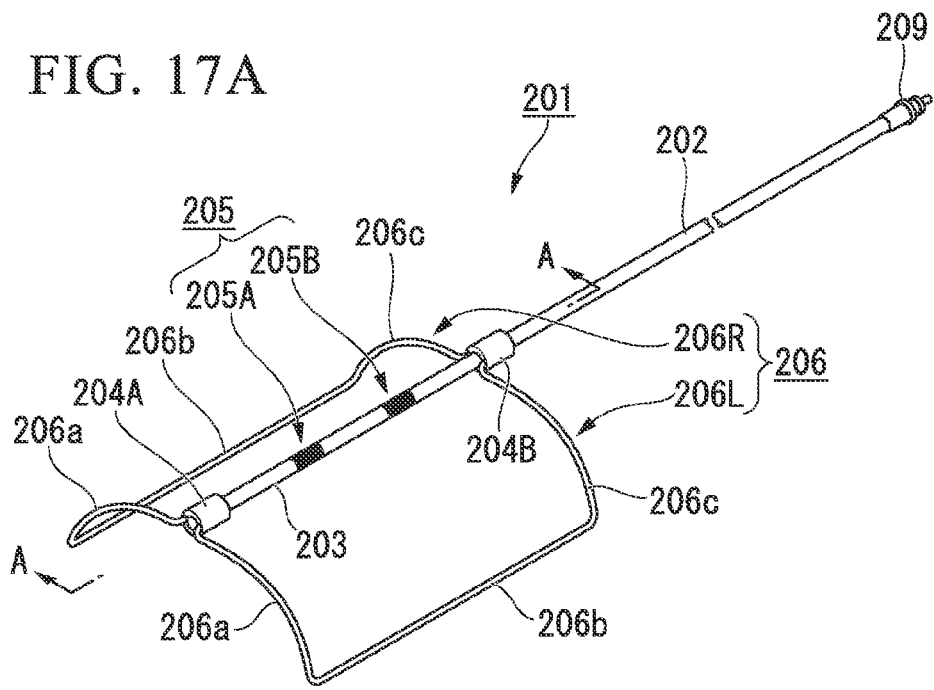
FIG. 17A is a schematic perspective view of an electrostimulation electrode assembly according to a fifth embodiment of the present invention.
Figure 17B:
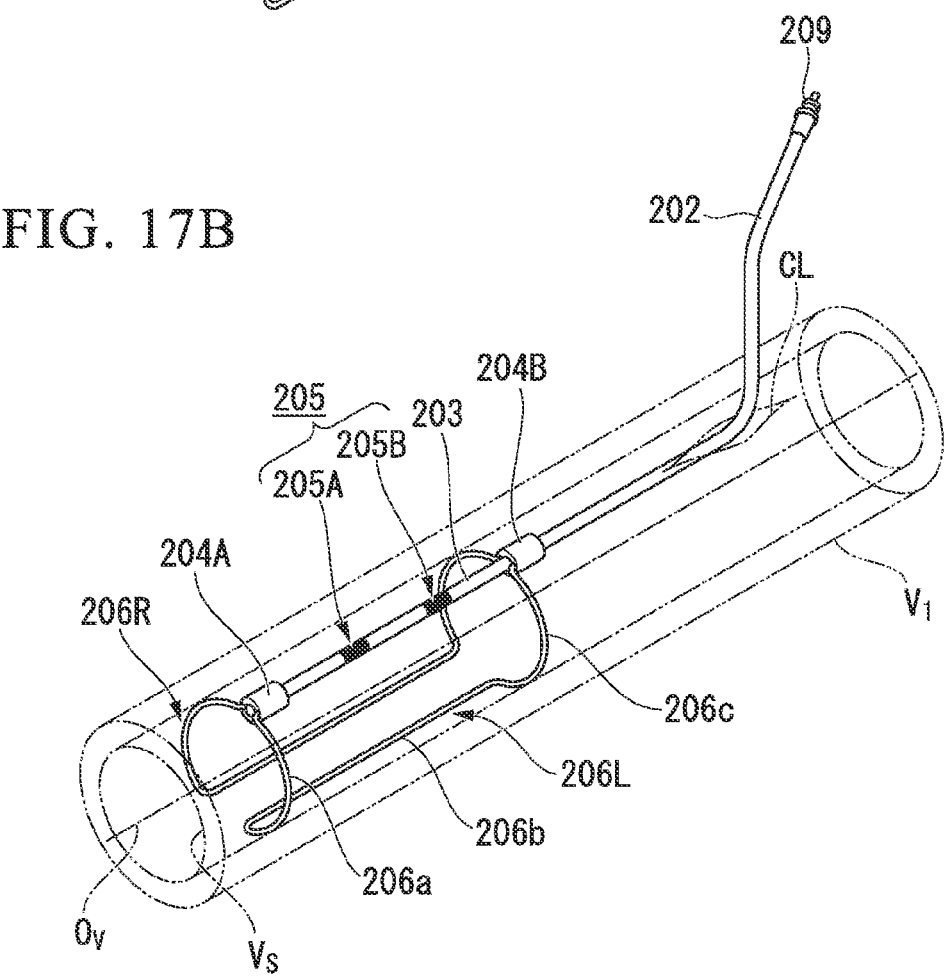
FIG. 17B is a schematic perspective view showing a state where the electrostimulation electrode assembly according to the fifth embodiment of the present invention is loaded in a vein.
Figure 18A:
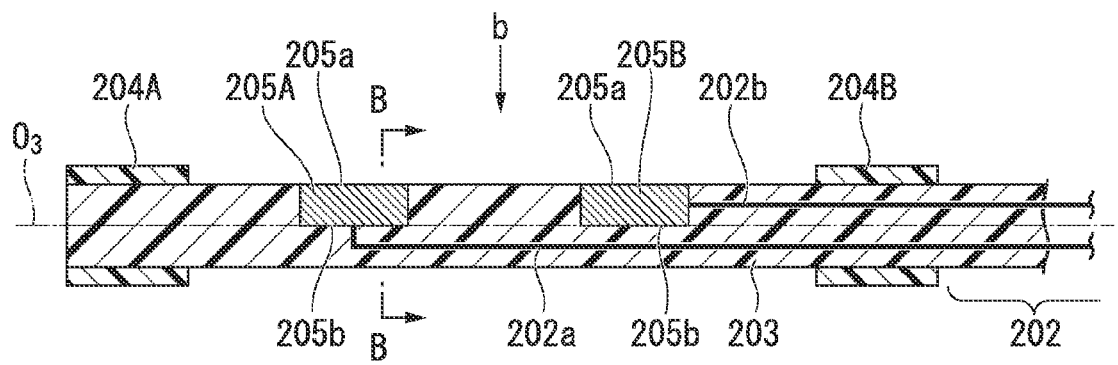
FIG. 18A is a sectional view taken along the line A-A of FIG. 17A.
Figure 18B:
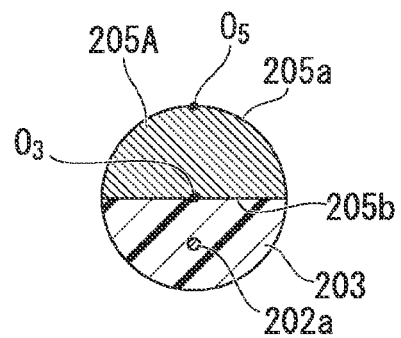
FIG. 18B is a sectional view taken along the line B-B of FIG. 18A.
Figure 18C:
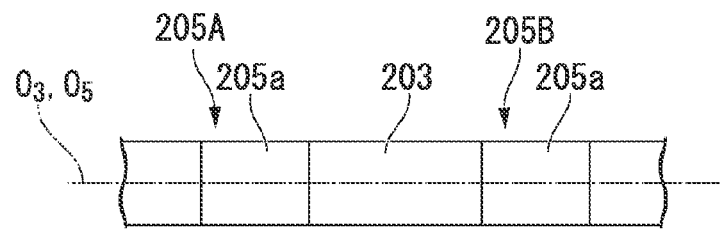
FIG. 18C is a diagram when viewed from a direction indicated by an arrow b of FIG. 18A.
Figure 19A:
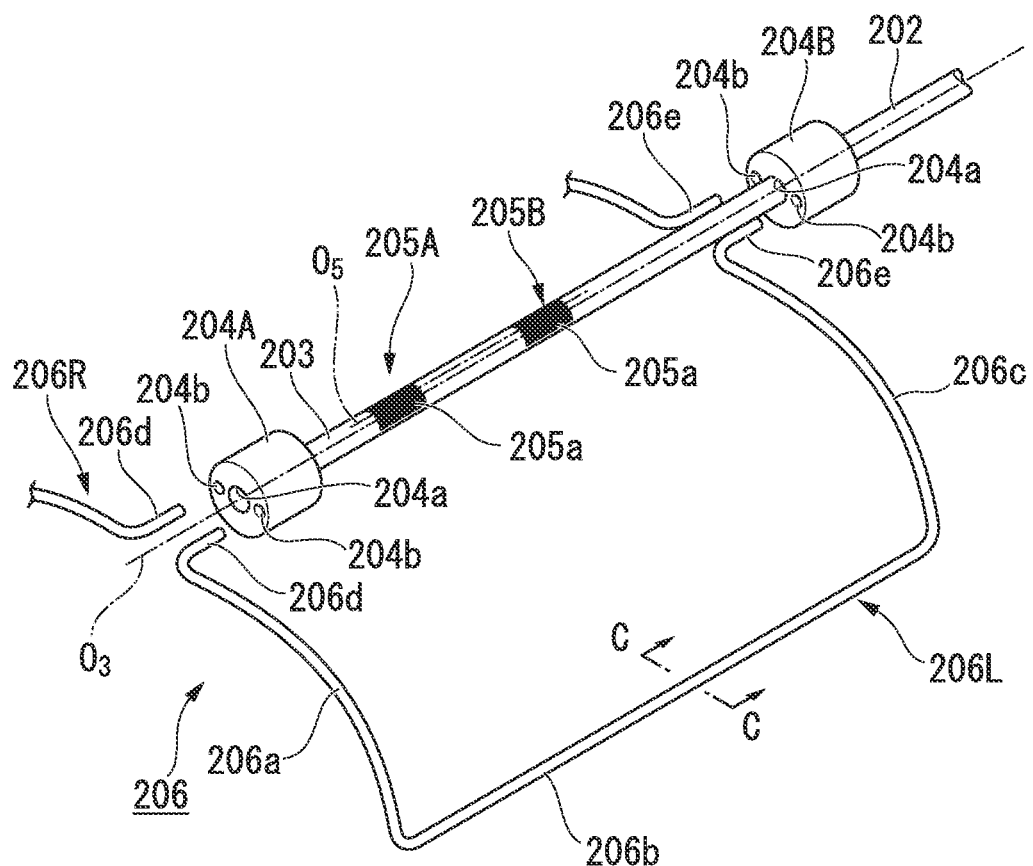
FIG. 19A is a schematic exploded perspective view showing a main part of the electrostimulation electrode assembly according to the fifth embodiment of the present invention.
Figure 19B:
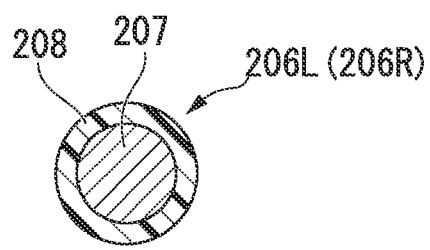
FIG. 19B is a sectional view taken along the line C-C of FIG. 19A.
Figure 20A:
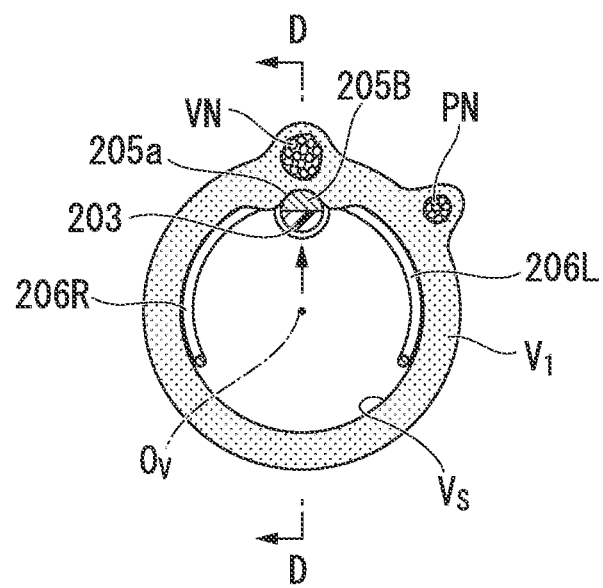
FIG. 20A is a schematic sectional view showing a state where the electrostimulation electrode assembly according to the fifth embodiment of the present invention is loaded in a superior vena cava.
Figure 20B:
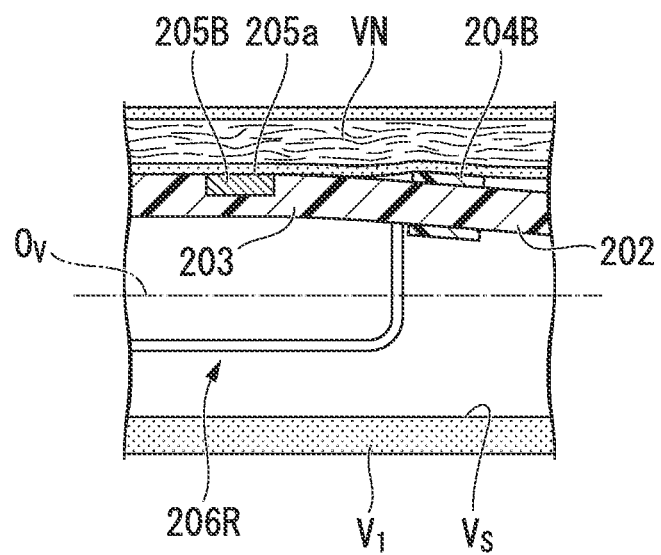
FIG. 20B is a sectional view taken along the line D-D of FIG. 20A.

FIG. 17A is a schematic perspective view of an electrostimulation electrode assembly according to a fifth embodiment of the present invention. FIG. 17B is a schematic perspective view showing a state where the electrostimulation electrode assembly according to the fifth embodiment of the present invention is loaded in a vein. FIG. 18A is a sectional view taken along the line A-A of FIG. 17A. FIG. 18B is a sectional view taken along the line B-B of FIG. 18A. FIG. 18C is a diagram when viewed from a direction indicated by an arrow b of FIG. 18A. FIG. 19A is a schematic exploded perspective view showing a main part of the electrostimulation electrode assembly according to the fifth embodiment of the present invention. FIG. 19B is a sectional view taken along the line C-C of FIG. 19A. FIG. 20A is a schematic sectional view showing a state where the electrostimulation electrode assembly according to the fifth embodiment of the present invention is loaded in a superior vena cava. FIG. 20B is a sectional view taken along the line D-D of FIG. 20A.

The drawings are schematic views, thus the shape or dimension is magnified (the same is applied to the following description).

As shown in FIGS. 17A, 18A, and 18B, an electrode stimulation lead 201 (electrostimulation electrode assembly) of this embodiment includes an electrode portion 205, a support 203 which supports the electrode portion 205 in a state where a portion of the electrode portion 205 is exposed as an exposed electrode surface 205a, conducting wires 202a and 202b (conducting wire member, see FIG. 18A) which are electrically connected to the electrode portion 205, a sheathing member 202 through which the conducting wires 202a and 202b pass, a connector 209 (terminal portion) which is electrically connected to the conducting wires 202a and 202b passing through the sheathing member 202, and an electrode urging member 206 which is fixed to the lateral surface of the support 203.

The electrode stimulation lead 201 indirectly applies electrical stimulus to a biological tissue, such as a nervous tissue, through the inner wall of the vein. The electrostimulation lead 201 is used to be connected to a stimulus generation device (electrostimulation device 1200 or the like) (not shown) through the connector 209 provided on the base end side. The stimulus generation device may be implanted inside the body or may be provided outside the body, and a heart pacemaker, an implanted defibrillation device, a nervous stimulation device, a pain relief device, an epilepsy treatment device, a muscle stimulation device, and the like may be an exemplary example.

The electrode stimulation lead 201 of the embodiment can be particularly preferably used in a treatment to apply electrical stimulus to a nervous tissue in the vicinity of the heart, for example, a vagus nerve or the like.

For this reason, as shown in FIG. 17B, the electrode stimulation lead 201 is used in a state where the support 203, the electrode urging member 206, the leading end portion of the sheathing member 202 connected to the support 203 are inserted into or implanted in the vein, for example, the superior vena cava $V_1$.

The electrode portion 205 is a metal portion which applies electrical stimulus through the inner wall of the vein, and as shown in FIGS. 18A and 18B, is constituted by an electrode pair of a negative electrode 205A (electrode) electrically connected to the conducting wire 202a inside the support 203 and a positive electrode 205B (electrode) electrically connected to the conducting wire 202b inside the support 203.

The material of the negative electrodes 205A and the positive electrode 205B is not particularly limited insofar as a metal has biocompatibility so as to be used in a state of being implanted in the biological body. Preferred examples of the material include noble metal materials having biocompatibility, such as a platinum-iridium alloy.

The shape of the negative electrode 205A is not particularly limited insofar as the exposed electrode surface 205a which is exposed from the support 203 can smoothly come into close contact with the vein inner wall $V_s$ and the shape can transmit sufficient electrostimulation energy to a nervous tissue or the like as a stimulation target in the vicinity of the vein inner wall $V_s$ through the exposed electrode surface 205a.

In this embodiment, the negative electrode 205A is constituted by a block member which has a shape obtained by bisecting a columnar member along the center line, and is provided in the support 203 so as to be exposed from the semi-cylindrical surface of the exposed electrode surface 205a. A fixed portion 205b on the rear side of the exposed electrode surface 205a is fixed in close contact with the support 203. The diameter of the exposed electrode surface 205a is the same as the outer diameter of the support 203 having a columnar shape.

The shape of the positive electrode 20513 is also not particularly limited insofar as the exposed electrode surface 205a which is exposed from the support 203 can smoothly come into close contact with the vein inner wall $V_s$ and the shape can transmit sufficient electrostimulation energy to a nervous tissue or the like as a stimulation target in the vicinity of the vein inner wall $V_s$ through the exposed electrode surface 205a.

In this embodiment, the positive electrode 205B is constituted by a block member having the same shape as the negative electrode 205A.

The positive electrode 205B is provided on the support 203 at a position distant from the negative electrode 205A toward the base end such that the exposed electrode surface 205a turns in the same direction as the negative electrode 205A. Similarly to the negative electrode 205A, a fixed portion 205b on the rear side of the exposed electrode surface 205a is fixed in close contact with the support 203.

For this reason, as shown in FIG. 18C, the exposed electrode surfaces 205a in plan view (when viewed from a direction indicated by an arrow b of FIG. 18A) are arrayed in a direction along the central axis $O_3$ of the support 203, and the center lines of the exposed electrode surfaces 205a are arrayed on a center line $O_5$ parallel to the central axis $O_3$.

The dimension of the negative electrode 205A and the positive electrode 205B can be appropriately set insofar as appropriate electrical stimulus can be applied from the vein inner wall $V_s$ to a nervous tissue in the vicinity of the vein inner wall $V_s$. As an example of specific dimension, when the outer diameter of the support 203 is φ2.0 mm, the length in the axial direction of each exposed electrode surface 205a is 2 mm, the diameter of the exposed electrode surface 205a is φ2.0 mm, and the gap (separation interval) in the axial direction between the negative electrode 205A and the positive electrode 205B is 5 mm.

The support 203 is a member which is pressed in close contact with the vein inner wall $V_s$ along with the exposed electrode surfaces 205a exposed from the surface when inserted inside the vein and placed, and is formed of a material having electrical insulation. The support 203 is preferably formed of a material having high biocompatibility so as to be implanted in the biological body for a long time. Silicone resin, polyurethane, and fluorine resin are exemplary examples thereof. Examples of fluorine resin include a tetrafluoroethylene-ethylene copolymer (ETFE), polytetrafluoroethylene (PTFE), and the like.

The surface of the support 203 is preferably subjected to thrombus preventing coating.

In this embodiment, the support 203 has a columnar outer shape having the same diameter as the outer diameter of each exposed electrode surface 205a of the electrode portion 205. An aperture shape in which the negative electrode 205A and the positive electrode 205B are provided is formed in the lateral surface of the intermediate portion in the axial direction. Two through holes through which the conducting wires 202a and 202b connected to the negative electrode 205A and the positive electrode 205B pass to the base end side under insulated condition are provided inside the support 203 along the axial direction.

For this reason, as shown in FIG. 18B, the sectional shape of the support 203 of this embodiment is a semicircular shape to be plane-symmetric to the negative electrode 205A or the like. As a result, the support 203 is provided in a shape to entirely cover the negative electrode 205A and the positive electrode 205B when viewed from the rear sides of the exposed electrode surfaces 205a.

As shown in FIGS. 19A and 19B, a leading end-side fixed portion 204A and a base end-side fixed portion 204B are fixed to the outer circumferential portions of the leading end portion and the base end portion of the support 203 to fix the electrode urging member 206.

The leading end-side fixed portion 204A and the base end-side fixed portion 204B are thin cylindrical members which have, in the intermediate portion, a support connection portion 204a as a through hole for fixing to the outer circumferential surface of the support 203, and in the lateral surface on the leading end side thereof, a hook fixing portion 204b is provided which is an aperture portion for inserting the electrode urging member 206 thereinto and fixing the electrode urging member 206. FIG. 19A is a schematic view, thus the dimension is magnified. Actually, a step between the leading end-side fixed portion 204A and the base end-side fixed portion 204B and the outer circumferential surface of the support 203 is configured to be sufficiently small so as to smoothly come into close contact with the vein inner wall $V_s$. For example, when the outer diameter of the support 203 is φ2.0 mm, the outer diameter of each of the leading end-side fixed portion 204A and the base end-side fixed portion 204B is preferably about φ2.0 mm.

As the material of the leading end-side fixed portion 204A and the base end-side fixed portion 204B, an appropriate resin material or a metal material having biocompatibility may be used.

As a method of fixing the leading end-side fixed portion 204A and the base end-side fixed portion 204B to the support 203, an appropriate fixing method, such as bonding, welding, pressing, or swaging, may be used depending on the materials.

The conducting wire 202a is a liner or coil-like conductor which electrically connects the terminal for a negative electrode of the connector 209 and the negative electrode 205A. The shape or material of the conducting wire 202a is not particularly limited insofar as the conducting wire 202a is resistant to bending in the vein into which the electrode stimulation lead 201 is inserted. In this embodiment, for example, a twisted wire made of a nickel-cobalt alloy is used.

The conducting wire 202b is a liner or coil-like conductor which electrically connects the terminal for a positive electrode of the connector 209 and the positive electrode 205B. With regard to the conducting wire 202b, the same shape and material as the conducting wire 202a may be used. In this embodiment, for example, a twisted wire made of a nickel-cobalt alloy is used.

The conducting wires 202a and 202b are guided toward the base end of the support 203 by the support 203 in a state of being insulated from each other, extend outside the support 203, and pass through the sheathing member 202, one end portion of which is connected to the base end portion of the support 203.

The sheathing member 202 is a member which has a linear shape to pass through the vein, and one end portion of which (the leading end portion of the sheathing member 202) is connected to the support 203, ensuring that the conducting wires 202a and 202b extending from the support 203 pass therethrough in an insulation state and guided to the other end portion thereof.

The outer shape in the sectional shape of the sheathing member 202 is not particularly limited insofar as the sheathing member 202 can pass through the vein, and a shape, such as a circular shape, an elliptical shape, an oval shape, or an approximate shape may be used. A lumen through which a catheter-like linear member passes may be provided.

In this embodiment, the sectional shape of the sheathing member 202 is a circular shape, and the outer diameter thereof is set to a diameter sufficiently smaller than the inner diameter of the vein so as not to inhibit the blood flow at the time of insertion into the vein. In this embodiment, the outer diameter is ϕ2.0 mm which is the same as the diameter of the support 203.

The sheathing member 202 is made of a material having electrical insulation, flexibility, and biocompatibility in the vein. For example, the same material as the support 203 may be used. The outer surface of the sheathing member 202 may be subjected to thrombus prevention coating.

Although the sheathing member 202 and the support 203 may be connected to the leading end side and the base end side as separate members, in this embodiment, the sheathing member 202 is molded as a single body with the support 203.

As shown in FIG. 17A, the connector 209 is provided in the other portion of the sheathing member 202. Though not particularly shown, the end portions of the conducting wires 202a and 202b having passed through the sheathing member 202 are respectively electrically connected to the terminal for a negative electrode and the terminal for a positive electrode of the connector 209.

As the connector type of the connector 209, an appropriate connector type may be used in accordance with the shape of the connection terminal of the stimulus generation device (not shown).

For example, when the stimulus generation device is provided inside body, an IS1 connector may be used. The IS1 connector includes a negative electrode, a positive electrode, and a rubber ring for maintaining the connection of the terminal for a negative electrode and the terminal for a positive electrode watertight.

When the stimulus generation device is provided outside the body, a waterproof connector may be used which includes a terminal for a negative electrode and a terminal for a positive electrode.

As shown in FIGS. 17A and 17B, the electrode urging member 206 urges the electrode portion 205 exposed from the support 203 toward the vein inner wall $V_s$. In this embodiment, the electrode urging member 206 is constituted by a fixing hook 206R and a fixing hook 206L.

In this embodiment, the fixing hooks 206R and 206L are formed by bending a linear elastic member in a U shape (angulated U shape) as a whole, and have arcuate arm portions 206a and 206c (curved portions or linear curved bodies) and a hook leading end portion 206b (leading end connection portion).

The fixing hooks 206R and 206L are formed and arranged so as to be plane-symmetric with respect to a plane including the center line $O_5$, which is common to the exposed electrode surfaces 205a of the negative electrode 205A and the positive electrode 205B arrayed in the axial direction of the support 203, and the central axis $O_3$ of the support 203. The fixing hook 206R is located on the right when viewed from the base end side of the support 203 to the leading end side in a state where the exposed electrode surface 205a of the electrode portion 205 turns upward, and the fixing hook 206L is located on the left side in the same manner.

As shown in FIG. 19B, the fixing hooks 206R and 206L of this embodiment are constituted by linear members which have a sheathed layer 208 formed on the outer circumferential surface of a linear elastic body 207 made of an appropriate elastic material to press the vein inner wall $V_s$ by elastic restoring force. In this embodiment, the cross-section of the linear elastic body 207 has a circular shape, and the sheathed layer 208 is formed concentrically.

The linear elastic body 207 is preferably formed of an elastic material such that the elastic material has flexibility to be a little folded at the time of insertion into the vein, and the shape which can urge the inner wall of the vein in the vein can be restored. Examples of the material includes superelastic alloy, such as nickel-titanium alloy, having shape reversibility to be easily elastically deformed by external force and to easily return to the state before deformation if external force is eliminated. In this embodiment, for example, a member which is substantially by molding a superelastic wire having a diameter ϕ0.3 mm made of a nickel-titanium-based alloy in a U shape.

As the sheathed layer 208, polyurethane tube coating or fluorine resin tube coating may be used. For this reason, the linear elastic body 207 does not come into direct contact with blood in the vein or the vein inner wall $V_s$. Polyurethane or fluorine resin has small frictional resistance against the vein inner wall $V_s$, allowing smooth sliding along the vein inner wall $V_s$.

Similarly to the sheathing member 202, the tube constituting the sheathed layer 208 is preferably subjected to thrombus prevention coating.

The sheathed layer 208 is not limited to tube coating, and may be formed by carrying out lubricating coating for the surface of the linear elastic body 207.

Hereinafter, unless particularly noted, the shape common to the fixing hooks 206R and 206L will be described on the basis of the shape in the natural state where no external force is applied.

The arcuate arm portion 206a protrudes from the leading end side compared to the negative electrode 205A in the lateral surface of the support 203, and is a curved portion which forms an arc to obliquely protrude outward in the radial direction and to be bent toward the opposite side to the direction in which each exposed electrode surface 205a of the electrode portion 205 is formed.

As shown in FIG. 17A, when each exposed electrode surface 205a of the electrode portion 205 turns upward, the arcuate arm portion 206a protrudes from the lower lateral surface compared to the electrode surface of the negative electrode 205A.

On the base end side in the protrusion direction of the arcuate arm portion 206a, as shown in FIG. 19A, a fixed end portion 206d is provided which is bent toward the base end along the axial direction of the support 203 so as to be inserted into and fixed to the hook fixing portion 204b of the leading end-side fixed portion 204A fixed to the support 203.

The average radius of curvature of the arcuate arm portion 206a is set to be greater than the radius of the inner wall portion of the vein as an insertion target, for example, the vein inner wall $V_s$ of the superior vena cava $V_1$.

The length of the arcuate arm portion 206a is equal to or greater than ¼ of the circumferential length of the vein inner wall $V_s$ at the position where the support 203 is provided. That is, the arcuate arm portion 206a of the fixing hook 206R and the arcuate arm portion 206a of the fixing hook 206L have a length equal to or greater than ¼ of the circumferential length of the vein inner wall $V_s$. Thus, the total length of the arcuate arm portions 206a of the fixing hooks 206R and 206L is equal to or greater than half of the circumferential length of the vein inner wall $V_s$. For this reason, if curvature is made along the vein inner wall $V_s$, a major arc shape is formed in the vein inner wall $V_s$.

The curved shape of the arcuate arm portion 206a is not limited to an arc shape, and an arc shape which forms a portion of an ellipse, a parabola, a hyperbola, or the like may be used insofar as the shape can be curved along the vein inner wall $V_s$.

The arcuate arm portion 206c protrudes from the base end side compared to the positive electrode 20513 in the lateral surface of the support 203, and is a curved portion which forms an arc to obliquely protrude in the same direction as the arcuate arm portion 206a outward in the radial direction and to be bent toward the opposite side to the direction in which each exposed electrode surface 205a of the electrode portion 205 is formed.

The protrusion position and the curved shape of the arcuate arm portion 206c in the circumferential direction of the lateral surface of the support 203 are set so as to overlap the arcuate arm portion 206a when viewed from the axial direction of the support 203.

As shown in FIG. 19A, on the base end side in the protrusion direction of the arcuate arm portion 206c, a fixed end portion 206e is provided which is bent toward the base end along the axial direction of the support 203 so as to be inserted into and fixed to the hook fixing portion 204b of the base end-side fixed portion 204B fixed to the support 203.

The hook leading end portion 206b is a linear portion which connects the leading ends of the arcuate arm portions 206a and 206c in the protrusion direction and extends along the axial direction of the support 203. Both end portions of the hook leading end portion 206b and the leading ends of the arcuate arm portions 206a and 206c in the protrusion direction form corner portions having an R shape. Thus, the fixing hooks 206R and 206L can come into smooth contact with and slide along the vein inner wall $V_s$.

The fixing hooks 206R and 206L are arrayed on the curved surface having a diameter greater than the vein inner wall $V_s$ laterally extending from the lateral surface of the support 203 in an assembled state where the fixed end portions 206d and 206e are fixed to the leading end-side fixed portion 204A and the base end-side fixed portion 204B. That is, a pair of arcuate arm portions 206a and a pair of arcuate arm portions 206c extend toward both lateral sides of the support 203 in an arc shape such that the direction in which the exposed electrode surface 205a is formed is made convex when viewed from the axial direction of the support 203. Each opening has a U shape to be connected to the lateral surface of the support 203 in plan view.

Thus, if the support 203 is inserted into the superior vena cava $V_1$, as shown in FIGS. 17B and 20A, the fixing hooks 206R and 206L are deformed in a direction in which the radius of curvature of the curved portion decreases to be elastically deformed along the vein inner wall $V_s$, and can urge the vein inner wall $V_s$ outward in the radial direction in accordance with the deformation amount.

Next, the action of the electrode stimulation lead 201 will be described in connection with, for example, an operation to apply electrical stimulus from the superior vena cava $V_1$ to the vagus nerve VN.

As shown in FIGS. 20A and 20B, the vagus nerve VN is in the vicinity of the superior vena cava $V_1$. For this reason, if each exposed electrode surface 205a of the electrode portion 205 is at the position facing the vagus nerve VN with the vein inner wall $V_s$ sandwiched therebetween, it is possible to indirectly apply electrical stimulus to the vagus nerve VN through the vein of the superior vena cava $V_1$.

First, as shown in FIG. 17B, the operator makes an incision on the skin in the cervical region to form an incision portion CL in the superior vena cava $V_1$.

Next, the operator inserts a tubular member (not shown), which is used to insert a catheter-like member, such as an introducer or a guide sheath, into the vein, into the incision portion CL, and the leading end of the tubular member is located in the vicinity of the vein inner wall $V_s$ parallel to the vagus nerve VN.

Next, the electrode stimulation lead 201 is inserted into the tubular member from the leading end side.

At this time, since the fixing hooks 206R and 206L are excellent in flexibility, if the support 203 is inserted into the tubular member, bending deformation occurs in a range of a gap between the support 203 and the tubular member, and the support is folded. The fixing hooks 206R and 206L are constituted by a linear member which is bent so as to have an R shape in the corner portions, do not have a shape to be caught by the inner circumferential surface of the tubular member. Thus, the fixing hooks 206R and 206L can smoothly slide in the axial direction in a folded state.

The operator further inserts the electrode stimulation lead 201 to protrude the electrode stimulation lead 201 from the leading end opening of the tubular member inward of the superior vena cava $V_1$. When the support 203 at the leading end emerges from the tubular member, external force from the tubular member is not applied to the folded fixing hooks 206R and 206L, such that the fixing hooks 206R and 206L try to return to the shape in the natural state.

The shape in the natural state of each of the fixing hooks 206R and 206L is greater than the inner diameter of the vein inner wall $V_s$ of the superior vena cava $V_1$. For this reason, as shown in FIGS. 17B and 20A, the fixing hooks 206R and 206L come into contact with the vein inner wall $V_s$ and urge the vein inner wall $V_s$ outward in the radial direction.

In the cross-section perpendicular to the central axis $O_v$ of the vein inner wall $V_s$, the arcuate arm portions 206a and 206c of the fixing hooks 206R and 206L have a length equal to or greater than half of the circumferential length of the vein inner wall $V_s$ in total, thereby reliably urging the electrode portion 205 in the support 203 outward in the radial direction. For this reason, the electrode portion 205 is urged toward the vein inner wall $V_s$ along with the support 203, and each exposed electrode surface 205a comes into close contact with the vein inner wall $V_s$.

At this time, since the radius of curvature of the exposed electrode surface 205a is smaller than the radius of curvature of the vein inner wall $V_s$, the exposed electrode surface 205a bites into and comes into close contact with the vein inner wall $V_s$.

In this way, the fixing hooks 206R, the support 203 including the electrode portion 205, and the fixing hook 206L are placed along the vein inner wall $V_s$. For this reason, the flow of blood in the superior vena cava $V_1$ is not easily inhibited. As a result, even when the electrode stimulation lead 201 is placed in the vein, it is possible to suppress the occurrence of thrombus in the vicinity of the electrode portion 205.

The position of the electrode portion 205 in the vein is maintained uniformly by urging force of the fixing hooks 206R and 206L.

Since the support 203 is provided to cover the entire electrode portion 205 from the rear side of the exposed electrode surface 205a, the exposed electrode surface 205a faces the vein inner wall $V_s$ and is exposed outward in the radial direction.

In this way, the electrode portion 205 is fixed in close contact with the vein inner wall $V_s$ in the vicinity of the vagus nerve VN. The tubular member which is used at the time of insertion is, for example, torn or the like and removed outside the vein or the body.

Next, the connector 209 is connected to the stimulus generation device to apply electrostimulation pulses set in advance from the stimulus generation device. Thus, electrostimulation energy emitted from the electrode portion 205 is emitted toward the vein inner wall $V_s$ and transmitted to the vagus nerve VN in the vicinity of the vein through the vein. As a result, the vagus nerve VN is indirectly electrically stimulated.

At this time, blood between the exposed electrode surface 205a and the vein inner wall $V_s$ is easily excluded by urging force from the electrode urging member 206. For this reason, electrostimulation energy from the exposed electrode surface 205a can be transmitted to the vein inner wall $V_s$ and applied to the vagus nerve VN outside the vein.

Since the exposed electrode surface 205a faces the vein inner wall $V_s$ and is exposed only outward in the radial direction, it is possible to reduce leakage of electrostimulation energy into blood. For this reason, stable electrostimulation can be carried out even at a low voltage.

In this embodiment, physical stress is not applied to a nervous tissue at all, and there is no case where the tissue is damaged due to ischemia.

Although a nervous tissue is very soft and easily damaged compared to other biological tissues, according to the electrode stimulation lead 201 of this embodiment, it is possible to reliably prevent such damage.

Since the electrode portion 205 is not in direct contact with the nervous tissue, there is no case where, when the electrode portion 205 is pressed, a foreign-body reaction occurs in the vicinity of the nervous tissue or fibrous capsule formation occurs. For this reason, biological impedance after the electrode portion 205 is placed is stabilized.

Thus, since the electrostimulation can be carried out without applying excessive electrostimulation energy, the possibility that the nervous tissue is damaged due to electrostimulation energy is significantly reduced.

Since the electrode portion 205 is stably supported in the vein by the electrode urging member 206, there is no case where the stimulation position of the electrode portion 205 is shifted.

As described above, according to the electrode stimulation lead 201 of this embodiment, the electrode can be placed in the superior vena cava by a transvenous approach. Thus, it is possible to carry out electrode placement in a very short time, to carry out electrode placement under local anesthesia, and to reduce a load imposed on a patient, compared to a case, for example, the electrode is placed in a nervous tissue by a trocar from a pleural cavity or a thoracotomy.

Next, first and second modifications of the electrostimulation electrode assembly of this embodiment will be described.

In these modification, only the shape of the electrode portion 205 which is used in the electrode stimulation lead 201 of the fifth embodiment and correspondingly the shape of the support 203 are changed. Hereinafter, a description will be provided focusing on the differences from the fifth embodiment.

Figure 21A:
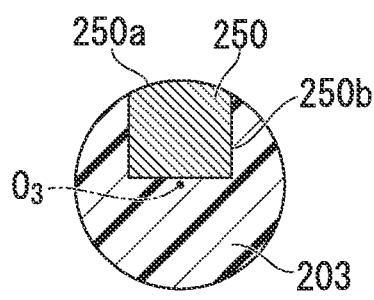
FIG. 21A is a schematic sectional view showing a first modification of the electrostimulation electrode assembly according to the fifth embodiment of the present invention.
Figure 21B:
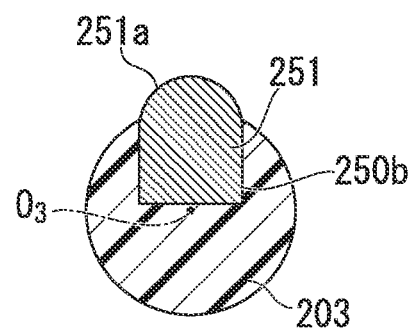
FIG. 21B is a schematic sectional view showing a second modification of the electrostimulation electrode assembly according to the fifth embodiment of the present invention.

FIGS. 21A and 21B are schematic sectional views showing first and second modifications of the electrostimulation electrode assembly according to the fifth embodiment of the invention.

[First Modification]

An electrode 250 of the first modification may be used in place of each of the negative electrode 205A and the positive electrode 205B of the electrode portion 205 of the fifth embodiment. As shown in FIG. 21A, the electrode 250 has a shape in which one surface of a rectangular parallelepiped projects in a cylindrical dome shape, and a fixed portion 250b which is the other rectangular parallelepiped portion is provided in the support 203 such that the projected cylindrical surface constitutes an exposed electrode surface 250a.

The diameter of the exposed electrode surface 250a is set to be the same as the outer diameter of the support 203.

For this reason, the exposed electrode surface 250a constitutes a circumferential surface in which a minor arc having a circumferential angle smaller than 180° extends in one direction.

Similarly to the exposed electrode surface 205a of the fifth embodiment, the exposed electrode surface 250a of this modification is configured such that entire electrode 250 is covered with the support 203 when viewed from the rear side of the exposed electrode surface 250a.

The exposure length of the exposed electrode surface 250a in the circumferential direction is shorter than the exposed electrode surface 205a. For this reason, even with weak urging force compared to the fifth embodiment, the exposed electrode surface 250a can be reliably brought into contact with the vein inner wall $V_s$.

The outer circumferential surface of the support 203 surrounding the outer circumference of the exposed electrode surface 250a can be reliably brought into contact with the vein inner wall $V_s$, making it possible to further reduce leakage of a current into blood at the time of electrostimulation.

In forming the exposed electrode surface 250a, the shape of the fixed portion 250b is not limited to a U shape which constitutes a portion of the rectangular parallelepiped. For example, the fixed portion 250b may have a V sectional shape. A reverse T shape or an arrow shape protruding downward in the drawing may be provided or an external screw shape or a multi-ring shape may be provided in the outer circumferential portion such that the withdrawal resistance outward in the radial direction with respect to the support 203 increases.

[Second Modification]

As shown in FIG. 21B, an electrode 251 of the second modification includes a cylindrical dome-shaped exposed electrode surface 251a having curvature smaller than the outer diameter of the support 203, in place of the exposed electrode surface 250a of the electrode 250 of the first modification. Hereinafter, a description will be provided focusing on the differences from the first modification.

Though not particularly shown, in the end portion of the exposed electrode surface 251a in the depth direction of the drawing, an inclined portion or an R shape is preferably provided to be smoothly connected to the outer circumferential surface of the support 203.

The inclined portion or the R shape may be provided by inclining or curving the end portion of the exposed electrode surface 251a or may be provided by raising a portion of the outer circumferential surface of the support 203 toward the exposed electrode surface 251a.

According to this modification, the exposed electrode surface 205a is formed as a convex surface having curvature smaller than the support 203, making it possible to further improve contact with the vein inner wall $V_s$.

Even when the electrode width in the circumferential direction is the same as the exposed electrode surface 250a of the first modification, it is possible to increase the electrode area.

[Third Modification]

Next, a third modification of the electrostimulation electrode assembly of this embodiment will be described.

Figure 22A:
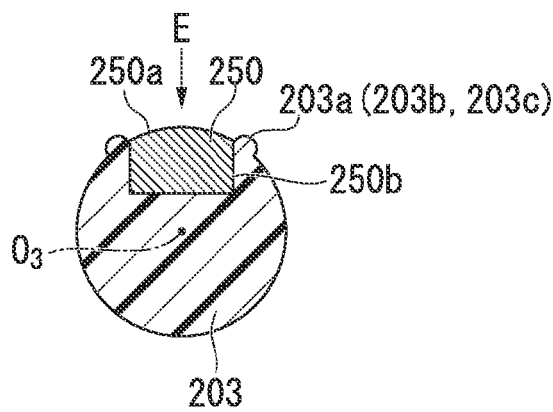
FIG. 22A is a schematic sectional view showing a third modification of the electrostimulation electrode assembly according to the fifth embodiment of the present invention.
Figure 22B:
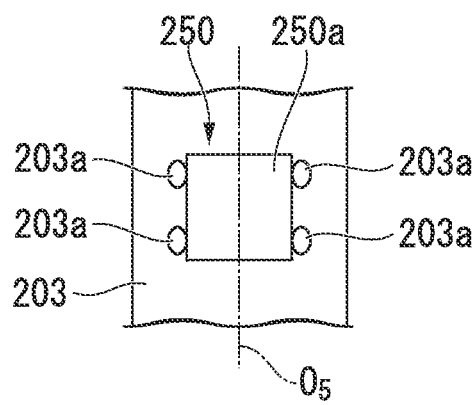
FIG. 22B is a diagram when viewed from a direction indicated by an arrow E of FIG. 22A.
Figure 22C:
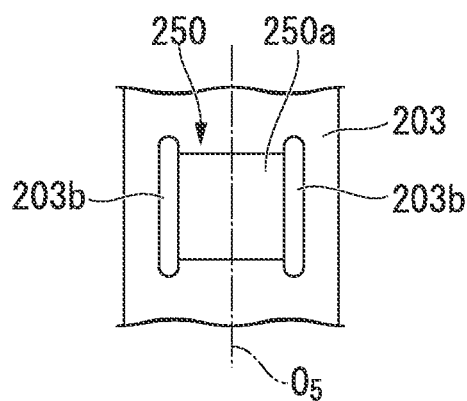
FIG. 22C is a diagram when viewed from the direction indicated by the arrow E of FIG. 22A.
Figure 22D:
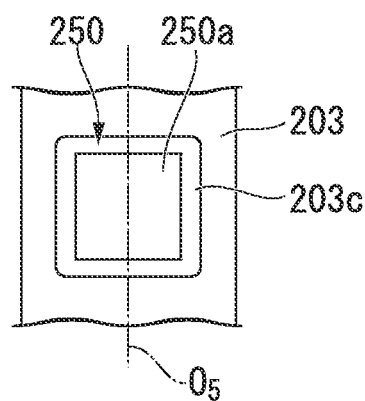
FIG. 22D is a diagram when viewed from the direction indicated by the arrow E of FIG. 22A.

FIG. 22A is a schematic sectional view showing a third modification of the electrostimulation electrode assembly according to the fifth embodiment of the invention. FIGS. 22B, 22C, and 22D are diagrams when viewed from a direction indicated by an arrow E of FIG. 22A.

In this modification, as shown in FIGS. 22A and 22B, an electrical insulating protrusion portion 203a is provided in the outer circumferential portion of the exposed electrode surface 250a of the first modification so as to protrude in an elliptical dome shape or a spherical shape from the surface of the support 203 outward in the radial direction. Hereinafter, a description will be provided focusing on the difference from the first modification.

The protrusion portion 203a is preferably formed as a single body with the support 203.

For example, FIG. 22B shows a case where the protrusion portions 203a are provided at four places in total by two places in the axial direction along the outline in the circumferential direction of the exposed electrode surface 250a. However, the number of protrusion portions 203a or the arrangement positions are not particularly limited. For example, the protrusion portion may be provided in the vicinity of the end surface in the axial direction of the exposed electrode surface 250a.

According to this modification, the protrusion portion 203a comes into contact with the vein inner wall $V_s$, making it possible to further stabilize the position of the electrode 250 with respect to the vein inner wall $V_s$.

The protrusion portion 203a protrudes outwardly in the radial direction compared to the exposed electrode surface 250a in the vicinity of the outer edge portion of the exposed electrode surface 250a, thus the protrusion portion 203a becomes a wall portion having electrical insulation with respect to the outer edge portion of the exposed electrode surface 250a. For this reason, the protrusion portion 203a has a function of reducing leaking of a current at the time of electrostimulation.

In this modification, in order to further increase the current leakage prevention effect, like a linear protrusion 203b and a revolving protrusion 203c shown in FIGS. 22B and 22C, a linear protrusion may be provided to extend along the outer edge portion of the exposed electrode surface 250a.

The linear protrusion 203b is a linear protrusion portion which extends in parallel to the outer edge portions on both sides of the exposed electrode surface 250a in the circumferential direction. In this case, it becomes easier to prevent misalignment of the exposed electrode surface 250a in the circumferential direction, making it possible to further reduce current leakage in the circumferential direction.

The revolving protrusion 203c is a linear protrusion portion which is provided to surround the exposed electrode surface 250a along the whole circumference of the outer edge portion of the exposed electrode surface 250a. In this case, it becomes easier to prevent misalignment of the exposed electrode surface 250a in the circumferential direction and the axial direction, making it possible to reduce current leakage toward the whole circumference of the exposed electrode surface 250a.

[Fourth Modification]

Next, a fourth modification of the electrostimulation electrode assembly of this embodiment will be described.

Figure 23:
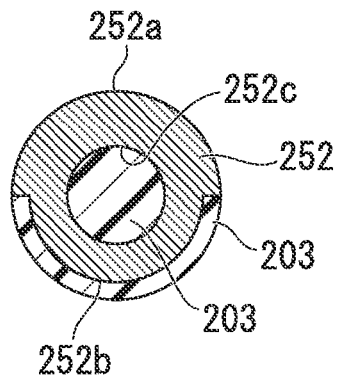
FIG. 23 is a schematic sectional view showing a fourth modification of the electrostimulation electrode assembly according to the fifth embodiment of the present invention.

FIG. 23 is a schematic sectional view showing a fourth modification of the electrostimulation electrode assembly according to the fifth embodiment of the invention.

An electrode 252 of this modification may be used in place of each of the negative electrode 205A and the positive electrode 205B of the electrode portion 205 of the fifth embodiment. As shown in FIG. 23, the electrode 252 is a substantially cylindrical member which has a through hole 252c in the center portion thereof. In the outer circumferential surface of the electrode 252, an exposed electrode surface 252a having the same semi-cylindrical shape as the exposed electrode surface 205a and an outer circumference fixed portion 252b, which is constituted by a semi-cylindrical surface having a diameter smaller than the exposed electrode surface 252a are provided. Hereinafter, a description will be provided focusing on the differences from the fifth embodiment.

The outer circumference fixed portion 252b is covered with the support 203. For this reason, the electrode 252 is apparently the same as negative electrode 205A and the positive electrode 205B of the fifth embodiment.

In this modification, since the electrode 252 is molded as a single body with the support 203, the material of the support 203 is filled in the through hole 252c, such that the electrode 252 is firmly fixed to the support 203.

However, the electrode 252 may be fixed to the support 203 by the outer circumference fixed portion 252b and the through hole 252c may be made hollow. When a coil-like conducting wire is used as the conducting wire 202a or the like, the through hole 252c may be used as a conducting wire connection portion with which the coil-like conducting wire is internally engaged for connection.

[Fifth Modification]

Next, a fifth modification of the electrostimulation electrode assembly of this embodiment will be described.

Figure 24A:
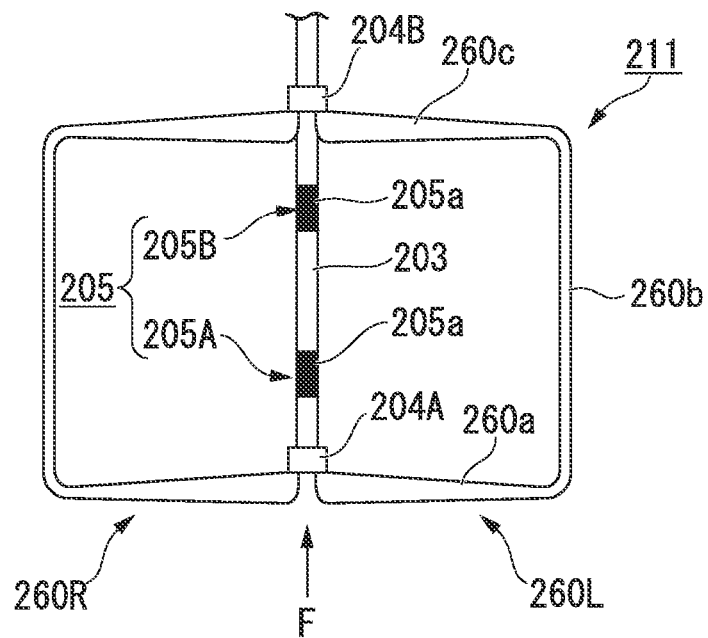
FIG. 24A is a schematic plan view showing a fifth modification of the electrostimulation electrode assembly according to the fifth embodiment of the present invention.
Figure 24B:
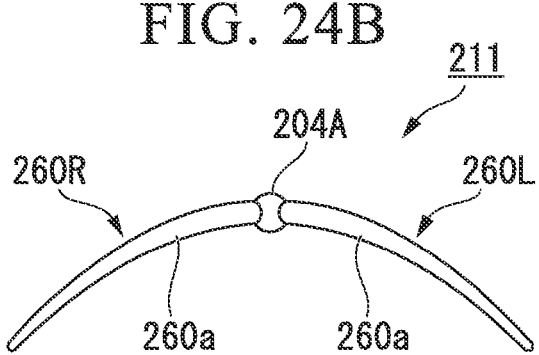
FIG. 24B is a diagram when viewed from a direction indicated by an arrow F of FIG. 24A.

FIG. 24A is a schematic plan view showing a fifth modification of the electrostimulation electrode assembly according to the fifth embodiment of the present invention. FIG. 24B is a diagram when viewed from a direction indicated by an arrow F of FIG. 24A.

As shown in FIGS. 24A and 24B, an electrode stimulation lead 211 (electrostimulation electrode assembly) of this modification includes an electrode urging member 260, in place of the electrode urging member 206 of the electrode stimulation lead 201 of the fifth embodiment. Hereinafter, a description will be provided focusing on the differences from the fifth embodiment.

The electrode urging member 260 is constituted by fixing hooks 260R and 260L which are linear members bent along the axis lines similarly to the fixing hooks 206R and 206L of the fifth embodiment, and the wire diameter of the fixing hooks 260R and 260L in the axial direction is changed.

That is, the fixing hook 260R (260L) includes an arcuate arm portion 260a with a gradually decreasing wire diameter from the base end portion fixed to the leading end-side fixed portion 204A in the protrusion direction toward the leading end in the protrusion direction, in place of the arcuate arm portion 206a. The fixing hook 260R (260L) also includes an arcuate arm portion 260c which a gradually decreasing wire diameter from the base end portion fixed to the base end-side fixed portion 204B in the protrusion direction toward the leading end in the protrusion direction, in place of the arcuate arm portion 206c.

The leading end portions of the arcuate arm portions 260a and 260c in the protrusion direction are connected to each other by a linear hook leading end portion 260b which extends along the axial direction of the support 203, in place of the hook leading end portion 206b.

The fixing hooks 260R and 260L may be manufactured by a molded product of a superelastic wire or a molded product made of the same resin material as the support 203.

According to this modification, urging force toward the vein inner wall $V_s$ can be adjusted by appropriately changing the wire diameter of the fixing hooks 260R and 260L. For example, a bias of pressing force in the circumferential direction of the vein inner wall $V_s$ can be reduced or a uniform pressure distribution can be achieved. A shape in which the blood flow is not easily inhibited may be obtained by reducing the diameter of a portion which does not contribute to an urging force.

[Sixth Modification]

Next, a sixth modification of the electrostimulation electrode assembly of this embodiment will be described.

Figure 25:
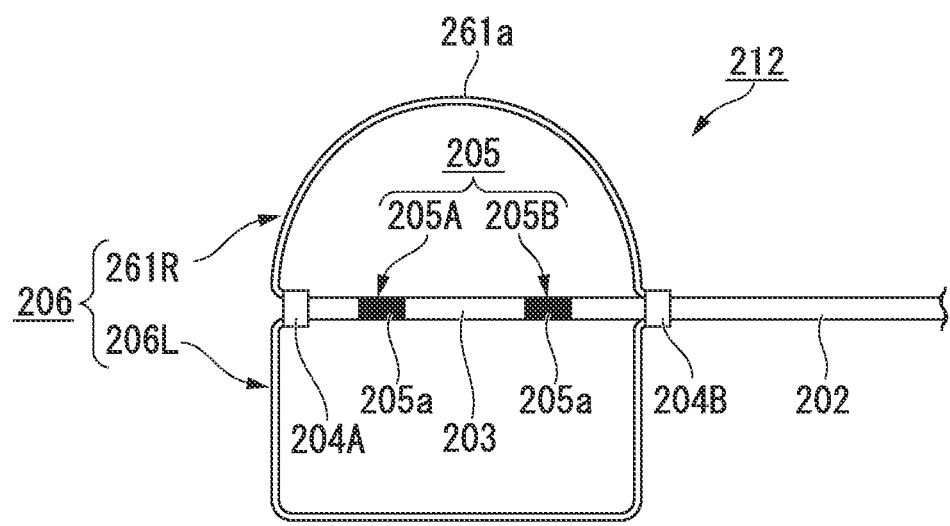
FIG. 25 is a schematic plan view showing a sixth modification of the electrostimulation electrode assembly according to the fifth embodiment of the present invention.

FIG. 25 is a schematic plan view showing a sixth modification of the electrostimulation electrode assembly according to the fifth embodiment of the present invention.

As shown in FIG. 25, an electrode stimulation lead 212 (electrostimulation electrode assembly) of this modification includes an asymmetrical electrode urging member 261 (electrode urging member), in place of the electrode urging member 206 of the electrode stimulation lead 201 of the fifth embodiment. Hereinafter, a description will be provided focusing on the differences from the fifth embodiment.

The asymmetrical electrode urging member 261 includes a U-shaped fixing hook 261R, in place of the fixing hook 206R of the fifth embodiment.

The U-shaped fixing hook 261R has a curved portion 261a which projects in a U shape from the leading end-side fixed portion 204A toward the base end-side fixed portion 204B in plan view and is curved in the same arc shape as the fixing hook 206R, in place of the arcuate arm portion 206a, the hook leading end portion 206b, and the arcuate arm portion 206c of the fixing hook 206R.

With this configuration, the shape of the asymmetrical electrode urging member 261 when viewed from the axial direction of the support 203 is a bilaterally symmetrical arc shape, and the shape in plan view is bilaterally asymmetrical with the support 203 sandwiched therebetween.

According to this modification, since the asymmetric electrode urging member 261 is provided, for example, in observing the electrode stimulation lead 212 inserted into the vein by using, for example, a two-dimensional image of an X-ray camera or the like, with the asymmetry of the asymmetrical electrode urging member 261, it becomes easy to recognize the arrangement, movement direction, and the like of the support 203 or the electrode portion 205.

[Seventh Modification]

Next, a seventh modification of the electrostimulation electrode assembly of this embodiment will be described.

Figure 26A:
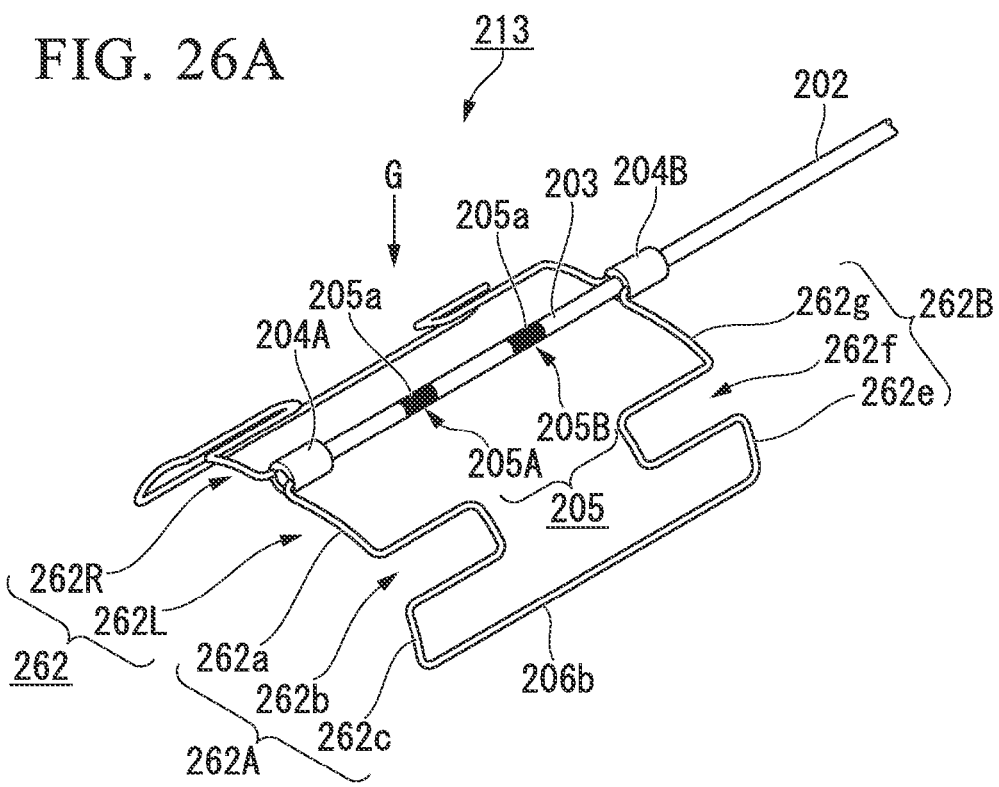
FIG. 26A is a schematic perspective view showing a seventh modification of the electrostimulation electrode assembly according to the fifth embodiment of the present invention.
Figure 26B:
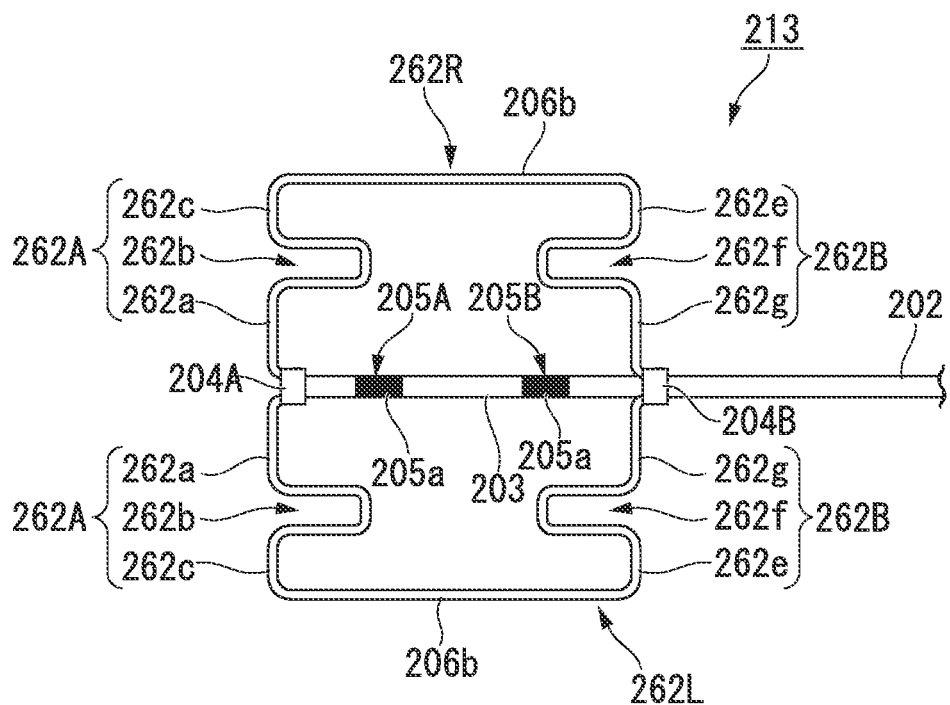
FIG. 26B is a plan view when viewed from a direction indicated by an arrow G of FIG. 26A.

FIG. 26A is a schematic perspective view showing a seventh modification of the electrostimulation electrode assembly according to the fifth embodiment of the present invention. FIG. 26B is a plan view when viewed from a direction indicated by an arrow G of FIG. 26A.

As shown in FIGS. 26A and 26B, an electrode stimulation lead 213 (electrostimulation electrode assembly) of this modification includes an electrode urging member 262, in place of the electrode urging member 206 of the electrode stimulation lead 201 of the fifth embodiment. Hereinafter, a description will be provided focusing on the differences from the fifth embodiment.

The electrode urging member 262 includes fixing hooks 262R and 262L having a shape to be plane-symmetric, in place of the fixing hooks 206R and 206L of the fifth embodiment.

The fixing hook 262R (262L) includes curved arm portions 262A and 262C, in place of the arcuate arm portions 206a and 206c of the fixing hook 206R (206L).

The curved arm portion 262A is a linear portion which has a bent portion 262b bent in a angulated U shape or a U shape toward the base end of the support 203 in the intermediate portion of the arcuate arm portion 206a in the protrusion direction. Thus, the arcuate arm portion 206a is divided into an arcuate portion 262a (curved portion) which is connected to the leading end-side fixed portion 204A and one end portion of the bent portion 262b and an arcuate portion 262c (curved portion) which is connected to the other end portion of the bent portion 262b.

The curved arm portion 262C is a linear portion which has a bent portion 262f bent in a U shape toward the leading end of the support 203 in the intermediate portion of the arcuate arm portion 206c in the protrusion direction. Thus, the arcuate arm portion 206c is divided into an arcuate portion 262g (curved portion) which is connected to the base end-side fixed portion 204B and one end portion of the bent portion 262f and an arcuate portion 262e (curved portion) which is connected to the other end portion of the bent portion 262b.

In this modification, the bent portions 262b and 262f are provided at positions facing each other along the axial direction of the support 203. The bent portions 262b and 262f are curved so as to overlap the arc shapes of the arcuate arm portions 206a and 206c when viewed from the axial direction of the support 203. For this reason, when curved in the vein, the bent portions 262b and 262f entirely come into contact with the vein inner wall $V_s$.

According to this modification, the arcuate portions 262a and 262c of the curved arm portion 262A are arrayed on the axis of the same arc shape in the natural state but are connected to each other through the bent portion 262b, such that, if external force is applied to the hook leading end portion 206b and deflective deformation occurs, deformation is easily made by torsional deformation of the bent portion 262b. For this reason, when the same external force is applied to the hook leading end portion 206b, the deformation amount increases compared to the beam-like arcuate arm portion 206a extending in an arc shape.

The curved arm portion 262A has small elastic restoring force compared to the arcuate arm portion 206a, such that urging force toward the vein inner wall $V_s$ is reduced.

The same is applied to the curved arm portion 262C.

As described above, according to this modification, urging force of the electrode urging member toward the vein inner wall $V_s$ can be changed without changing the wire diameter of a linear elastic member and without changing the circumferential length of a protruding arcuate portion.

Since the bent portions 262b and 262f of the fixing hooks 262R and 262L entirely come into contact with the vein inner wall $V_s$, urging force of the fixing hooks 262R and 262L is two-dimensionally dispersed on the vein inner wall $V_s$. The contact between the fixing hooks 262R and 262L and the vein inner wall $V_s$ is improved, and urging force toward the vein inner wall $V_s$ is dispersed. For this reason, excessive urging force toward the vein inner wall $V_s$ is not easily generated.

In this modification, since the bent portions 262b and 262f are provided in the intermediate portions of the curved arm portions 262A and 262B, when the fixing hooks 262R and 262L are folded in the tubular member at the time of insertion into the vein, the curved arm portions 262A and 262B are easily bending-deformed in the bent portions 262b and 262f. For this reason, accommodation in the tubular member is facilitated.

[Eighth Modification]

Next, an eighth modification of the electrostimulation electrode assembly of this embodiment will be described.

Figure 27A:
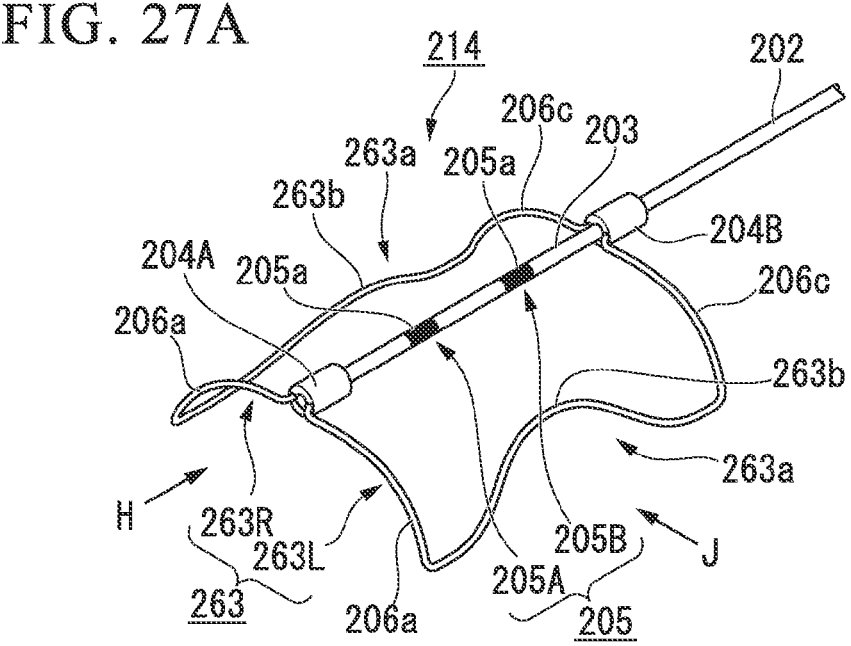
FIG. 27A is a schematic perspective view showing an eighth modification of the electrostimulation electrode assembly according to the fifth embodiment of the present invention.
Figure 27B:
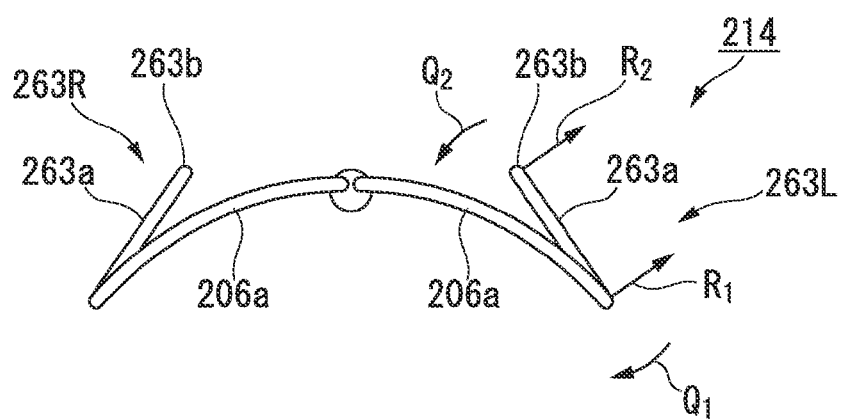
FIG. 27B is a side view when viewed from a direction indicated by an arrow H of FIG. 27A.
Figure 27C:
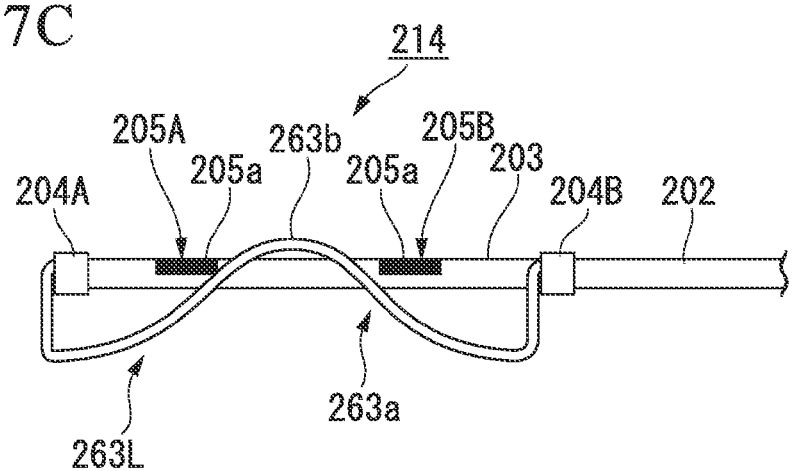
FIG. 27C is a side view when viewed from a direction indicated by an arrow J of FIG. 27A.

FIG. 27A is a schematic perspective view showing an eighth modification of the electrostimulation electrode assembly according to the fifth embodiment of the present invention. FIG. 27B is a side view when viewed from a direction indicated by an arrow H of FIG. 27A. FIG. 27C is a side view when viewed from a direction indicated by an arrow J of FIG. 27A.

As shown in FIGS. 27A, 27B, and 27C, an electrode stimulation lead 214 (electrostimulation electrode assembly) of this modification includes an electrode urging member 263, in place of the electrode urging member 206 of the electrode stimulation lead 201 of the fifth embodiment. Hereinafter, a description will be provided focusing on the differences from the fifth embodiment.

The electrode urging member 263 includes fixing books 263R and 263L having a shape to be plane-symmetric, in place of the fixing hooks 206R and 206L of the fifth embodiment.

The fixing hook 263R (263L) includes a leading end connection portion 263a, in place of the hook leading end portion 206b of the fixing hook 206R (206L).

As shown in FIG. 27B, the leading end connection portion 263a has a shape which is bent so as to protrude outward in the radial direction from a cylindrical curved surface in which the arcuate arm portions 206a and 206c as curved portions are arrayed.

In this modification, for example, as shown in FIG. 27B, the leading end connection portion 263a is curved in a chevron shape in a direction of approaching the support 203 between the connection portions to the arcuate arm portions 206a and 206c, and a bent portion 263b is formed at the vertex of the chevron shape. When viewed from the axial direction of the support 203, the bent portion 263b protrudes outward in the radial direction from the curved surface in which the arcuate arm portions 206a and 206c are arrayed.

The fixing hook 263R (263L) is constituted by a linear portion which is substantially bent in an M shape.

According to this modification, when the fixing hook 263R (263L) comes into contact with the vein inner wall $V_s$, as shown in FIG. 27B, in the leading end portions of the arcuate arm portions 206a and 206c in the protrusion direction, that is, in the connection portions to the bent portion 263b, external force is applied from the vein inner wall $V_s$ in a direction indicated by an arrow $Q_1$ to cause deformation, and reactive force $R_1$ is applied to the vein inner wall $V_s$.

Meanwhile, before coming into contact with the intermediate portions of the arcuate arm portions 206a and the 206c, the vein inner wall $V_s$ comes into contact with the bent portion 263b of the leading end connection portion 263a, such that external force is applied from the vein inner wall $V_s$ in a direction indicated by an arrow $Q_2$ to cause deformation, and reactive force $R_2$ is applied to the vein inner wall $V_s$.

For this reason, although in the hook leading end portion 206b of the fifth embodiment, reactive force by deflection of the arcuate arm portions 206a and 206c is merely transmitted, with regard to the leading end connection portion 263a of this modification, reactive force $R_2$ by deformation of the leading end connection portion 263a is added to urging force which is applied to the vein inner wall $V_s$.

For this reason, it is possible to improve urging force compared to the fifth embodiment.

The fixing hook 263R (263L) comes into contact with the vein inner wall $V_s$ in an M shape, making it possible to improve contact with the vein inner wall $V_s$.

In this modification, since the bent portion 263b is provided in the intermediate portion of the leading end connection portion 263a, when the fixing hooks 263R and 263L are folded in the tubular member at the time of insertion into the vein, the leading end connection portion 263a is easily bending-deformed in the bent portion 263b. For this reason, accommodation in the tubular member is facilitated.

[Ninth Modification]

Next, a ninth modification of the electrostimulation electrode assembly of this embodiment will be described.

Figure 28:
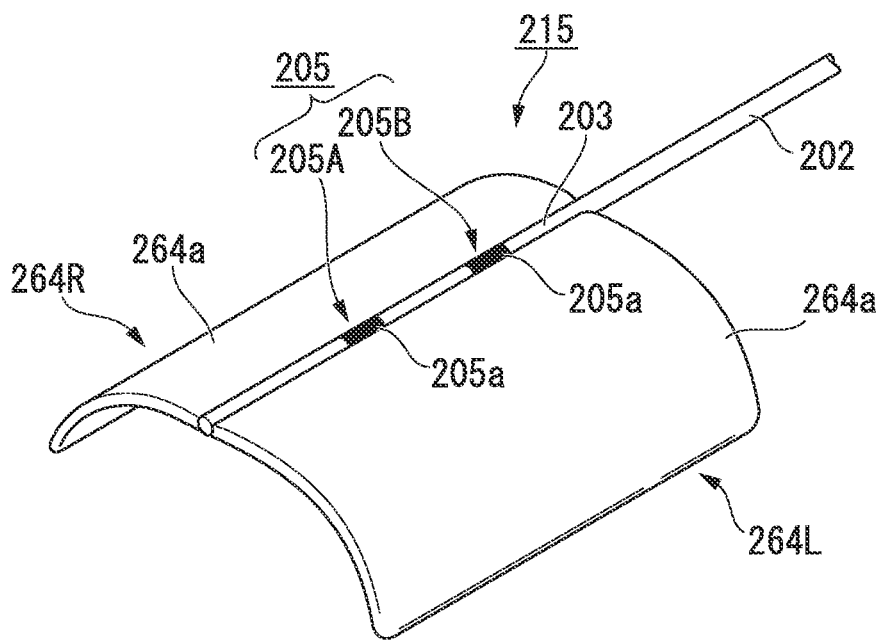
FIG. 28 is a schematic perspective view showing a ninth modification of the electrostimulation electrode assembly according to the fifth embodiment of the present invention.

FIG. 28 is a schematic perspective view showing a ninth modification of the electrostimulation electrode assembly according to the fifth embodiment of the present invention.

As shown in FIG. 28, an electrode stimulation lead 215 (electrostimulation electrode assembly) of this modification includes an electrode urging member 264, in place of the electrode urging member 206 of the electrode stimulation lead 201 of the fifth embodiment. Hereinafter, a description will be provided focusing on the differences from the fifth embodiment.

The electrode urging member 264 includes fixing hooks 264R and 264L having a shape to be plane-symmetric, in place of the fixing hooks 206R and 206L of the first embodiment.

The fixing hook 264R (264L) includes a plate-shaped curved hook 264a which is substantially curved in a cylindrical shape. The sectional shape of the plate-shaped curved hook 264a coincides with the shape which is drawn by the axis of each of the arcuate arm portion 206a, the hook leading end portion 206b, and the arcuate arm portion 206c of the fixing hook 206R (206L). That is, each plate-shaped curved hook 264a is a curved plate which extends from the lateral surface of the support 203 toward the lateral direction with the negative electrode 205A and the positive electrode 205B sandwiched therebetween, and the shape when viewed from the axial direction of the support 203 is an arch shape which is curved from the exposed electrode surface 205a of each of the negative electrode 205A and the positive electrode 20513 toward the rear side of the exposed electrode surface 205a.

The plate-shaped curved hook 264a may be manufactured by, for example, a molded product of a superelastic alloy or a molded product made of the same resin material as the support 203. When a resin material is used, the plate-shaped curved hook 264a may be molded as a single body with the support 203.

In this modification, each plate-shaped curved hook 264a is rolled and arranged along the lateral surface of the support 203 so as to be inserted into the vein through the tubular member. After insertion, when protruding from the tubular member, each plate-shaped curved hook 264a is restored to the shape before rolling and presses the vein inner wall $V_s$ outward in the radial direction, such that the vein inner wall $V_s$ is urged and the position of the electrode portion 205 is fixed.

According to this modification, the fixing hooks 264R and 264L come into plane contact with the vein inner wall $V_s$, such that the position of the electrode portion 205 is fixed. Thus, the contact to the vein inner wall $V_s$ is improved, and urging force toward the vein inner wall $V_s$ is dispersed. For this reason, excessive urging force toward the vein inner wall $V_s$ is not easily generated.

[Tenth Modification]

Next, a tenth modification of the electrostimulation electrode assembly of this embodiment will be described.

Figure 29:
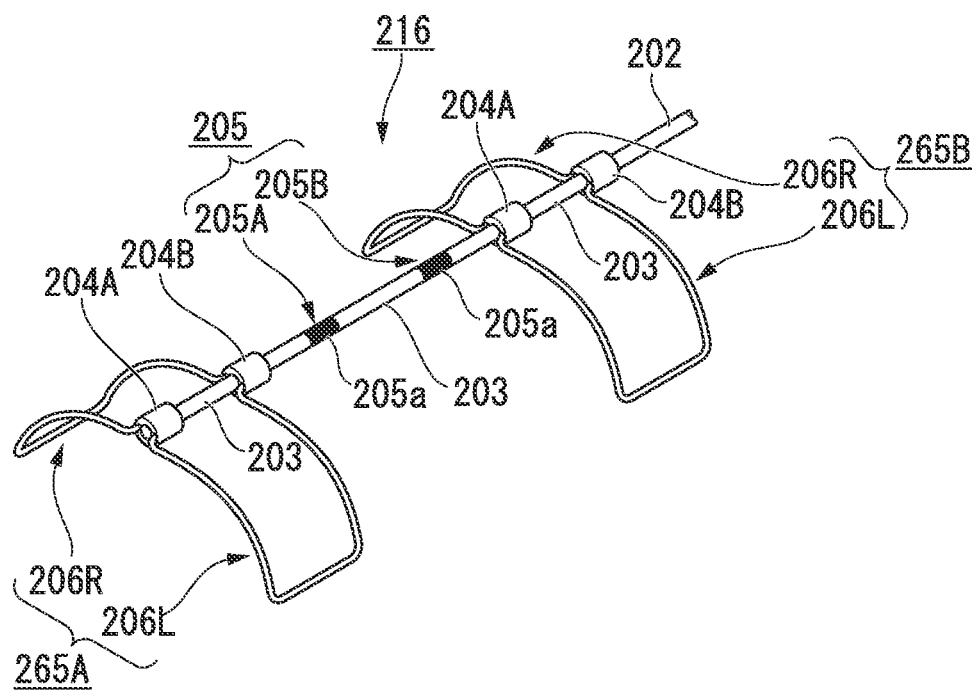
FIG. 29 is a schematic perspective view showing a tenth modification of the electrostimulation electrode assembly according to the fifth embodiment of the present invention.
Figure 30A:
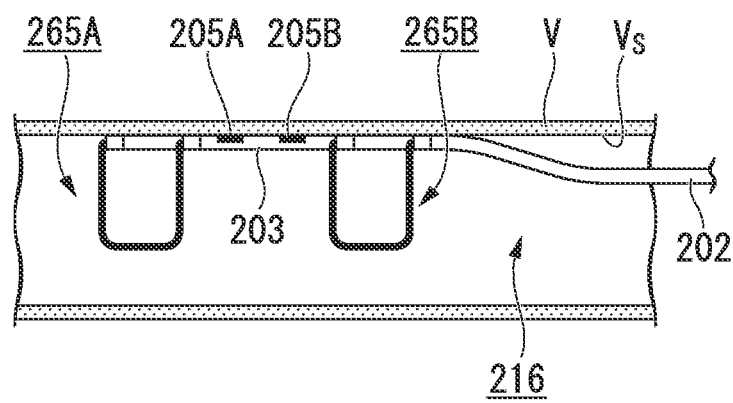
FIG. 30A is a schematic sectional view illustrating the effect of the tenth modification of the electrostimulation electrode assembly according to the fifth embodiment of the present invention.
Figure 30B:
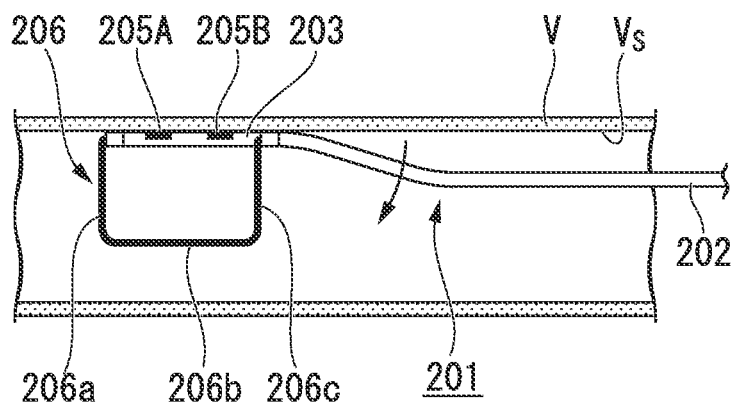
FIG. 30B is a schematic sectional view showing the effect of the tenth modification of the electrostimulation electrode assembly according to the fifth embodiment of the present invention.

FIG. 29 is a schematic perspective view showing a tenth modification of the electrostimulation electrode assembly according to the fifth embodiment of the present invention. FIGS. 30A and 30B are schematic sectional views illustrating the effect of the tenth modification of the electrostimulation electrode assembly according to the fifth embodiment of the present invention.

As shown in FIG. 29, an electrode stimulation lead 216 (electrostimulation electrode assembly) of this modification includes a leading end-side electrode urging member 265A and a base end-side electrode urging member 265B as an electrode urging member, in place of the electrode urging member 206 of the electrode stimulation lead 201 of the fifth embodiment. Hereinafter, a description will be provided focusing on the differences from the fifth embodiment.

The leading end-side electrode urging member 265A is configured such that the fixing hooks 206R and 206L are respectively fixed to the support 203 as the leading end side of the electrode portion 205 by the leading end-side fixed portion 204A and the base end-side fixed portion 204B.

The base end-side electrode urging member 265B is configured such that the fixing hooks 206R and 206L are respectively fixed to the support 203 as the leading end side of the electrode portion 205 by the leading end-side fixed portion 204A and the base end-side fixed portion 204B.

The leading end-side electrode urging member 265A and the base end-side electrode urging member 265B are provided at overlapping positions when viewed from the axial direction of the support 203 and arrayed in one curved surface.

According to this modification, the leading end side and the base end side of the electrode portion 205 of the support 203 are urged by the leading end-side electrode urging member 265A and the base end-side electrode urging member 265B which are different electrode urging members. For this reason, since the support 203 is fixed at two places on both end sides, each exposed electrode surface 205a of the electrode portion 205 is not easily separated from the vein inner wall $V_s$.

For example, as shown in FIG. 30A, if the sheathing member 202 is separated to the center of the vein V, the base end side of the support 203 is caught by the sheathing member 202 and separated from the vein inner wall $V_s$. At this time, since the base end-side electrode urging member 265B is provided which urges the vein inner wall $V_s$ only on the base end side of the support 203, it is possible to prevent the base end side of the support 203 from being separated. At this time, since an influence of separation of the sheathing member 202 is not easily transmitted to the leading end-side electrode urging member 265A, even if the fixing of the base end-side electrode urging member 265B is loosened, the leading end-side electrode urging member 265A can support the support 203 such that misalignment or the like does not occur.

Meanwhile, as shown in FIG. 30B, in the fifth embodiment, if the sheathing member 202 is separated, external force is transmitted to the leading end side of the support 203 through the arcuate arm portion 206c, the hook leading end portion 206b, and the arcuate arm portion 206a of the electrode urging member 206, and affects the fixed state on the base end side of the support 203. For this reason, there is an influence of external force, such as separation of the sheathing member 202, compared to this modification.

As described above, a plurality of electrode urging members may be provided along the axial direction of the support 203. Although in this modification, an example has been described where two electrode urging members are provided, two or more electrode urging members may be provided. For example, the same electrode urging member may also be provided between the negative electrode 205A and the positive electrode 205B, such that three electrode urging members may be provided in total.

[Eleventh Modification]

Next, an eleventh modification of the electrostimulation electrode assembly of this embodiment will be described.

Figure 31:
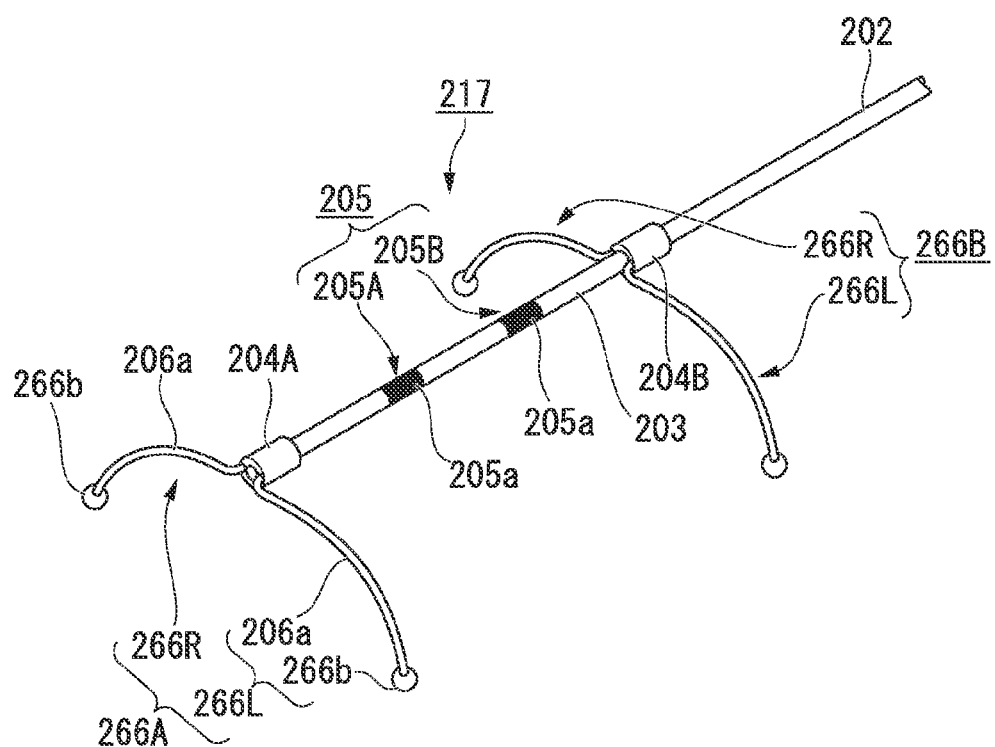
FIG. 31 is a schematic perspective view showing an eleventh modification of the electrostimulation electrode assembly according to the fifth embodiment of the present invention.

FIG. 31 is a schematic perspective view showing an eleventh modification of the electrostimulation electrode assembly according to the fifth embodiment of the present invention.

As shown in FIG. 31, an electrode stimulation lead 217 (electrostimulation electrode assembly) of this modification includes a leading end-side electrode urging member 266A and a base end-side electrode urging member 266B as an electrode urging member, in place of the electrode urging member 206 of the electrode stimulation lead 201 of the fifth embodiment. Hereinafter, a description will be provided focusing on the differences from the fifth embodiment.

The leading end-side electrode urging member 266A includes arm-like fixing hooks 266R and 266L with a spherical contact portion 266b at the leading end of the arcuate arm portion 206a while the hook leading end portion 206b and the arcuate arm portion 206c of the fixing hooks 206R and 206L are eliminated.

The base end-side electrode urging member 266B is configured such that arm-like fixing hooks 266R and 266L are fixed to the base end-side fixed portion 204B in the same manner as the leading end-side fixed portion 204A.

The leading end-side electrode urging member 266A and the base end-side electrode urging member 266B are provided at overlapping positions when viewed from the axial direction of the support 203 and arrayed in one curved surface.

According to this modification, a plurality of electrode urging members can be constituted by an arm-like extended member with simple configuration. For this reason, manufacturing is facilitated. The member is easily deformed at the time of insertion into the tubular member, and accommodation in the tubular member is facilitated.

Since the attachment width is reduced, when the length of the support 203 is identical, for example, the number of electrode urging members in the axial direction easily increases compared to the tenth modification.

Since the spherical contact portion 266b is provided, the leading ends of the arm-like fixing hooks 266R and 266L come into smooth contact with the vein inner wall $V_s$, thereby reducing the load imposed on the vein inner wall $V_s$.

[Sixth Embodiment]

Next, an electrostimulation electrode assembly according to a sixth embodiment of the present invention will be described. Similarly to the electrostimulation electrode assembly of the fifth embodiment, the electrostimulation electrode assembly of this embodiment can be used in combination with the electrostimulation system according to each of the first to fourth embodiments of the invention.

Figure 32A:
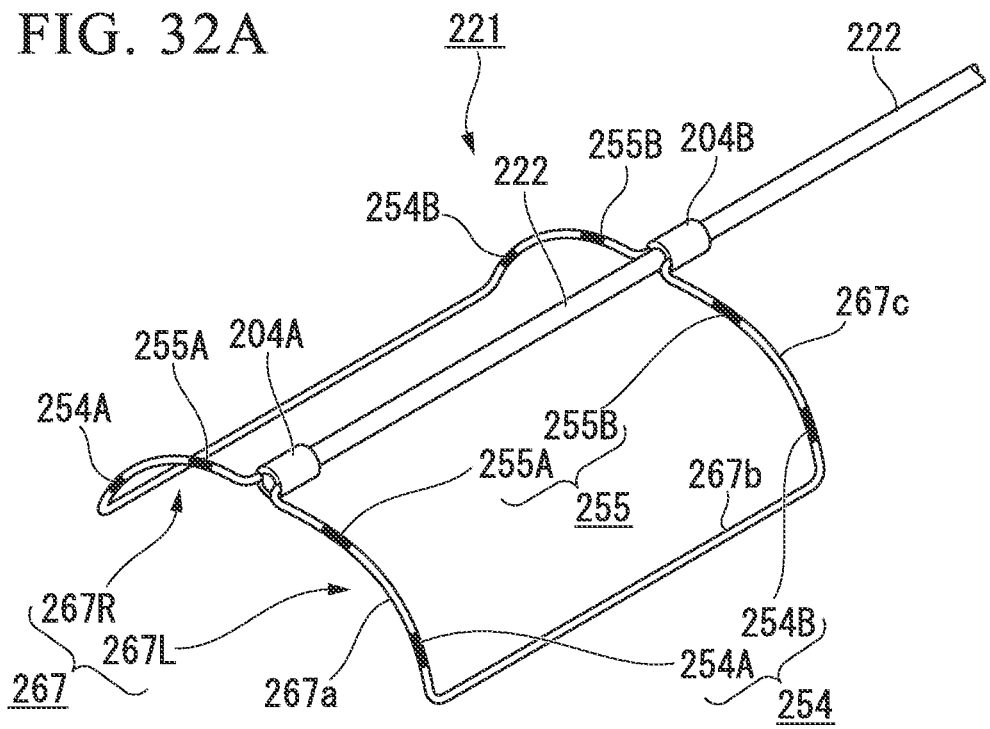
FIG. 32A is a schematic perspective view of a main part of an electrostimulation electrode assembly according to a sixth embodiment of the present invention.
Figure 32B:
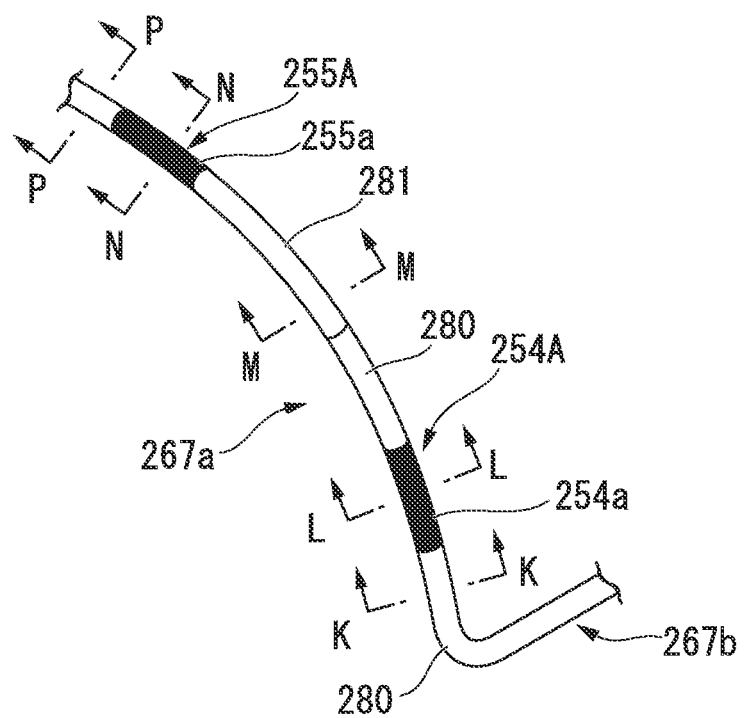
FIG. 32B is a partial enlarged view of a main part of the biological implantable electrode according to the sixth embodiment of the present invention.
Figure 33A:
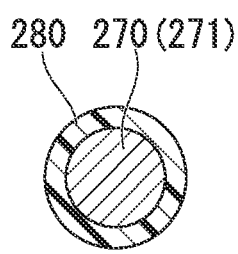
FIG. 33A is a sectional view taken along the line K-K of FIG. 32B.
Figure 33B:
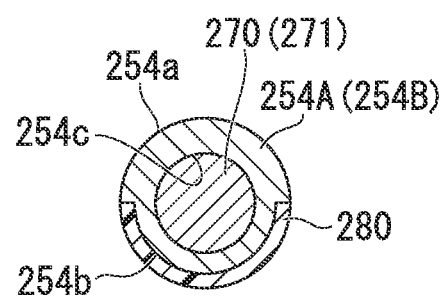
FIG. 33B is a sectional view taken along the line L-L of FIG. 32B.
Figure 33C:
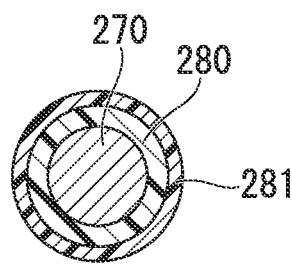
FIG. 33C is a sectional view taken along the line M-M of FIG. 32B.
Figure 33D:
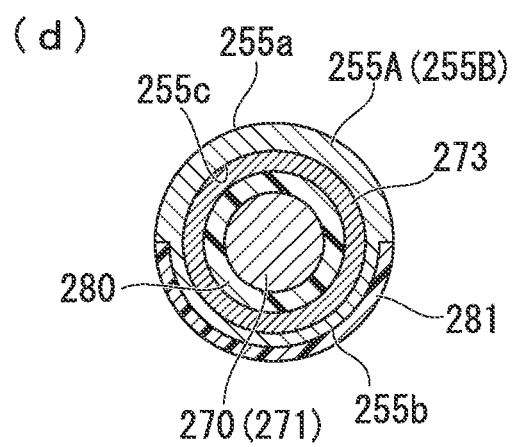
FIG. 33D is a sectional view taken along the line N-N of FIG. 32B.
Figure 33E:
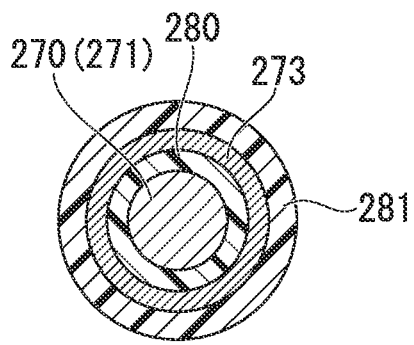
FIG. 33E is a sectional view taken along the line P-P of FIG. 32B.
Figure 34:
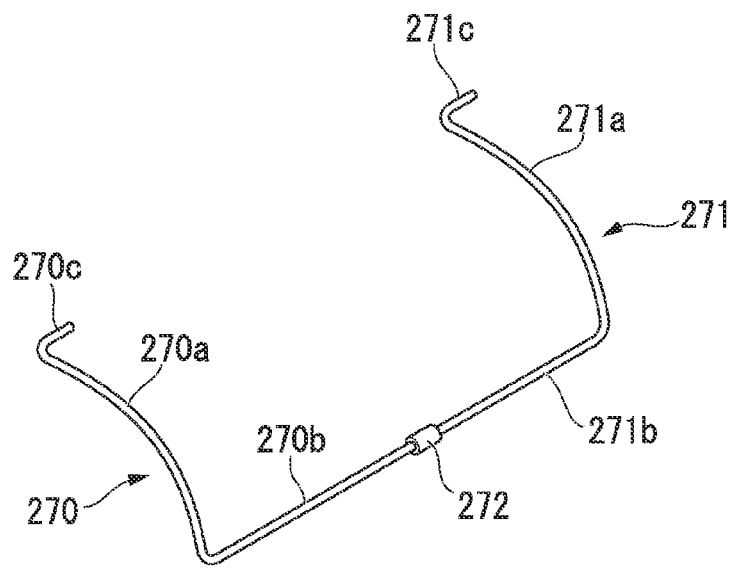
FIG. 34 is a schematic perspective view of an elastic body which is used in the electrostimulation electrode assembly according to the sixth embodiment of the present invention.
Figure 35:
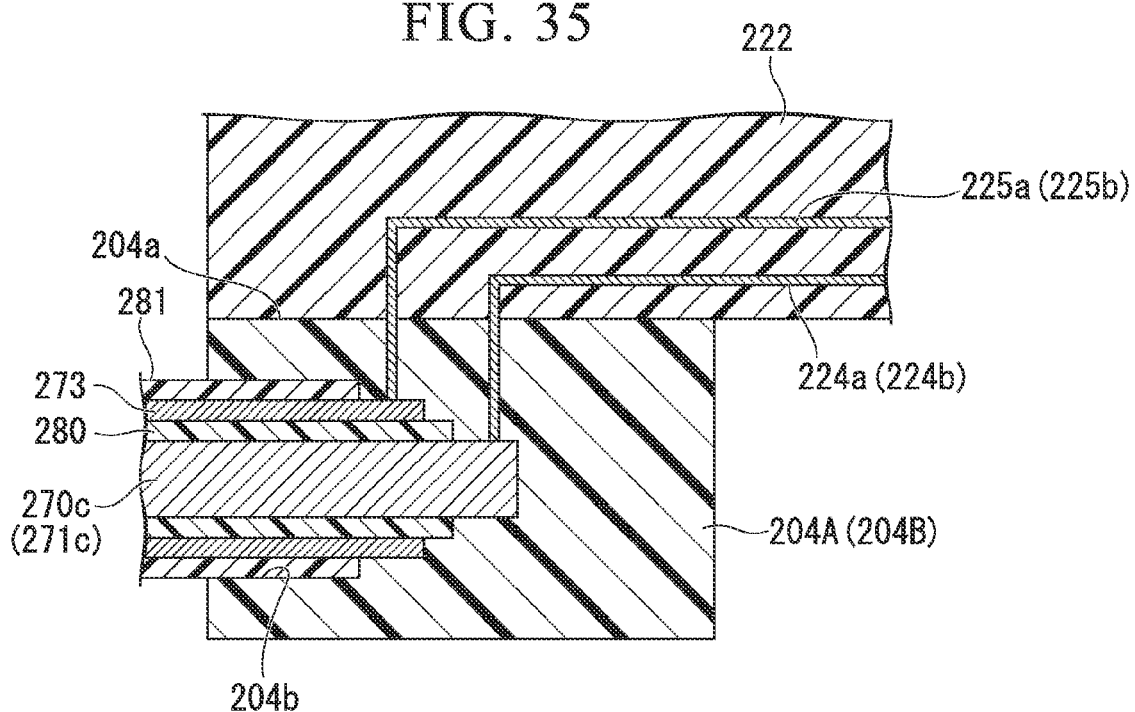
FIG. 35 is a schematic sectional view showing the connection structure of a conducting wire member in the electrostimulation electrode assembly according to the sixth embodiment of the present invention.
Figure 36:
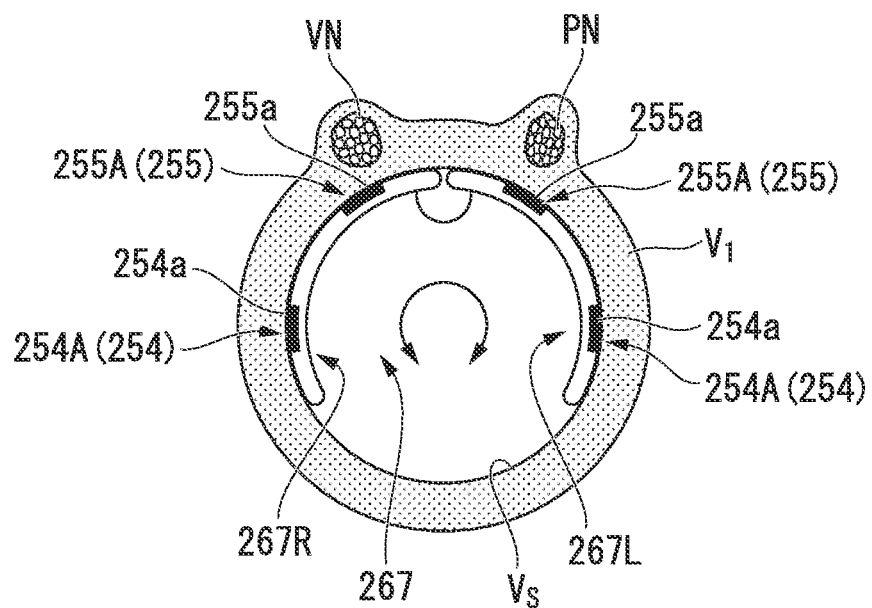
FIG. 36 is a schematic sectional view showing a state where the electrostimulation electrode assembly according to the sixth embodiment of the present invention is loaded in a superior vena cava.

FIG. 32A is a schematic perspective view of a main part of an electrostimulation electrode assembly according to a sixth embodiment of the invention. FIG. 32B is a partial enlarged view of FIG. 32A. FIG. 33A is a sectional view taken along the line K-K of FIG. 32B. FIG. 33B is a sectional view taken along the line L-L of FIG. 32B. FIG. 33C is a sectional view taken along the line M-M of FIG. 32B. FIG. 33D is a sectional view taken along the line N-N of FIG. 32B. FIG. 33E is a sectional view taken along the line P-P of FIG. 32B. FIG. 34 is a schematic perspective view of an elastic body which is used in the electrostimulation electrode assembly according to the sixth embodiment of the present invention. FIG. 35 is a schematic sectional view showing the connection structure of a conducting wire member in the electrostimulation electrode assembly according to the sixth embodiment of the present invention. FIG. 36 is a schematic sectional view showing a state where the electrostimulation electrode assembly according to the sixth embodiment of the present invention is loaded in a superior vena cava.

As shown in FIGS. 32A and 32B, an electrode stimulation lead 221 (electrostimulation electrode assembly) of this embodiment includes a sheathing member 222, in place of the support 203 and the sheathing member 202 of the electrode stimulation lead 201 of the fifth embodiment, and as in the fifth embodiment, the leading end-side fixed portion 204A and the base end-side fixed portion 204B are fixed in the leading end portion of the sheathing member 222. In place of the fixing hooks 206R and 206L, an electrode support portion 267 is provided which includes an electrode portion 254 having a negative electrode 254A (electrode) and a positive electrode 254B (electrode) and an electrode portion 255 having a negative electrode 255A (electrode) and a positive electrode 255B (electrode). Hereinafter, a description will be provided focusing on the differences from the fifth embodiment.

The sheathing member 222 is a linear portion which is formed of the same material as the sheathing member 202 of the fifth embodiment, and has passed therethrough a plurality of conducting wires 224*a*, 224*b*, 225*a*, and 225*b* (conducting wire member, see FIG. 35) in the axial direction to provide electrical conduction between the electrode portions 254 and 255 and the connector 209 (not shown).

However, the connector 209 of the embodiment is provided with a plurality of electrode terminals corresponding to the number of electrode portions 254 and 255.

The electrode support portion 267 includes electrode-equipped fixing hooks 267R and 267L which are linear portions bent in the same shape as the fixing hooks 206R and 206L.

Each of the electrode-equipped fixing hooks 267R and 267L include an arcuate support 267*a*, a hook leading end portion 267*b*, and an arcuate support 267*c* to correspond to the arcuate arm portion 206*a*, the hook leading end portion 206*b*, and the arcuate arm portion 206*c*. The arcuate support 267*a* is provided with the negative electrodes 254A and 255A, and the arcuate support 267*c* is provided with the positive electrodes 254B and 255B.

The internal structure of the electrode-equipped fixing hook 267R (267L) is as shown in FIGS. 33A, 33B, 33C, 33D, and 33E. That is, a sheathing tube 280, a coil conducting wire 273, and a sheathing tube 281 are laminated on the outer circumferential portions of linear elastic bodies 270 and 271 as a core member in a concentric layer shape.

The electrode-equipped fixing hooks 267R and 267L are fixed to the leading end-side fixed portion 204A and the base end-side fixed portion 204B with the positional relationship so as to be plane-symmetric to one cross-section including the central axis of the leading end portion of the sheathing member 222. For this reason, similarly to the fixing hooks 206R and 206L, the electrode-equipped fixing hooks 267R and 267L are bent in an arc shape when viewed from the axial direction of the sheathing member 222 and arrayed in one curved surface as a whole.

As shown in FIG. 34, the linear elastic body 270 includes a fixed end portion 270*c* and an arcuate arm portion 270*a* which are bent in the same manner as the fixed end portion 206*d* and the arcuate arm portion 206*a* in the fixing hook 206R (206L). A linear portion 270*b* having a length half of the hook leading end portion 206*b* is fixed to the leading end portion of the arcuate arm portion 270*a* in the protrusion direction in the same manner as the hook leading end portion 206*b*.

The linear elastic body 271 includes a fixed end portion 271*c* and an arcuate arm portion 271*a* which are bent in the same manner as the fixed end portion 206*e* and the arcuate arm portion 206*c* in the fixing hook 206R (206L). A linear portion 271*b* having a length half of the hook leading end portion 206*b* is connected to the leading end portion of the arcuate arm portion 271*a* in the protrusion direction in the same manner as the hook leading end portion 206*b*.

The leading end portions of the linear portions 270*b* and 271*b* in the extension direction face each other in the axial direction and are connected coaxially by a shaft-like insulating connection member 272 having electrical insulation.

Thus, the linear elastic bodies 270 and 271 constitute a core member which is bent in the same manner as the fixing hook 206R (206L) as a whole.

The linear elastic bodies 270 and 271 are made of an elastic material having the same conductivity as the linear elastic body 206 of the fifth embodiment.

As shown in FIGS. 32B and 33A, the sheathing tube 280 sheathes the outer circumferential portion of the linear elastic body 270 (271) and is made of the same electrical insulating material as the sheathed layer 208 of the fifth embodiment.

On the leading end side of the arcuate arm portion 270*a* (271*a*) in the protrusion direction, the negative electrode 254A (positive electrode 254B) is provided.

The negative electrode 254A (positive electrode 254B) is substantially made of the same cylindrical member as the electrode 252 according to the fourth modification of the fifth embodiment. That is, as shown in FIG. 33B, a through hole 254*c* is provided in the central portion, and in the outer circumferential surface of the negative electrode 254A (positive electrode 254B), a semi-cylindrical exposed electrode surface 254*a* having the same diameter as the outer diameter of the sheathing tube 280 and an outer circumference fixed portion 254*b* constituted by a semi-cylindrical surface having a diameter smaller than the exposed electrode surface 254*a* are provided.

The exposed electrode surface 254*a* is exposed toward the lateral surface in the convex direction of curvature of the electrode-equipped fixing hook 267R (267L).

The linear elastic body 270 (271) passes through the through hole 254*c*. The through hole 254*c* is connected to the outer circumferential surface of the linear elastic body 270 (271) by, for example, welding, swaging, or the like. Thus, the exposed electrode surface 254*a* is also electrically connected to the linear elastic body 270 (271).

With this configuration, the negative electrode 254A (positive electrode 254B) is supported by the sheathing tube 280 having electrical insulation in a state where a portion thereof is exposed from the surface as the exposed electrode surface 254*a*. For this reason, the sheathing tube 280 constitutes a support of the negative electrode 254A (positive electrode 254B).

On the base end side of the arcuate arm portion 270*a* (271*a*) in the protrusion direction, the negative electrode 255A (positive electrode 255B) is provided at a position distant from the negative electrode 254A (positive electrode 25413).

The negative electrode 255A (positive electrode 255B) is substantially made of the same cylindrical member as the electrode 252 according to the fourth modification of the fifth embodiment. That is, as shown in FIG. 33D, a through hole 255c having a diameter greater than the sheathing tube 280 is provided in the central portion, and on the outer circumferential surface of the negative electrode 255A (positive electrode 255B), a semi-cylindrical exposed electrode surface 255a and an outer circumference fixed portion 255b made of a semi-cylindrical surface having a diameter smaller than the exposed electrode surface 255a are provided.

The exposed electrode surface 255a is exposed toward the lateral surface in the convex direction of curvature of the electrode-equipped fixing hook 267R (267L).

The coil conducting wire 273, through which the sheathing tube 280 passes, passes through the through hole 255c. The through hole 255c is connected to the outer circumferential surface of the coil conducting wire 273 by, for example, welding, swaging, or the like. Thus, the exposed electrode surface 255a is also electrically connected to the coil conducting wire 273.

The coil conducting wire 273 extends to the base end side of the linear elastic body 270 in the protrusion direction and the fixed end portion 270c (271c) in a state of being in close contact with the outer circumferential surface of the sheathing tube 280.

As the material of the coil conducting wire 273, an appropriate elastic material having conductivity may be used insofar as the material is resistant to bending of the arcuate arm portion 270a (271a) in the vein.

As shown in FIGS. 32A, 33C, and 33D, the sheathing tube 281 sheathes the sheathing tube 280 or the outer circumferential portion of the coil conducting wire 273 which passes through the sheathing tube 280 in the arcuate arm portion 270a (271a) in a range between the negative electrode 254A (positive electrode 254B) and the negative electrode 255A (positive electrode 255B) and from the end portion of the negative electrode 255A (positive electrode 255B) on the fixed end portion 270c (271c) side to the fixed end portion 270c (271c).

The sheathing tube 281 is made of the same electrical insulation material as the linear elastic body 207 of the fifth embodiment.

As shown in FIG. 33D, the sheathing tube 281 is provided so as to cover the outer circumference fixed portion 255b of the negative electrode 255A (positive electrode 255B) at the position corresponding to the negative electrode 255A (positive electrode 255B).

With this configuration, the negative electrode 255A (positive electrode 255B) is supported by the sheathing tube 281 having electrical insulation in a state where a portion thereof is exposed from the surface as the exposed electrode surface 255a. For this reason, the sheathing tube 281 constitutes a support of the negative electrode 255A (positive electrode 255B).

As shown in FIG. 35, the end portion of the fixed end portion 270c (271c) is fixed to the hook fixing portion 204b in a state where the outer circumferential surface of the fixed end portion 270c (271c) and the outer circumferential surface of the coil conducting wire 273 are exposed in the radial direction.

The fixed end portion 270c (271c) and the coil conducting wire 273 are electrically connected to a plurality of conducting wires which pass through the sheathing member 222.

For example, the fixed end portion 270c (271c) which is in the conduction state to the negative electrode 254A (255A) is connected to the conducting wire 224a (224b) which is in the conduction state to the terminal for a negative electrode of the connector 209. The coil conducting wire 273 which is in the conduction state to the positive electrode 254B (255B) is connected to the conducting wire 225a (225b) which is in the conduction state to the terminal for a positive electrode of the connector 209.

For this reason, the linear elastic body 270 (271) and each coil conducting wire 273 are electrically connected to the electrodes in the support and constitute a conducting wire member which extends outside the support.

The electrode stimulation lead 221 configured as above can be inserted into the vein, such as the superior vena cava $V_1$, by using an appropriate tubular member in the same manner as in the fifth embodiment. As shown in FIG. 36, the leading end portion of the electrode stimulation lead 221 inserted into the superior vena cava $V_1$ presses the vein inner wall $V_s$ to urge the vein inner wall $V_s$ outward in the radial direction because the electrode-equipped fixing hook 267R (267L) is opened toward the vein inner wall $V_s$.

Urging force at this time is defined by elastic restoring force from elastic deformation of the linear elastic body 270 (271) and elastic deformation of each coil conducting wire 273.

For this reason, the linear elastic body 270 (271) and each coil conducting wire 273 are connected to the support to constitute an electrode urging member which urges the electrode exposed from the support toward the inner wall of the vein.

At the time of urging, the exposed electrode surfaces 254a and 255a of the electrodes are exposed toward the lateral surface in the convex direction of curvature of the electrode-equipped fixing hook 267R (267L). For this reason, the exposed electrode surfaces 254a and 255a face the vein inner wall $V_s$ and are pressed into close contact with the vein inner wall $V_s$. The rear sides of the exposed electrode surfaces 254a and 255a are covered by the sheathing tubes 280 and 281 as a support over the entire region of the electrode.

For this reason, as in the fifth embodiment, the electrode can be inserted into the vein, and the electrode can be urged toward the inner wall of the vein and attached in the vein. Thus, it is possible to carry out electrostimulation indirectly through the vein without being in direct contact with the nervous tissue.

In this embodiment, the electrode-equipped fixing hook 267R (267L) comes into close contact with the vein inner wall $V_s$ along the circumferential direction of the vein inner wall $V_s$, and has a plurality of electrodes which can apply electrical stimulus independently each other. For this reason, it is possible to change an electrostimulation position in the circumferential direction of the vein without rotating the position of the electrode-equipped fixing hook 267R (267L) in the circumferential direction by selecting an electrode for applying electrical stimulus.

For this reason, even when the electrode support portion 267 is shifted from a predetermined position, an electrode near the predetermined position can be selected and electrostimulation can be carried out. Even when it is necessary to correct misalignment, the amount of shift of the electrode support portion 267 in the circumferential direction decreases, such that the placement of the electrode support portion 267 can be rapidly done.

For example, as shown in FIG. 36, when the electrode support portion 267 is provided inside the superior vena cava $V_1$, the electrode portion 255 of the electrode-equipped fixing hook 267R is arranged at a position substantially facing the vagus nerve VN, and the electrode portion 255 of the electrode-equipped fixing hook 267L is arranged at a position substantially facing a phrenic nerve PN in the vicinity of the vagus nerve VN.

In such a case, the vagus nerve VN can be stimulated by the electrode portion 255 of the electrode-equipped fixing hook 267R without stimulating the phrenic nerve PN. The phrenic nerve PN can be stimulated by the electrode portion 255 of the electrode-equipped fixing hook 267L without stimulating the vagus nerve VN.

A single electrode stimulation lead 221 may be arranged to apply different electrical stimuli to the vagus nerve VN and the phrenic nerve PN simultaneously. For this reason, it is possible to reduce time and labor at the time of insertion and also to reduce the number of leads in the vein. Therefore, the blood flow is not easily inhibited, and it is possible to suppress the occurrence of thrombus.

Although in the above description, an example has been described where the electrostimulation electrode assembly stimulates the vagus nerve VN or the phrenic nerve PN, the electrostimulation electrode assembly may apply electrical stimulus to any nervous tissue insofar as the nervous issue is in the vicinity of the vein, and is not limited to the purpose for electrostimulation treatment of the vagus nerve VN or the phrenic nerve PN.

Although in the above described, an example has been described where an electrode urging member is fixed by using the leading end-side fixed portion 204A and the base end-side fixed portion 204B, this is just an example of the method of fixing the electrode urging member, and the fixing method is not limited.

For example, the end portion of the electrode urging member may be brought into close contact with the lateral surface of the support, and the end portion may be swaged or bonded on the outer circumference of the support. The end portion of the electrode urging member may be molded as a single body with the support and fixed to the support. A tubular attachment portion may be provided in the end portion of the electrode urging member, and the support may be externally engaged with and fixed to the attachment portion.

Although in the above description, an example has been described where the cross-section of the support has a circular shape, the support is not limited to a circular sectional shape insofar as the shape can come into close contact with the vein inner wall $V_s$ along with the electrode. For example, a shape having an elliptical cross-section, an oval cross-section, a rectangular cross-section, an arcuate cross-section, or the like may be used. The support is not limited to a columnar shape and may have a plate shape, a block shape, or the like.

Although in the above description, an example has been described where the electrode portion is constituted by an electrode the pair of negative electrode and the positive electrode, a counter electrode for electrostimulation may be provided separately from the electrostimulation electrode assembly, and then electrostimulation may be carried out. In this case, the electrostimulation electrode assembly may have only one electrode.

Although in the above description, an example has been described where the electrode urging member is connected to the support at the position with the exposed electrode surface sandwiched therebetween in the extension direction of the support, the position of the electrode urging member in the extension direction of the support is not particularly limited insofar as the exposed electrode surface can be urged toward the inner wall of the vein.

For example, the electrode urging member may be connected to the support at the same position as the exposed electrode surface in the extension direction of the support. Specifically, the arm-like fixing hook of the eleventh modification may be configured to extend from the support laterally to the exposed electrode surface.

The electrode urging member may be provided at the position sandwiched between two exposed electrode surfaces in the extension direction of the support.

Although in the above-description, an example has been described where the support connection portion 204a of the leading end-side fixed portion 204A is constituted by the through hole, a non-through hole may be used.

Figure 37:
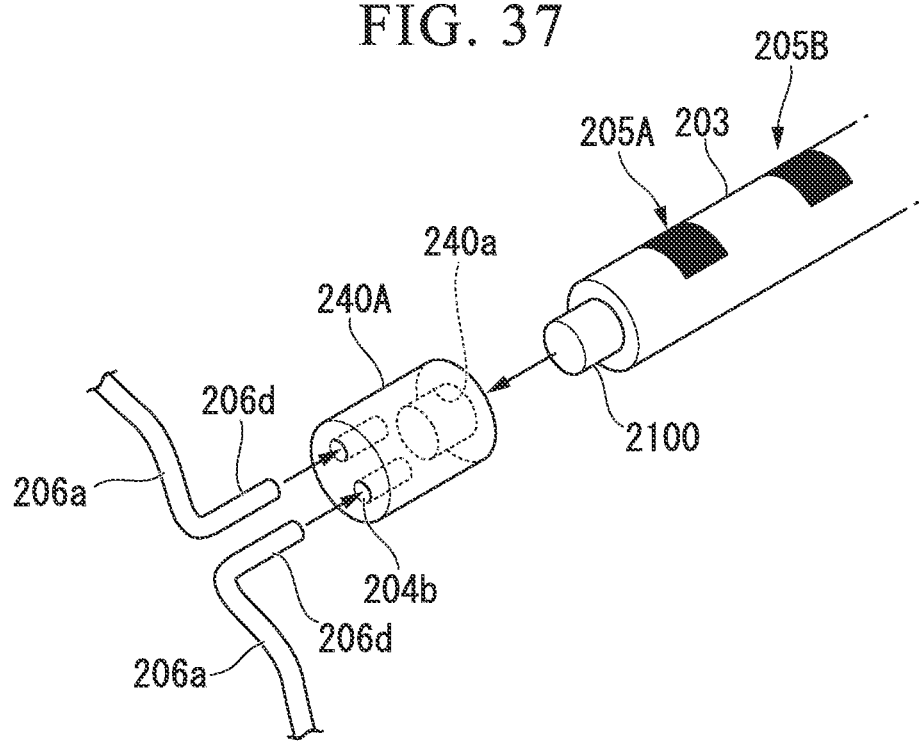
FIG. 37 is a schematic perspective view showing an example of a modification of a leading end-side fixed portion.

For example, a leading end-side fixed portion 240A shown in FIG. 37 may be used. That is, only a pair of hook fixing portions 204b are provided on the leading end side of the leading end-side fixed portion 240A, and an aperture portion 240a is provided in the central portion on the base end side of the leading end-side fixed portion 240A so as to be formed to the intermediated portion of the leading end-side fixed portion 240A in the axial direction. In this case, a protrusion portion 2100 which will be engaged with the aperture portion 240a is provided in the leading end portion of the support 203, and the protrusion portion 2100 is engaged with the aperture portion 240a, such that the support 203 and the leading end-side fixed portion 240A are mechanically fastened to each other.

With this configuration, the outer diameter of the leading end-side fixed portion 240A can be closer to the outer diameter of the support 203 or can be set to be equal to or smaller than the outer diameter of the support 203. For example, the dimensional relationship can be established that the outer diameter of the support 203 is ϕ1.9 mm and the outer diameter of the leading end-side fixed portion 240A is ϕ2.0 mm. In this way, the outer diameter of the support 203 and the outer diameter of the leading end-side fixed portion 240A are substantially the same, making it possible to reduce the gap between the negative electrode 205A and the positive electrode 205B and the vein inner wall due to the difference in the outer diameter between the negative electrode 205A and the positive electrode 205B fitted to the outer diameter of the support 203 and the leading end-side fixed portion 240A, thus reliably transmitting electrical stimulus.

Although in the above description, an example has been described where the outer shape of each of the leading end-side fixed portion 204A and the base end-side fixed portion 204B is a circular shape, the outer shape of each of the leading end-side fixed portion 204A and the base end-side fixed portion 204B is not limited to a circular shape.

Figure 38:
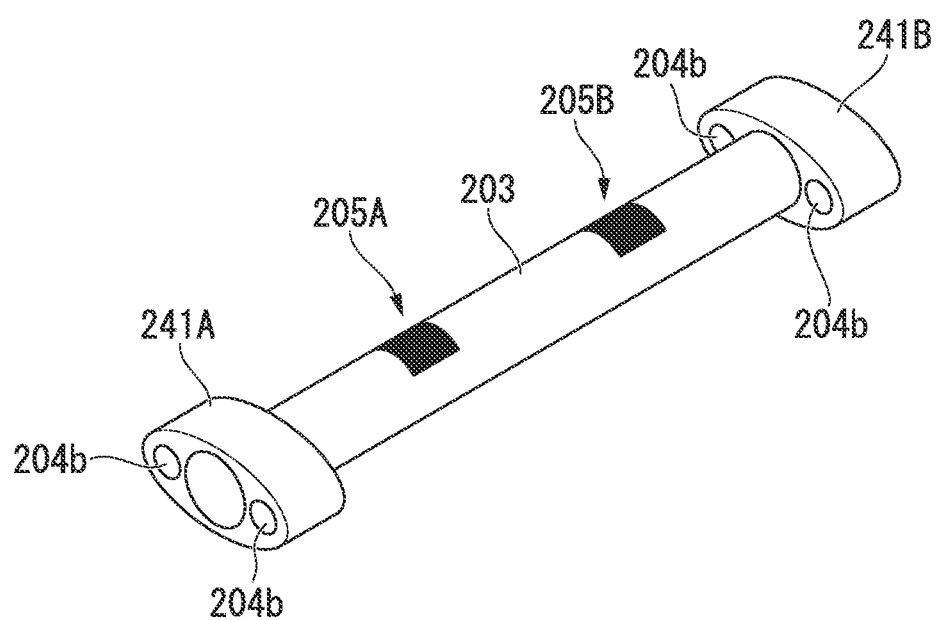
FIG. 38 is a schematic perspective view showing another example of a modification of a leading end-side fixed portion and a base end-side fixed portion.

For example, like a leading end-side fixed portion 241A and a base end-side fixed portion 241B shown in FIG. 38, an elliptical cylindrical shape may be used in which the direction in which the exposed electrode surface 205a goes forward becomes a minor axis. In the major-axis direction of the leading end-side fixed portion 241A and the base end-side fixed portion 241B, the same hook fixing portions 204b as described above may be provided.

In this case, when the minor axis of each of the leading end-side fixed portion 241A and the base end-side fixed portion 241B is close to the outer diameter of the support 203, it is possible to reduce a step with respect to the support 203. Therefore, it is possible to reduce the gap between the negative electrode 205A and the positive electrode 205B and the vein inner wall due to the step between the negative electrode 205A and the positive electrode 205B fitted to the outer diameter of the support 203 and the leading end-side fixed portion 241A and the base end-side fixed portion 241B. As a result, it is possible to reliably transmit electrical stimulus.

[Seventh Embodiment]

Figure 39:
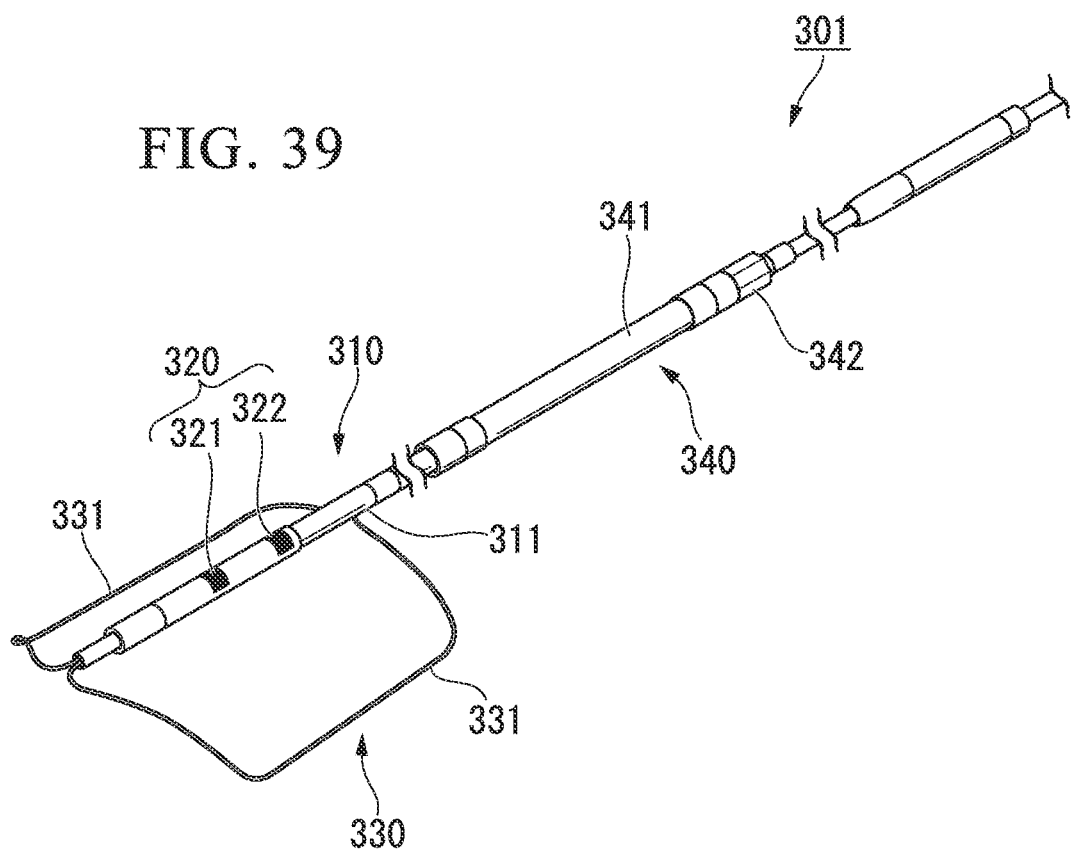
FIG. 39 is a perspective view showing a biological implantable electrode according to a seventh embodiment of the present invention.

As a seventh embodiment of the invention, a biological implantable electrode which can be used in combination with the electrostimulation system according to each of the first to fourth embodiments of the present invention will be described with reference to FIGS. 39 to 45. FIG. 39 is a perspective view showing a biological implantable electrode 301 of this embodiment. The biological implantable electrode 301 is placed in the vein to apply electrical stimulus to a target tissue in the vicinity of the vein. The biological implantable electrode 301 includes an elongated conducting wire sheathing body 310, an electrode portion 320 which is provided on the leading end side of the conducting wire sheathing body 310, an electrode support 330 which is provided in the vicinity of the electrode portion 320, and a withdrawal portion (deformation mechanism) 340 which is used to remove the biological implantable electrode 301.

The conducting wire sheathing body 310 includes conducting wires (not shown), and an insulating layer 311 which sheathes the circumference of the conducting wires. The two conducting wires are provided for the plus and minus sides, and stranded wires made of, for example, a nickel-cobalt alloy may be used. As the material of the insulating layer 311, a polymer material having biocompatibility, such as polyurethane, silicone, or ETFE, may be used. In this embodiment, the insulating layer 311 is a tube made of polyurethane, and two conducting wires made of nickel-cobalt alloy pass through the lumen so as not to be short-circuited.

Like the biological implantable electrode 301 which is placed in the vein, if necessary, the outer surface of the insulating layer 311 may be subjected to coating for thrombus prevention. As the material of coating, an MPC polymer or the like may be used.

The conducting wire of the conducting wire sheathing body 310 is connected to an electrical stimulus generation device 1200 (not shown) or the like on the base end side on which no electrode portion 320 is provided. For ease of connection, if necessary, a connector or the like may be provided on the base end side of the conducting wire sheathing body 310.

The electrode portion 320 applies electrical stimulus to a biological tissue, and is constituted by a plus electrode 321 on the leading end side and a minus electrode 322 on the base end side from the plus electrode 321. The plus electrode 321 and the minus electrode 322 are formed on the outer surface of the conducting wire sheathing body 310 and are respectively connected to the plus conducting wire and the minus conducting wire of the conducting wire sheathing body 310. Examples of the material of the electrode portion 320 include platinum, stainless steel, gold, silver, titanium, conductive oxides of the metals, and the like. From the viewpoint of a place where the electrode portion 320 comes into contact with the biological body, a noble metal having biocompatibility, such as platinum-iridium, is preferably used.

The plus electrode 321 and the minus electrode 322 are formed in a range of an arc shape corresponding to a predetermined center angle in the outer circumferential surface of the conducting wire sheathing body 310 substantially having a columnar shape. The magnitude of the center angle for defining the forming range of each of the electrodes 321 and 322 may be appropriately set in consideration of the following matter.

If the center angle is excessively small, the area of each of the electrodes 321 and 322 is excessively small, and a high voltage for electrostimulation should be applied. If the center angle is excessively large, the area of each of the electrodes 321 and 322 is excessively large, and electricity is likely to leak to other peripheral tissues.

For example, when electrical stimulus is applied to a vagus nerve in the vicinity of a superior vena cava, if the center angle is set to be excessively large, electricity may leak and a phrenic nerve which is running near the vagus nerve may be stimulated. If the center angle is excessively large, the electrode and blood are likely to come into contact with each other, and electrical energy flows through blood rather than a vascular tissue facing the vagus nerve, making it difficult to stimulate the vagus nerve.

The dimension of each of the electrodes 321 and 322 in the longitudinal direction of the conducting wire sheathing body 310 and the distance between the plus electrode 321 and the minus electrode 322 may be appropriately set. In this embodiment, the dimension of each of the electrodes 321 and 322 in the longitudinal direction of the conducting wire sheathing body 310 is about 2 millimeters (mm), and the distance between the plus electrode 321 and the minus electrode 322 is about 5 mm.

The electrode support 330 is constituted by two superelastic wires 331. Each superelastic wire 331 is formed so as to maintain a frame shape (first shape) with an increasing width in the width direction of the conducting wire sheathing body 310 in the natural site where no external force is applied, and both end portions of each superelastic wire 331 are fixed to the conducting wire sheathing body 310.

Figure 40:
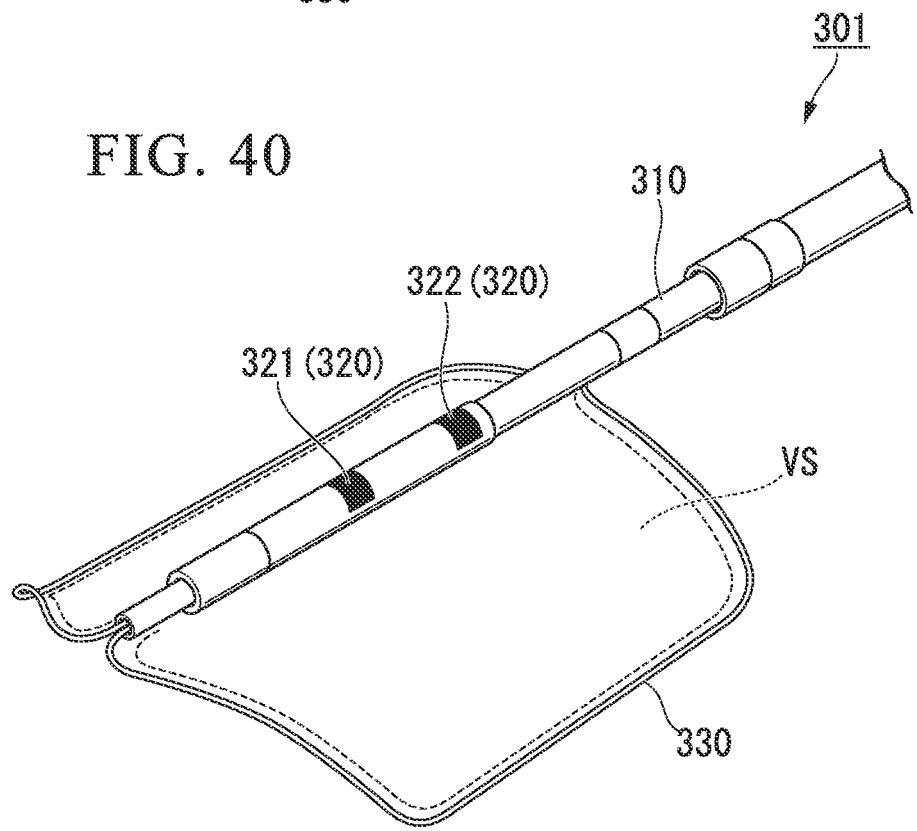
FIG. 40 is an enlarged view showing the periphery of an electrode portion of the biological implantable electrode according to the seventh embodiment of the present invention.

As shown in FIG. 40 on a magnified scale, a virtual surface VS which is formed by the electrode support 330 in the first shape has an arc shape which is made convex toward the electrode portion 320 when viewed in the axial direction of the conducting wire sheathing body 310. The radius of curvature of the arc is set to be a value equal to or greater than the average diameter in which the biological implantable electrode 301 is placed.

The electrode support 330 is configured such that the shape thereof can be changed when external force is applied and reversibly returns to the first shape if an external force is eliminated. As the material of the superelastic wire 331, nickel-titanium alloy or the like may be used.

If necessary, the outer circumference of the superelastic wire 331 may be subjected to coating using a polyurethane tube, a tube made of fluorine resin, or the like. When this happens, the slidability of the superelastic wire 331 can be improved, and accommodation in the withdrawal portion 340 can be carried out with a small force.

The withdrawal portion 340 includes a tubular member 341 through which the conducting wire sheathing body 310 passes, and an attachment 342 which fixes the tubular member 341 to the conducting wire sheathing body 310.

The tubular member 341 has rigidity such that the support 330 can be deformed, and has an inner diameter greater than the outer diameter of the conducting wire sheathing body 310. On the base end side of the tubular member 341, screw threads (not shown) are provided to fix the tubular member 341 to the attachment 342.

The attachment 342 is fixed to the conducting wire sheathing body 310, and thread grooves (not shown) which is engageable with the screw threads of the tubular member 341 are formed in the inner surface on the leading end side of the attachment 342.

With the above-described configuration, when the tubular member 341 is fixed to the attachment 342, the tubular member 341 is held so as not to relatively move in the axial direction thereof with respect to the conducting wire sheathing body 310. When the tubular member 341 is disengaged from the attachment 342, the tubular member 341 can relatively move with respect to the conducting wire sheathing body 310.

An operation at the time of the use of the biological implantable electrode 301 configured as above will be described in connection with an example where the electrode portion 320 is placed in the superior vena cava.

Figure 41:
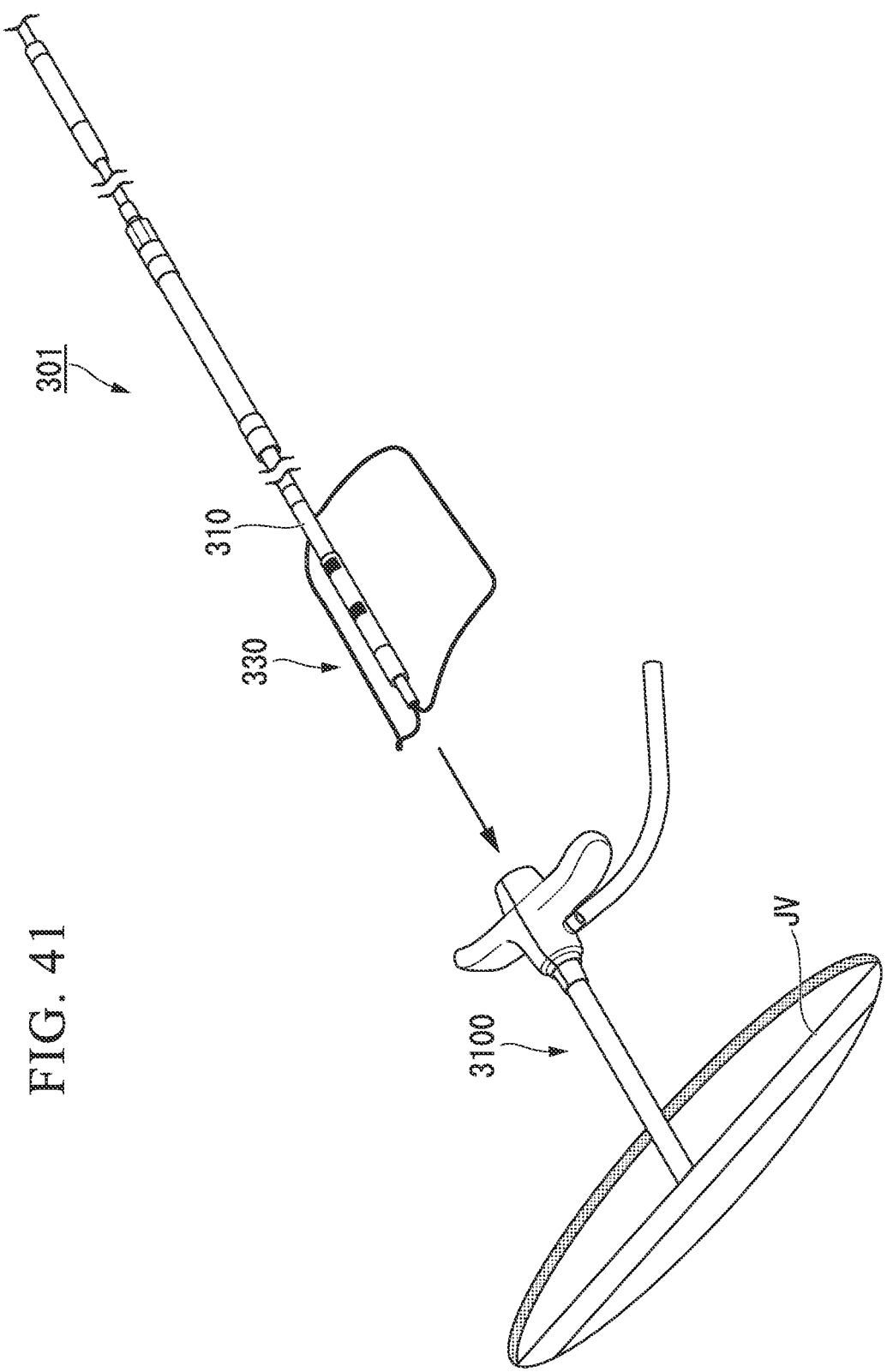
FIG. 41 is a diagram showing an operation at the time of using the biological implantable electrode according to the seventh embodiment of the present invention.

The operator makes an incision on the cervical region of a patient to expose a jugular vein JV. Next, as shown in FIG. 41, the operator makes an incision on the jugular vein JV and inserts the leading end of an introducer 3100 into the jugular vein JV. As the introducer 3100, a known introducer having a check valve is appropriately selected and used in consideration of an inner diameter or the like such that the biological implantable electrode 301 smoothly passes therethrough.

Next, the operator manually folds and deforms the electrode support 330 and inserts the biological implantable electrode 301 into the introducer 3100 (second shape deformation process). In the introducer 3100, the electrode support 330 is deformed to a second shape appropriate for introduction into the vein to follow the conducting wire sheathing body 310. After the electrode support 330 entirely enters the introducer 3100, the operator moves the conducting wire sheathing body 310 into the jugular vein JV through the introducer 3100. The electrode support 330 which passes through the introducer 3100 and protrudes into the jugular vein JV returns to the first shape appropriate for supporting the electrode portion in the biological body (first shape deformation process). The first shape is an arc shape which is made convex toward the electrode portion 320. Since the radius of curvature of the arc is equal to or greater than the average diameter of the jugular vein JV, the electrode support 330 cannot completely return to the first shape, and presses the electrode portion 320 and the inner wall of the jugular vein JV to urge the electrode portion 320 to be in close contact with the inner wall.

When the operator further pushes the biological implantable electrode 301 with constant force, while the electrode support 330 is sliding on the inner wall of the vein, the biological implantable electrode 301 goes forward. The operator moves the electrode portion 320 to a predetermined position of the superior vena cava $V_1$ near the vagus nerve while confirming the position of the electrode portion 320 inside the body of the patient by an X-ray fluoroscopic image or the like.

Figure 42:
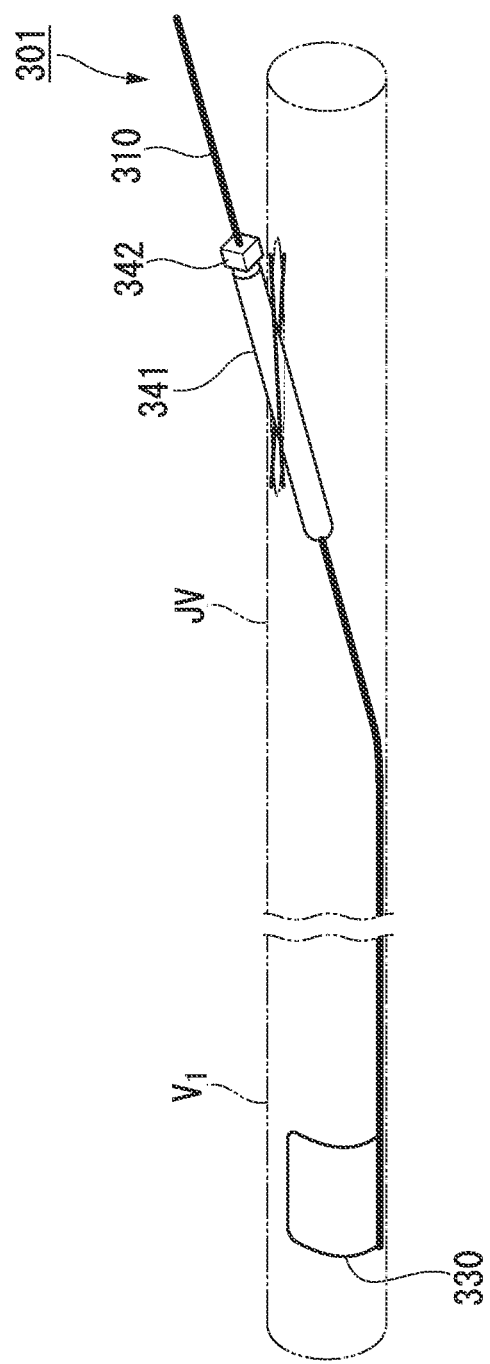
FIG. 42 is a diagram showing an operation at the time of using the biological implantable electrode according to the seventh embodiment of the present invention.

As shown in FIG. 42, in a state where the base end side of the tubular member 341 and the attachment 342 are located outside the jugular vein JV, the operator sutures the jugular vein JV and the cervical region, and ends the placement procedure of the biological implantable electrode 301. The introducer 3100 is withdrawn or torn and removed.

After the biological implantable electrode 301 is placed, the operator connects the electrical stimulus generation device to the conducting wire sheathing body 310 and stimulates the vagus nerve beyond the vascular wall of the superior vena cava $V_1$ to carry out a desired treatment. While the biological implantable electrode 301 is being placed, the position of the electrode portion 320 is suitably maintained by frictional force between the electrode support 330 in the first shape and the vascular wall.

Figure 43:
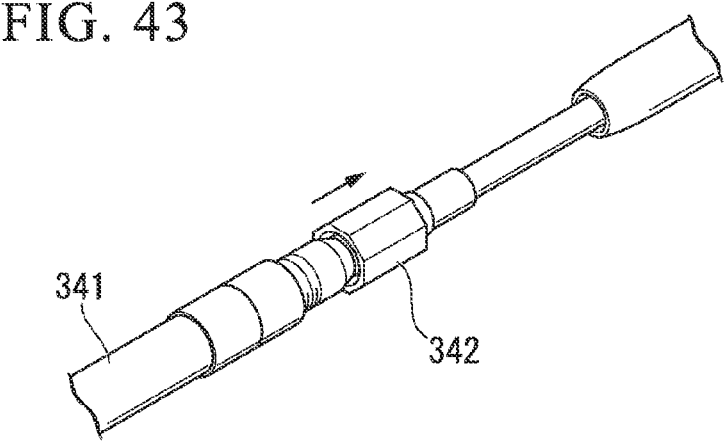
FIG. 43 is a diagram showing an operation at the time of using the biological implantable electrode according to the seventh embodiment of the present invention.
Figure 44:
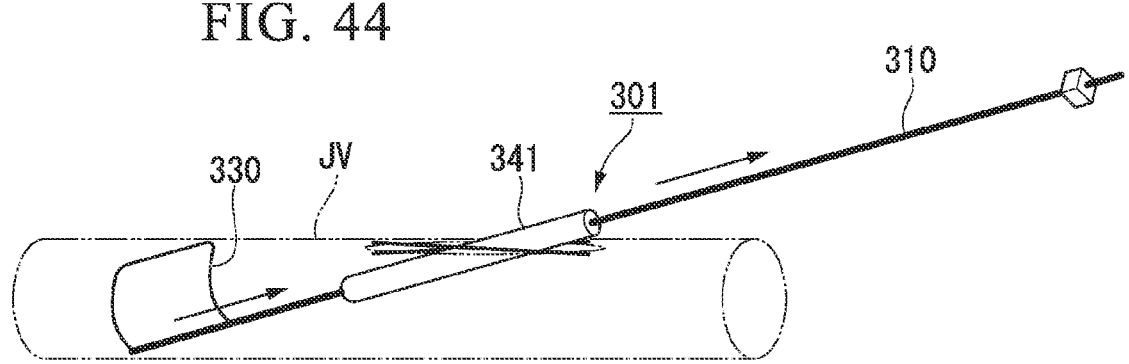
FIG. 44 is a diagram showing an operation at the time of using the biological implantable electrode according to the seventh embodiment of the present invention.
Figure 45:
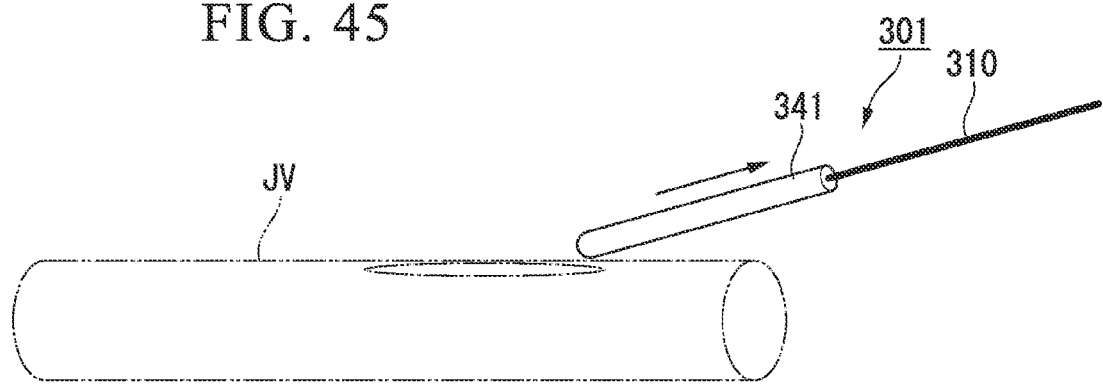
FIG. 45 is a diagram showing an operation at the time of using the biological implantable electrode according to the seventh embodiment of the present invention.

At the time of the end of the treatment period or the like, in withdrawing the biological implantable electrode 301, as shown in FIG. 43, the tubular member 341 is disengaged from the attachment 342. As shown in FIG. 44, the conducting wire sheathing body 310 is drawn out outside the body while the tubular member 341 is being fixed. When the electrode support 330 is drawn and accommodated in the tubular member 341, the electrode support 330 is deformed to the second shape in the tubular member 341 (second shape re-deformation process). In a state where the electrode support 330 is accommodated in the tubular member 341, the operator extracts the suture thread which has fixed the 341, and as shown in FIG. 45, withdraws the biological implantable electrode 301 from the jugular vein JV. After the biological implantable electrode 301 is withdrawn, the operator sutures and completely closes the jugular vein JV and the cervical region.

According to the biological implantable electrode 301 of this embodiment, the electrode support portion 330 can be reversibly deformed between the first shape appropriate for supporting the electrode portion in the biological body and the second shape appropriate for introduction and withdrawal with respect to the biological body. For this reason, at the time of introduction or withdrawal with respect to the vein or the like, the electrode support portion 330 is deformed to the second shape and can be moved in and out through a comparatively small incision portion. At the time of the placement, the electrode support portion 330 is deformed to the first shape, such that the electrode portion 320 can be supported at a predetermined position of the vein or the like. As a result, the electrode portion can be placed in the biological body with a small amount of invasion without using a thoracoscope, a trocar, or the like, and electrical stimulus can be applied to a target portion beyond adjacent tissues. After the treatment, the electrode support portion is again deformed to the second shape, such that the electrode support portion can be easily withdrawn from the biological body without making a large incision on the incision portion which is formed for introduction.

The virtual surface VS which is formed by the electrode support 330 has an arc shape which is made convex toward the electrode portion 320 and has the radius of curvature greater than the average diameter of the vein in which the biological implantable electrode 301 is placed. Therefore, the electrode portion 320 can be constantly urged so as to be in close contact with the vascular wall, and an electrostimulation treatment can be satisfactorily carried out.

The withdrawal portion 340 is provided, such that the electrode support 330 is changed to the second shape without using an introducer, easily withdrawing the biological implantable electrode 301. Since the withdrawal portion 340 includes the attachment 342, the tubular member 341 can be stably maintained until withdrawal without being relatively moved with respect to the conducting wire sheathing body 310.

The withdrawal portion 340 includes the tubular member 341, such that the electrode support 330 can be stabilized to the second shape only by accommodating the electrode support 330 in the tubular member 341. Thus, when the biological implantable electrode 301 is withdrawn, the electrode support 330 returns to the first shape, making it possible to satisfactorily suppress a situation in which stuck blood or the like flies in all directions and making it possible to realize safe use.

[Eighth Embodiment]

Next, a biological implantable electrode according to an eighth embodiment of the present invention will be described with reference to FIGS. 46 to 49. Similarly to the biological implantable electrode of the seventh embodiment, the biological implantable electrode of this embodiment may be used in combination with the electrostimulation system according to each of the first to fourth embodiments of the present invention. A difference between a biological implantable electrode 351 of this embodiment and the biological implantable electrode 301 of the seventh embodiment is the structure of the deformation mechanism. In the following description, the same parts as those described above are represented by the same reference numerals, and overlapping description thereof will be omitted.

Figure 46:
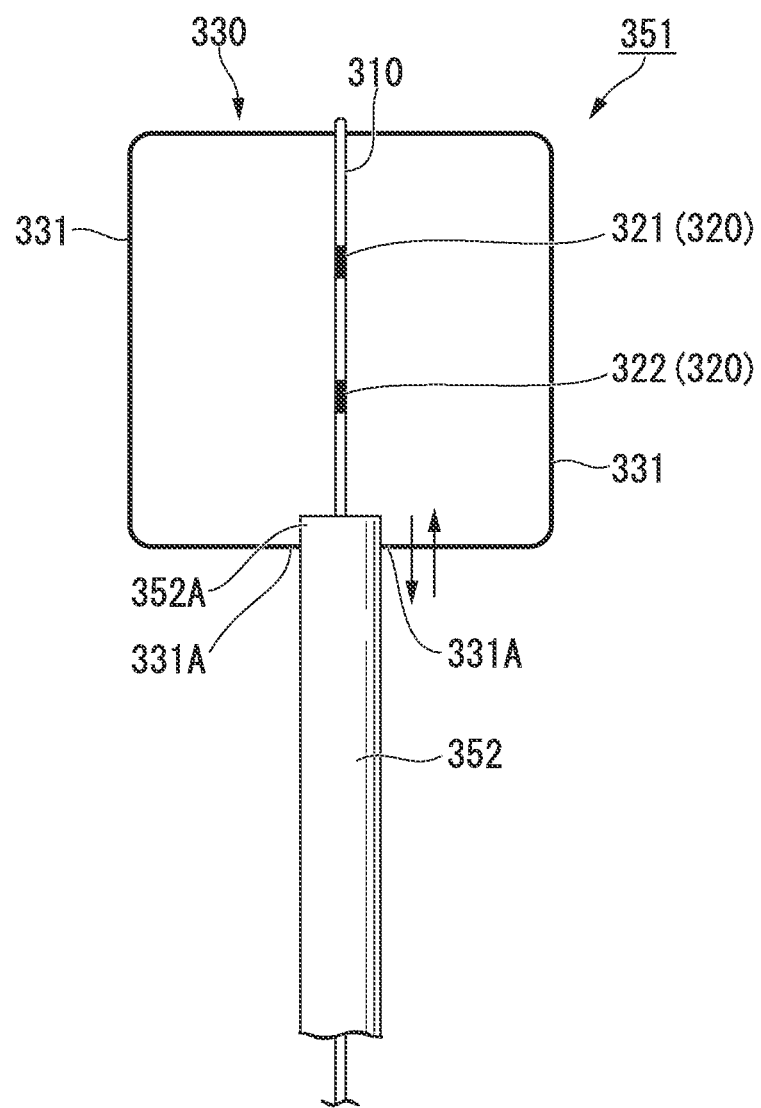
FIG. 46 is a diagram showing the periphery of an electrode portion in a biological implantable electrode according to an eighth embodiment of the present invention.

FIG. 46 is a diagram showing the vicinity of the electrode portion 320 of the biological implantable electrode 351. The biological implantable electrode 351 includes a deformation sheath (deformation mechanism) 352, in place of the withdrawal portion 340. The deformation sheath 352 is formed of the same material as the tubular member 341 but is longer than the tubular member 341, and a leading end portion 352A thereof is located in the vicinity of the electrode portion 320.

A base end portion 331A of a superelastic wire 331 constituting the electrode support 330 is connected to the leading end 352A of the deformation sheath 352. Thus, if the deformation sheath 352 is relatively moved with respect to the conducting wire sheathing body 310, similarly, the base end portion 331A of the superelastic wire 331 is relatively moved with respect to the conducting wire sheathing body 310.

Figure 47:
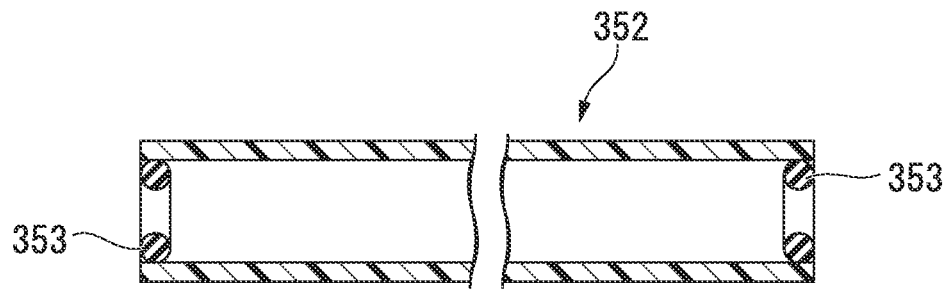
FIG. 47 is a sectional view showing a deformation sheath in the biological implantable electrode according to the eighth embodiment of the present invention.

FIG. 47 is a sectional view of the deformation sheath 352. O rings 353 are attached to both ends of the deformation sheath 352. The inner diameter of each of the O rings 353 is the same (or substantially the same) as the outer diameter of the conducting wire sheathing body 310. When the conducting wire sheathing body 310 passes through the deformation sheath 352, both ends of the deformation sheath 352 are maintained watertight, and blood or the like does not enter the lumen. If force is applied in the axial direction of the deformation sheath 352, contact is maintained between the deformation sheath 352 and the conducting wire sheathing body 310 to an extent such that the deformation sheath 352 can slide on the conducting wire sheathing body 310.

Figure 48:
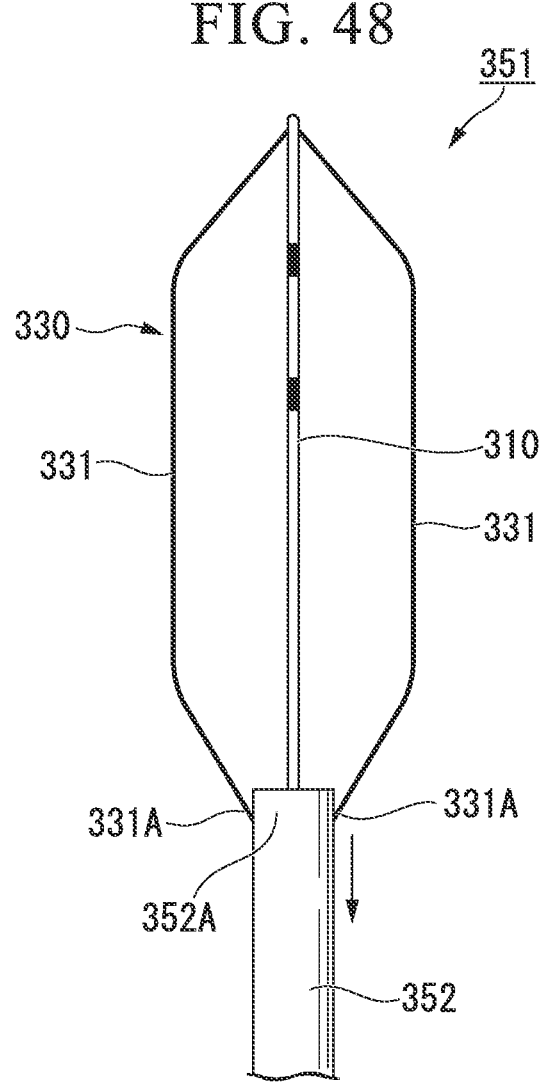
FIG. 48 is a diagram showing an operation at the time of using the biological implantable electrode according to the eighth embodiment of the present invention.
Figure 49:
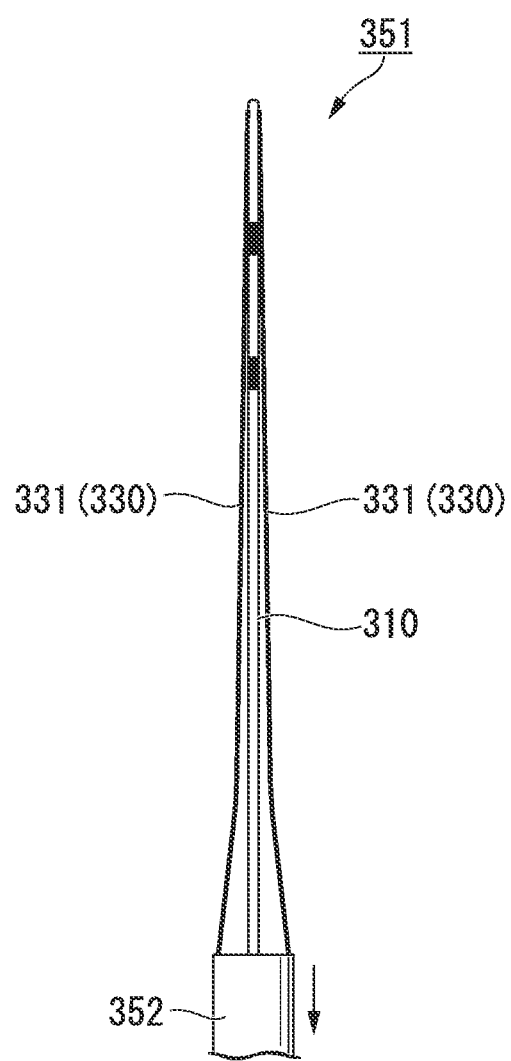
FIG. 49 is a diagram showing an operation at the time of using the biological implantable electrode according to the eighth embodiment of the present invention.

In placing the biological implantable electrode 351 of the embodiment, the operator moves back the deformation sheath 352 with respect to the conducting wire sheathing body 310. When this happens, as shown in FIG. 48, the base end portion 331A of the superelastic wire 331 is moved back with respect to the conducting wire sheathing body 310, and the electrode support 330 is drawn out in the longitudinal direction of the conducting wire sheathing body 310. Finally, as shown in FIG. 49, the electrode support 330 is deformed to the second shape substantially parallel to the conducting wire sheathing body 310. The operator inserts the electrode support 330 in the second shape into the introducer 3100. The timing at which the electrode support 330 is inserted into the introducer 3100 should not be when the electrode support 330 is completely deformed to the second shape, and may be appropriately adjusted.

Although the flow in which the electrode support 330 protrudes from the 3100 and is completely placed is the same as in the first embodiment, in the biological implantable electrode 351, the positional relationship between the deformation sheath 352 and the conducting wire sheathing body 310 is maintained, maintaining the electrode support 330 in the second shape even in the vein. For this reason, in a state where the electrode support is in the second shape, the electrode portion 320 can be moved to the placement portion.

In withdrawing the biological implantable electrode 351, similarly to the insertion, the deformation sheath 352 is moved back to deform the electrode support 330 to the second shape. The electrode support 330 which is deformed to the second shape can be easily withdrawn even through a small incision portion.

In the biological implantable electrode 351 of this embodiment, similarly to the biological implantable electrode 301 of the seventh embodiment, placement and withdrawal can be easily carried out with respect to the biological body with a small amount of invasion.

Since the deformation sheath 352 is provided, and the base end portion 331A of the superelastic wire 331 is connected to the deformation sheath, when the deformation sheath 352 is relatively moved with respect to the conducting wire sheathing body 310, it is possible to easily switch the electrode support between the first shape and the second shape. Thus, the electrode support can be smoothly inserted into an introducer or the like and can be maintained in the second shape in the vein or the like. As a result, it is possible to reduce damage to the inner wall or the like of the vein, realizing a biological implantable electrode with a smaller amount of invasion.

Since the O rings 353 are attached to both ends of the deformation sheath 352, both end portions of the deformation sheath 352 through which the conducting wire sheathing body 310 passes are maintained watertight. Therefore, it is possible to prevent blood or the like from leaking outside the body through the lumen of the deformation sheath 352 or flying in all directions, and making it possible to realize safe use.

From the viewpoint of stable motion of the conducting wire sheathing body, the O rings 353 are preferably at both ends of the deformation sheath 352. However, if watertightness is maintained at least at one place of the lumen of the deformation sheath 352, leakage of blood or the like is prevented. Thus, an O ring is preferably provided at least at one place, and the arrangement portion may not be the end portion.

[Ninth Embodiment]

Next, a biological implantable electrode according to a ninth embodiment of the present invention will be described with reference to FIGS. 50 to 54. Similarly to the biological implantable electrode of the seventh embodiment and the biological implantable electrode of the eighth embodiment, the biological implantable electrode of this embodiment may be used in combination with the electrostimulation system according to each of the first to fourth embodiments of the present invention. A difference between a biological implantable electrode 361 of this embodiment and the biological implantable electrode of each of the foregoing embodiments is in that the biological implantable electrode itself does not include a deformation mechanism.

Figure 50:
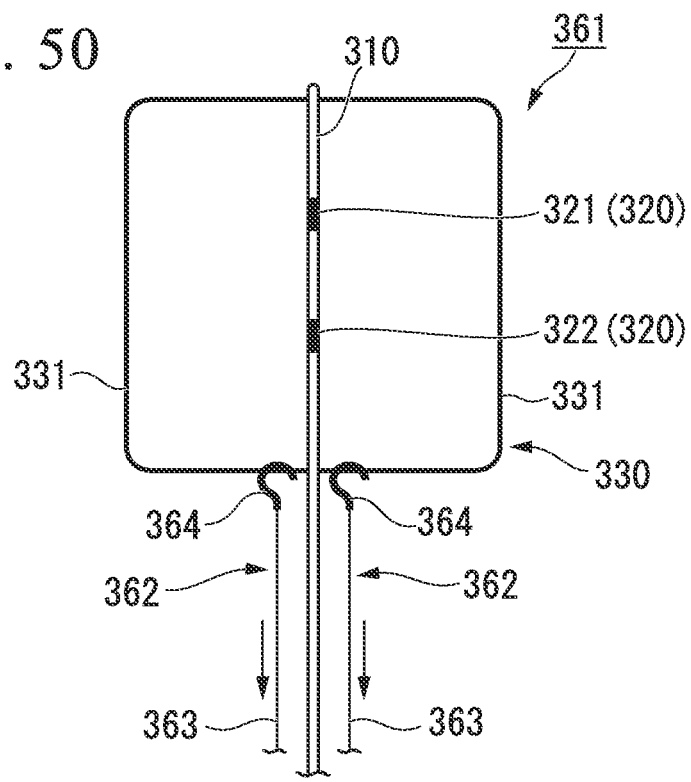
FIG. 50 is a diagram showing the periphery of an electrode portion in a biological implantable electrode according to a ninth embodiment of the present invention.

FIG. 50 is a diagram showing the vicinity of the electrode portion 320 of the biological implantable electrode 361 on a magnified scale. Similarly to the biological implantable electrode 301 of the seventh embodiment, the biological implantable electrode 361 includes the conducting wire sheathing body 310, the electrode portion 320, and the electrode support 330, and is different from the biological implantable electrode 301 in that the withdrawal portion 340 is not provided.

In placing the biological implantable electrode 361, as in the seventh embodiment, the electrode support 330 is deformed and inserted into the introducer 3100.

In withdrawing the biological implantable electrode 361, two towing tools (deformation mechanism) 362 shown in FIG. 50 are inserted into the vein. Each of the towing tools 362 includes a linear portion 363 which is constituted by a wire or the like having predetermined rigidity and a locking portion 364 which is provided at the leading end of the linear portion 363. The operator moves forward the towing tools 362 and locks the locking portion 364 of each towing tool 362 to the base end side of each superelastic wire 331 of the electrode support 330 while confirming using an X-ray fluoroscopic image.

Figure 51:
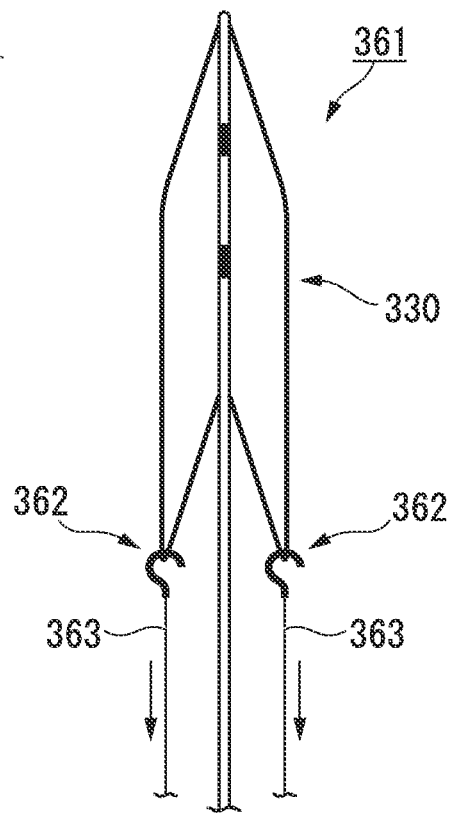
FIG. 51 is a diagram showing an operation at the time of using the biological implantable electrode according to the ninth embodiment of the present invention.
Figure 52:
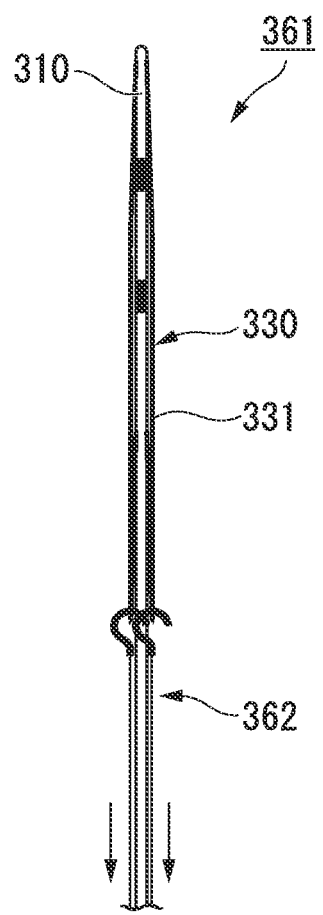
FIG. 52 is a diagram showing an operation at the time of using the biological implantable electrode according to the ninth embodiment of the present invention.

After it is confirmed that the locking portions 364 are locked to the superelastic wires 331, the operator tows so as to move back the linear portions 363. When this happens, as shown in FIG. 51, the electrode support 330 is towed by the towing tools 362, is gradually deformed, and as shown in FIG. 52, is deformed to the second shape. Thereafter, the biological implantable electrode 361 is withdrawn in the same procedure as in the eighth embodiment.

In the biological implantable electrode 361 of the embodiment, similarly to the biological implantable electrode of each of the seventh and eighth embodiments, placement and withdrawal can be easily carried out with respect to the biological body with a small amount of invasion.

Since the towing tools 362 serving as a deformation mechanism is provided separately from the biological implantable electrode 361, the biological implantable electrode itself can be reduced in diameter, and can be placed in the body through a smaller incision portion.

Figure 53:
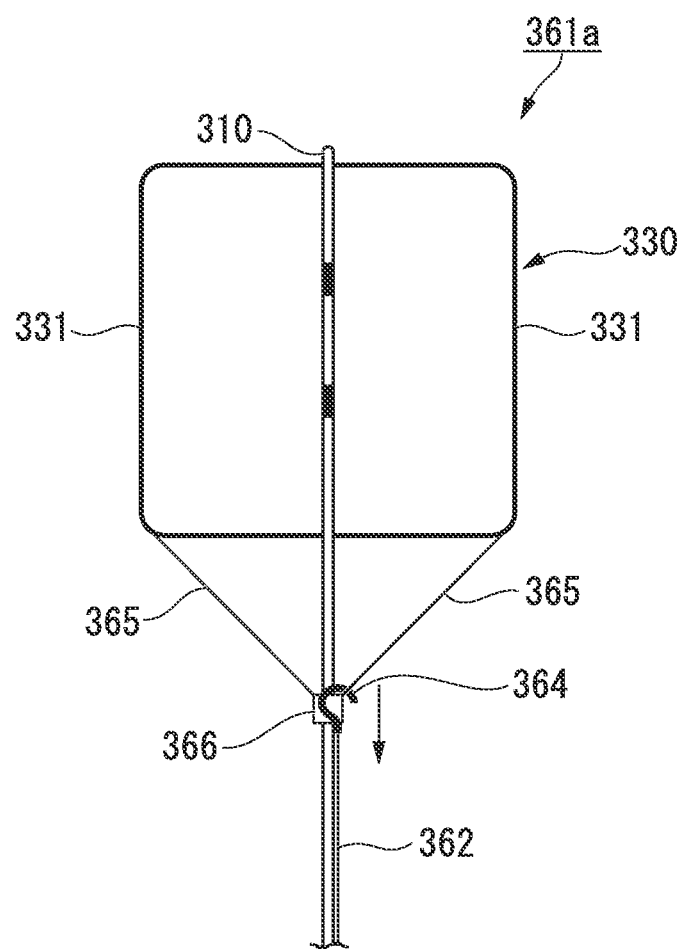
FIG. 53 is a diagram showing an operation at the time of using a modification of the biological implantable electrode according to the ninth embodiment of the present invention.

Although in this embodiment, an example has been described where, at the time of withdrawal, the two towing tools 362 are used, as in a modification shown in FIG. 53, a single towing tool 362 may be used to deform the electrode support.

In a biological implantable electrode 361a shown in FIG. 53, an auxiliary wire 365 is attached at a position most distant from the conducting wire sheathing body 310 on the base end side of each superelastic wire 331 of the electrode support 330. The base end side of each auxiliary wire 365 is connected to a movable member 366 which is slidably attached to the conducting wire sheathing body 310.

Figure 54:
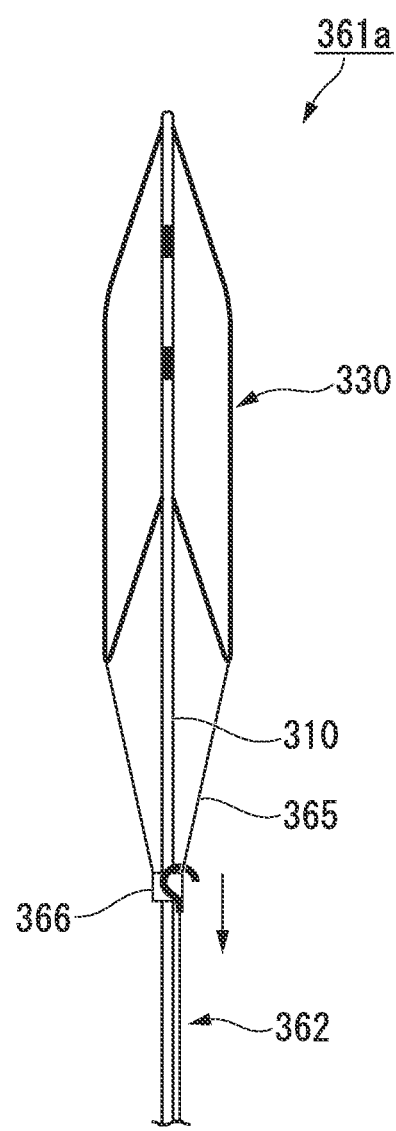
FIG. 54 is a diagram showing an operation at the time of using a modification according to the ninth embodiment of the present invention.
Figure 55:
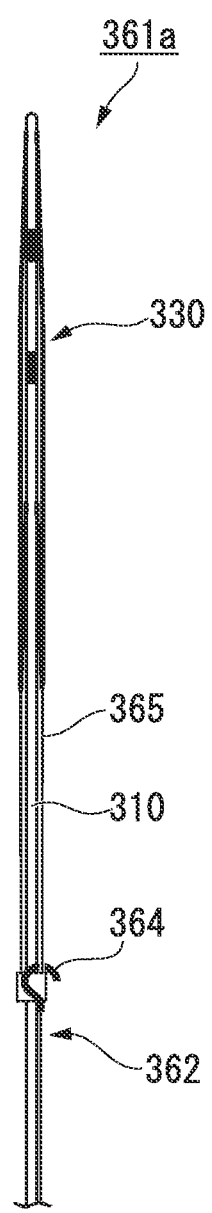
FIG. 55 is a diagram showing an operation at the time of using a modification according to the ninth embodiment of the present invention.

In withdrawing the biological implantable electrode 361a, the operator locks the locking portion 364 of the towing tool 362 to the movable member 366 or the auxiliary wire 365 in the vicinity of the movable member 366 and carries out towing. The movable member 366 towed by the towing tool 362 slides to the base end side along the conducting wire sheathing body 310. As a result, as shown in FIG. 54, the electrode support 330 is deformed, and finally, as shown in FIG. 55, the electrode support 330 is deformed to the second shape.

In the biological implantable electrode 361a of this modification, withdrawal can be carried out using a single towing tool, such that an operation at the time of withdrawal is more facilitated. The movable member 366 to which the locking portion 364 of the towing tool 362 is locked has the maximum dimension in the width direction greater than the superelastic wire 331 or the auxiliary wire 365, and is easily confirmed under an X-ray fluoroscope or the like.

In this modification, the movable member 366 may be provided distant from the conducting wire sheathing body 310. While the movable member 366 is not provided, both ends of a single auxiliary wire 365 may be connected to the superelastic wires 331. Even in this case, similarly, the towing tool 362 or the like is locked to the auxiliary wire 365, such that the electrode support 330 can be deformed.

[Tenth Embodiment]

Figure 57:
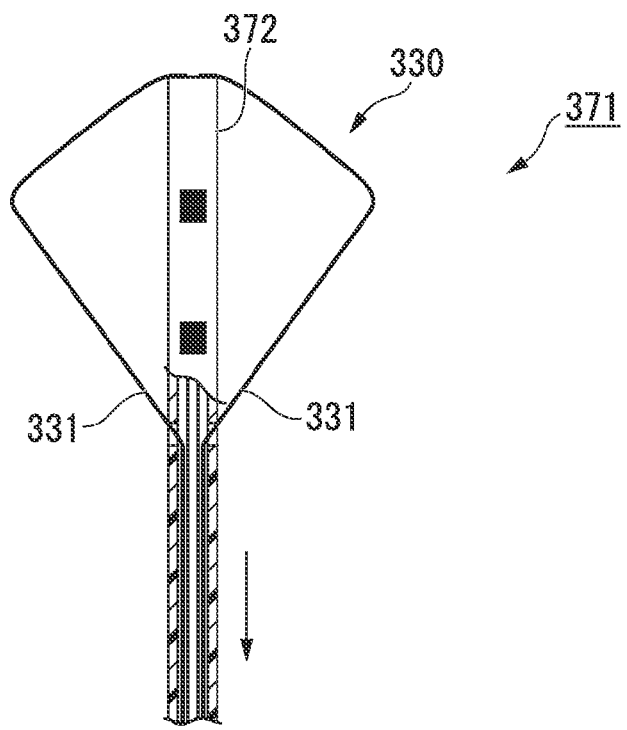
FIG. 57 is a diagram showing an operation at the time of using the biological implantable electrode according to the tenth embodiment of the present invention.
Figure 58:
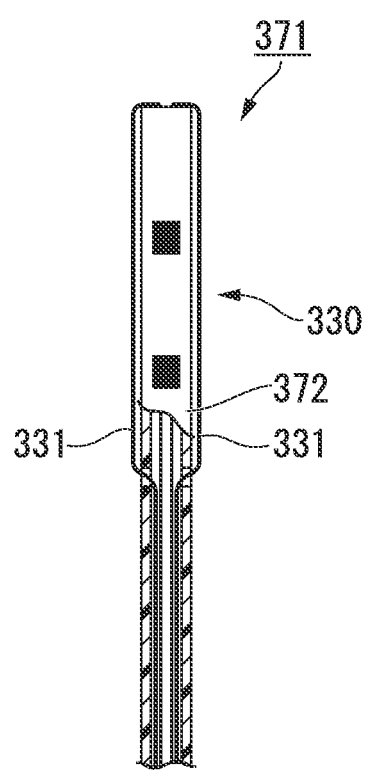
FIG. 58 is a diagram showing an operation at the time of using the biological implantable electrode according to the tenth embodiment of the present invention.

Next, a biological implantable electrode according to a tenth embodiment of the present invention will be described with reference to FIGS. 56 to 58. Similarly to the biological implantable electrode of the seventh embodiment, the biological implantable electrode of the eighth embodiment, and the biological implantable electrode of the ninth embodiment, the biological implantable electrode of this embodiment may be used in combination with the electrostimulation system according to each of the first to fourth embodiments of the present invention. A difference between a biological implantable electrode 371 of this embodiment and the biological implantable electrode of each of the foregoing embodiments is a structure to deform the electrode support 330.

Figure 56:
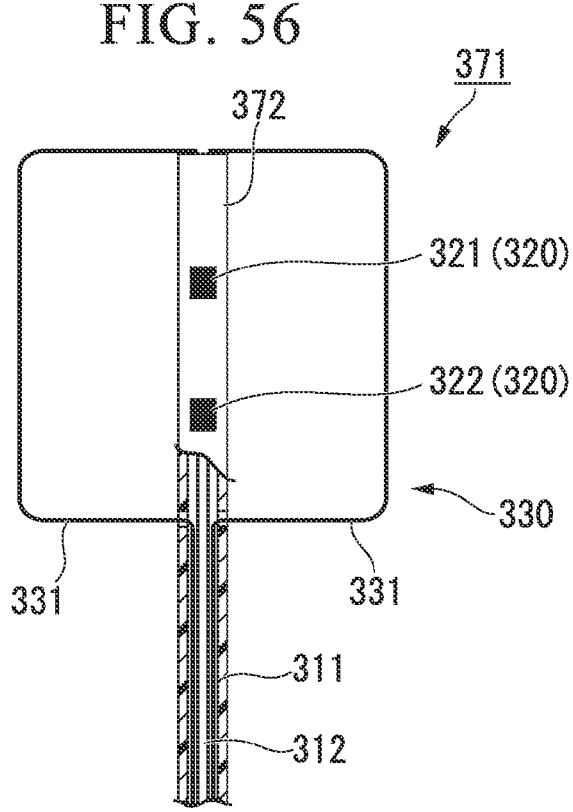
FIG. 56 is a diagram showing the periphery of an electrode portion in a biological implantable electrode according to a tenth embodiment of the present invention.

FIG. 56 is a diagram showing the vicinity of the electrode portion 320 of the biological implantable electrode 371 in partial sectional view. Although the basic structure of the conducting wire sheathing body 372 is the same as the above-described conducting wire sheathing body 310, in this embodiment, for ease of understanding of the internal structure, the dimension in the radial direction is magnified.

The base end side of each superelastic wire 331 of the electrode support 330 is inserted into a space between the insulating layer 311 and the conducting wire 312 inside the conducting wire sheathing body 372, and protrudes from the base end side of the conducting wire sheathing body 372 through the conducting wire sheathing body 372.

In deforming the electrode support 330 to the second shape, the base end side of each superelastic wire 331 is towed. When this happens, as shown in FIG. 57, the superelastic wire 331 is drawn and deformed in the conducting wire sheathing body 372. Finally, as shown in FIG. 58, the electrode support 330 is deformed to the second shape according to the conducting wire sheathing body 372.

In the biological implantable electrode 371 of this embodiment, similarly to the biological implantable electrode of each of the foregoing embodiments, placement and withdrawal can be easily carried out with respect to the biological body with a small amount of invasion.

The electrode support 330 can be deformed by operating the base end sides of the superelastic wires 331 protruding from the base end side of the conducting wire sheathing body 372. Thus, complex preparation working is not required before the electrode support 330 is deformed, and the shape of the electrode support can be easily switched.

The embodiments of the invention have been described, the technical scope of the invention is not limited to the embodiments, the combination of the constituent elements of each embodiment may be changed or the respective constituent elements may be changed or eliminated without departing from the spirit and scope of the invention.

For example, although in the foregoing embodiments, an example has been described where an electrode support is formed by two superelastic wires, one superelastic wire may be used to form the above-described virtual surface VS, thereby constituting an electrode support.

[Eleventh Embodiment]

Next, an electrostimulation system according to an eleventh embodiment of the present invention will be described with reference to FIGS. 59 to 69. The electrostimulation system is placed in a vein of a patient for a certain period and used to apply an electrical stimulus to a nervous tissue around the vein through a tube wall of the vein.

Figure 59:
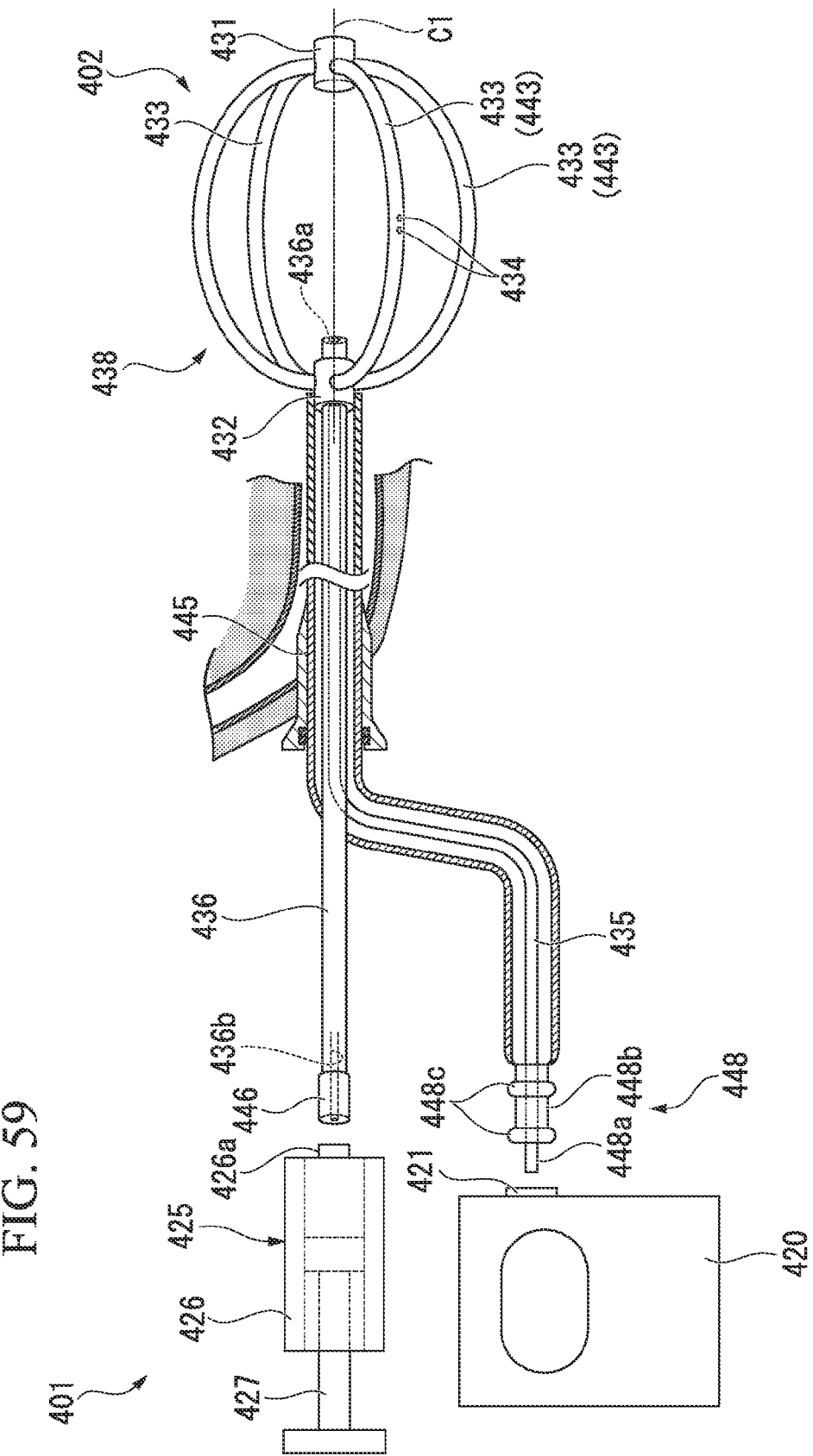
FIG. 59 is a side view of an electrostimulation system according to an eleventh embodiment of the present invention, a portion of which is broken out.
Figure 60:
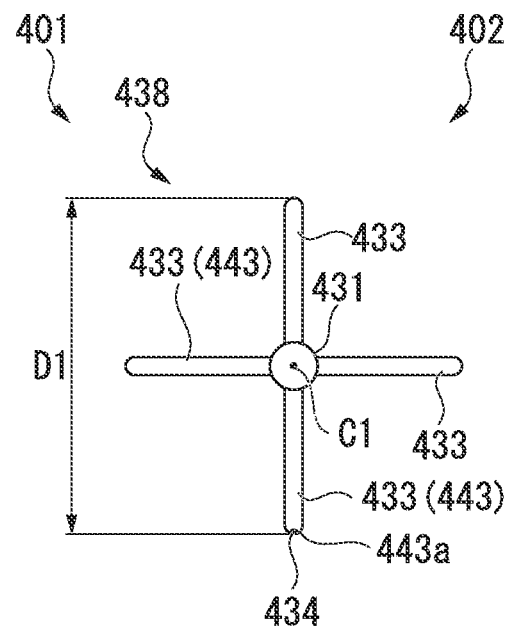
FIG. 60 is a front view of the electrostimulation system according to the eleventh embodiment of the present invention.

As shown in FIGS. 59 and 60, an electrostimulation system 401 of the embodiment includes an electrode unit 402 configured to place a leading end portion into the vein, and an electrostimulation device (a stimulus generating unit) 420 and a syringe piston pump (a liquid medicine supply unit) 425 detachably attached to the electrode unit 402 and installed at the outside of the body.

The electrode unit 402 includes a leading end attachment 431 and a base end attachment 432 disposed to be spaced apart from each other, four wire portions (support portions) 433 having end portions connected to the leading end attachment 431 and the base end attachment 432, a pair of stimulation electrodes 434 installed at one of the four wire portions 433, an interconnection portion 435 having a leading end portion electrically connected to the stimulation electrodes 434, and a liquid feed tube 436 disposed to extend along the interconnection portion 435.

In this embodiment, the attachments 431 and 432 are formed of a material having biocompatibility such as stainless steel, titanium, or the like, in a substantially columnar shape. The leading end attachment 431 is disposed at a position closer the leading end side than the base end attachment 432.

Figure 61:
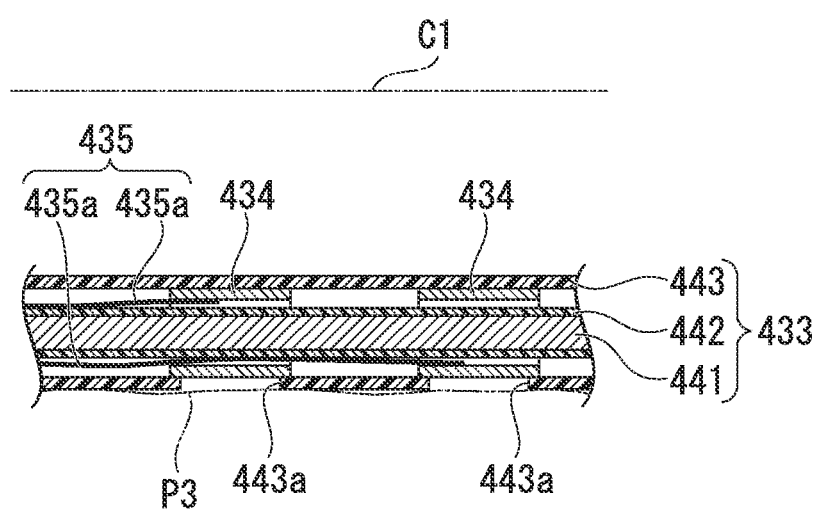
FIG. 61 is a cross-sectional view of a wire portion of the electrostimulation system according to the eleventh embodiment of the present invention.
Figure 62:
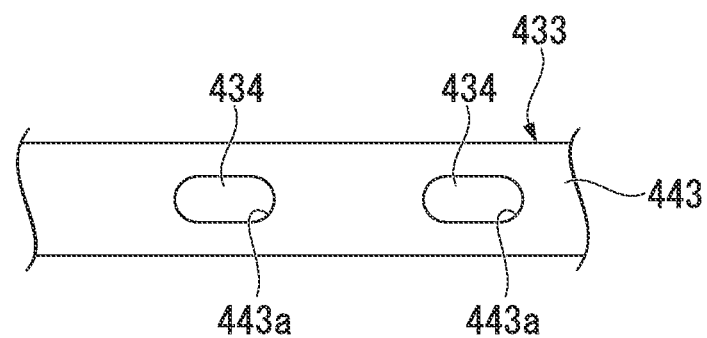
FIG. 62 is a side view of the wire portion of the electrostimulation system according to the eleventh embodiment of the present invention.

As shown in FIG. 61, the wire portion 433 has a wire 441 installed at a center thereof, an inner capsule 442 configured to cover an outer circumferential surface of the wire 441, and an outer capsule 443 configured to cover the outer circumferential surface of the inner capsule 442.

The wire 441 may be formed by appropriately using a material, for example, a shape memory alloy, a superelastic wire, or the like, which returns to its original shape without plastic deformation when the external force is released after an external force is applied to the wire 441 in a natural state in which no external force except for gravity is applied. An outer diameter of the wire 441 is set to, for example, φ0.2 to 0.5 mm.

The capsules 442 and 443 are formed of a resin such as polyurethane or the like and have a thickness of 50 to 500 μm. According to the above-mentioned configuration, the outer circumferential surface of the outer capsule 443 becomes smooth, and generation of thrombus on the outer circumferential surface is prevented.

When a linear axis C1 (see FIG. 59) passing through the leading end attachment 431 and the base end attachment 432 is defined, a pair of through holes 443a are formed parallel to an axis C1 direction in the outer capsule 443 at an opposite side of the axis C1 of an intermediate portion in the axis C1 direction of the outer capsule 443. When seen from a side view of FIG. 62, the through holes 443a are formed in a substantially oval shape, which is long in the axis C1 direction. A size of the through hole 443a has, for example, a major axis of 1.8 mm and a minor axis of 0.5 mm. A distance in the axis C1 direction of a center portion of the pair of through holes 443a is set to about 3 to 5 mm.

As shown in FIG. 61, the above-mentioned stimulation electrode 434 having a cylindrical shape is installed between the inner capsule 442 and the outer capsule 443. The stimulation electrode 434 has, for example, an outer diameter of about 1 mm and a length of about 2 mm, and is formed of a platinum-iridium alloy or the like. The pair of stimulation electrodes 434 are installed at the wire portion 433. The inner capsule 442 is inserted into the stimulation electrode 434, and the stimulation electrode 434, which functions to cover the through hole 443a, is exposed to the outside.

An electrical interconnection 435a constituting the interconnection portion 435 is electrically connected to an inner circumferential surface of the stimulation electrode 434. An interconnection in which a stranded wire formed of a nickel-cobalt alloy (35NLT material) having flex resistance is coated with an electrical insulating material (for example, ETFE (polytetrafluoroethylene) of a thickness of 20 μm, or the like) can be appropriately used as the electrical interconnection 435a.

The electrical interconnection 435a is disposed in the outer capsule 443 to extend along the outer capsule 443, and passes through the base end attachment 432 to further extend to the base end side.

As shown in FIGS. 59 and 60, the wire portion 433 is formed of an elastic material and has an arcuate shape, a central angle of which is about 180° as a whole. A radius of the wire portion 433 is set to about 10 to 20 mm according to an inner diameter of the placed vein.

In this embodiment, the four wire portions 433 are disposed about the axis C1 at the same angle. That is, the wire portions 433 are disposed such that the intermediate portions in the axis C1 direction are curved to be spaced apart from the axis C1 and the intermediate portions are spaced part from each other about the axis C1. The four wire portions 433 are disposed on a spherical surface.

The four wire portions 433 and the attachments 431 and 432 constitute an electrode portion 438.

An outer diameter D1 of the electrode portion 438 in a natural state is about 20 to 40 mm. The outer diameter D1 is set to be larger than the inner diameter of the vein in which the electrode portion 438 is placed.

The wire portion 33 is joined with the attachment 31 and 32 through welding, bonding, caulking, or the like.

Figure 63:
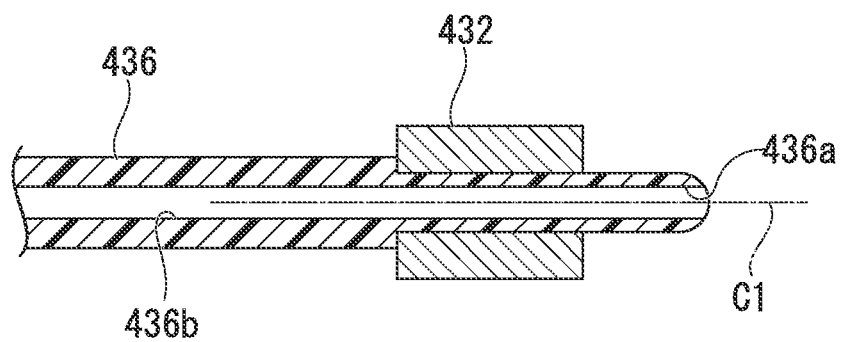
FIG. 63 is a cross-sectional view of major parts of the electrostimulation system according to the eleventh embodiment of the present invention.

As shown in FIGS. 59 and 63, a leading end portion of the liquid feed tube 36 passes through the base end attachment 432. The liquid feed tube 436 has an opening 436a in front of the base end attachment 432. The opening 436a is disposed on the axis C1. A cross section of an inner surface of a pipeline 436b of the liquid feed tube 436 perpendicular to the axis C1 has a circular shape. The liquid feed tube 436 may be formed of a resin, for example, ETFE, or the like.

A leading end portion of a tubular lead main body 445 is attached to the base end attachment 432. A portion of the lead main body 445 corresponding to a length placed in the vein (a length of about 40 to 200 mm from the base end attachment 432) is formed of a flexible material, for example, silicon having a hardness of about A50°, and a base end side from the end portion is formed of a hard material, for example, polyurethane having a hardness of about D60°. Upon placement of the electrode, while a lead manipulation by an operator from the outside of the body is needed, a portion manipulated by the operator may be formed of a hard material such that a stimulation electrode is easily guided to a desired position. In addition, as a flexible material is used for the portion corresponding to the inside of the vein, movement of a position of the stimulation electrode due to a body motion can be prevented. A lead has, for example, an outer diameter of about 2 to 3 mm and a length of about 500 mm.

The above-mentioned interconnection portion 435 and the liquid feed tube 436 are inserted into the lead main body 445. The base end side of the liquid feed tube 436 is configured to protrude from a side surface of the lead main body 445, and a connector 446 including a Luer lock is attached to the base end portion of the liquid feed tube 436. A portion of the lead main body 445, from which the liquid feed tube 436 protrudes, is a portion positioned at the outside of the body of the patient when the electrode portion 438 is placed in the vein.

For example, a known IS1 type connector 448 installed at the base end portion of the lead main body 445, and the base end portion of the interconnection portion 435 is electrically connected to the connector 448.

The connector 448 includes a connector pin 448a for a negative electrode and a connector pin 448b for a positive electrode, and a pair of rubber rings 448c. The rubber rings 448c insulate the connector pin 448a for the negative electrode and the connector pin 448b for the positive electrode from each other, and remain watertight upon connection to the electrostimulation device 420. Both of the connector pin 448a for the negative electrode and the connector pin 448b for the positive electrode are formed of stainless steel. In addition, the rubber rings 448c are formed of silicon rubber having biocompatibility. A waterproof connector can be used as the connector 448 when the electrostimulation device 420 is installed at the outside of the body, in addition to the IS1 type.

A sheath for withdrawal having a length of 3 to 5 cm is installed at the outside of the lead main body 445. The sheath for withdrawal is slidable with respect to the lead main body in the axial direction. In the sheath for withdrawal, an end surface in a leading end portion direction has an acute tapered shape, an end surface in a base end portion direction has a flange shape, and an O-ring is installed in the flange to prevent exposure of blood. Hard polyethylene or polyurethane is appropriate for a material of the sheath.

Figure 64:
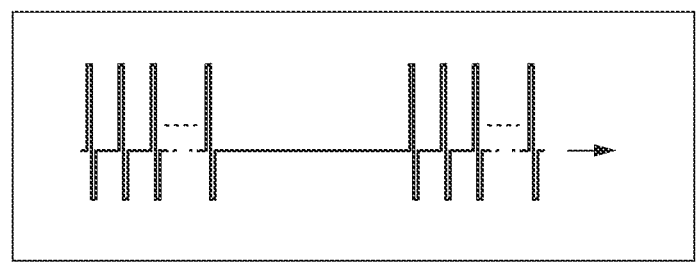
FIG. 64 is a view showing an example of a waveform generated by an electrostimulation device of the electrostimulation system according to the eleventh embodiment of the present invention.

The electrostimulation device 420 has an electrical stimulus supply unit (not shown), and can generate an electrical stimulus according to a constant current type or a constant voltage type. In this embodiment, as an electrical stimulus, as shown in FIG. 64, biphasic waveform groups of the constant voltage type having a changing phase are generated at predetermined time intervals. As an example of a specific biphasic waveform, for example, a voltage can be exemplarily varied between plus several volts to minus several volts at a frequency of 20 Hz and a pulse width of 50 to 400 μsec. The electrostimulation device 420 generates the biphasic waveform for 3 to 10 seconds per minute. In addition, in the case of arrhythmia treatment, the biphasic waveform may be continuously generated.

As shown in FIG. 59, the electrostimulation device 420 is detachably configured at the base end portion of the interconnection portion 435 by a connector 421 included in the electrostimulation device 420 and the above-mentioned the connector 448. Then, when both of the connectors 421 and 448 are connected, the electrostimulation device 420 can apply the above-mentioned biphasic waveform between the pair of stimulation electrodes 434 installed at the wire portions 433. Here, one stimulation electrode 434 of the pair of stimulation electrodes 434 acts as a plus-side electrode, and the other stimulation electrode 434 acts as a minus-side electrode.

The syringe piston pump 425 has a known configuration, and a piston 427 is slidable with respect to a syringe 426. An inlet port 426a formed at a leading end portion of the syringe 426 is detachable and attachable with respect to the connector 446 of the liquid feed tube 436. An anticoagulant agent such as heparin, argatroban, or the like, or a diluted solution thereof is accommodated in the syringe 426, and as the piston 427 is pushed into the syringe 426 in a state in which the inlet port 426a is mounted on the connector 446, the anticoagulant agent can be supplied into the pipeline 436b of the liquid feed tube 436 through the inlet port 426a.

Next, a procedure of placing the electrode portion 438 of the electrode unit 402 into the superior vena cava will be described using the electrostimulation system 401 configured as above. In this case, an outer diameter D1 in a natural state of the electrode portion 438 is set to be larger than the inner diameter of the superior vena cava. In the electrostimulation system 401 to be described below, in an initial state, the electrostimulation device 420 and the syringe piston pump 425 are not mounted.

In addition, the electrostimulation system 401 is appropriate to perform a temporary nerve stimulus for a short amount of time, unlike a long-term nerve stimulation system in which the entire system is implanted in the body.

Figure 65:
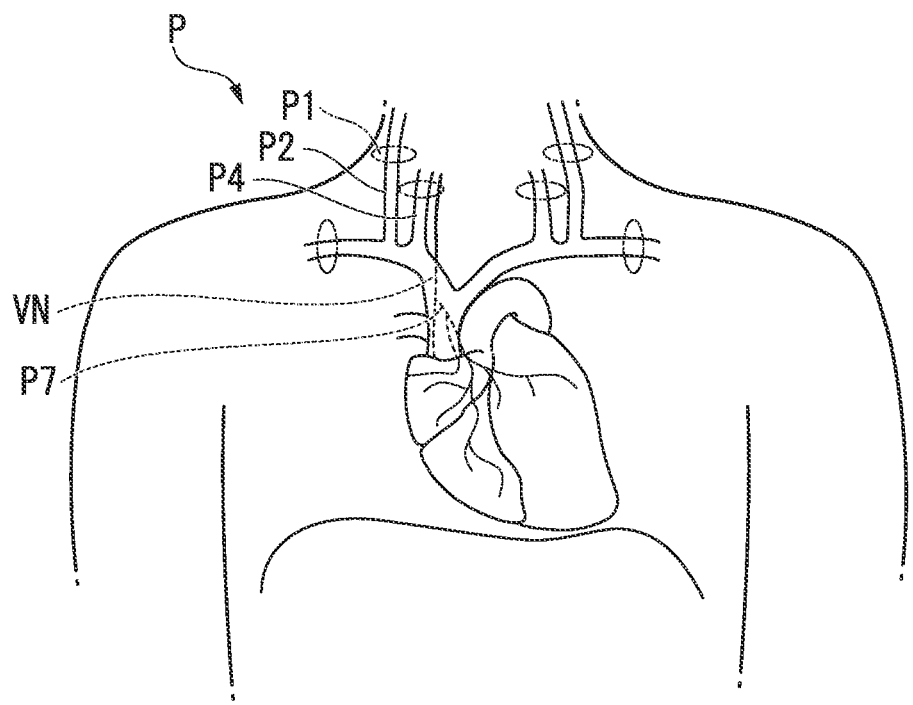
FIG. 65 is a view for explaining a position of an opening formed in a patient.

First, as shown in FIG. 65, the operator performs a small incision of the skin in the vicinity of the right of the neck of a patient P, and forms an opening P1. The electrode portion 438 of the electrode unit 402 is firstly introduced into the external jugular vein P2 or the internal jugular vein P4 via a known introducer or a dilator (not shown) from the opening P1. In this case, as a position of the wire 441 or the interconnection portion 435 of the wire portion 433 is checked under an X-ray, the electrode portion 438 of the electrode unit 402 is introduced while checking a position of the electrode unit 402. In addition, the insertion position is not limited thereto but insertion from the left of the neck, the right subclavian vein or the left subclavian vein may also be performed.

Figure 66:
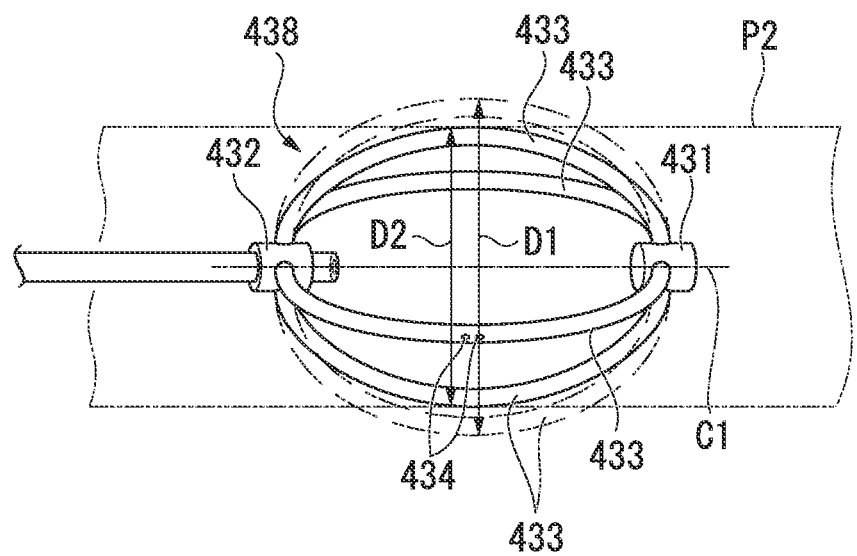
FIG. 66 is a view for explaining a state in which an electrode portion of the electrostimulation system according to the eleventh embodiment of the present invention is introduced into the vein.

When the electrode portion 438 is introduced into the external jugular vein P2, as shown in FIG. 66, the respective wire portions 433 are elastically deformed to the axis C1 side and reduced in diameter throughout the electrode portion 438 as they are pushed into the inner wall of the external jugular vein P2, and extend in the axis C1 direction. Accordingly, an outer diameter D2 of the electrode portion 438 is smaller than the outer diameter D1 in the natural state.

Figure 67:
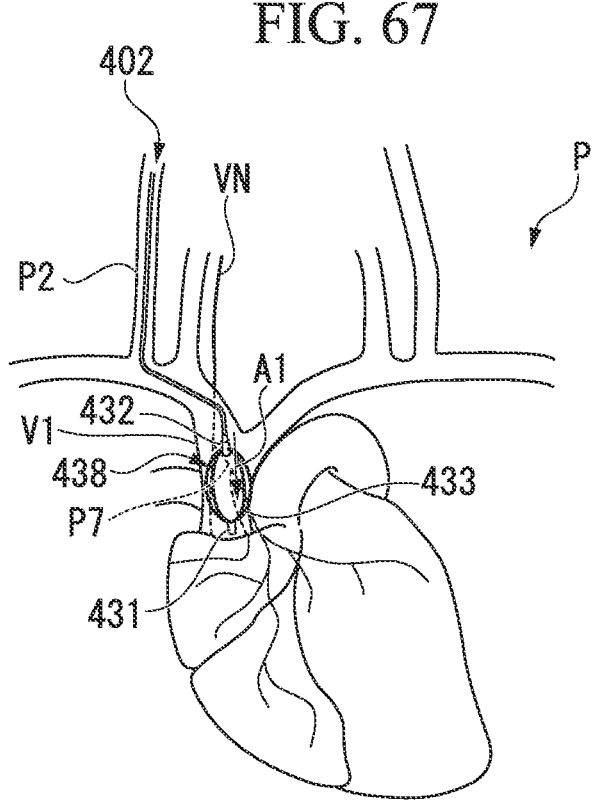
FIG. 67 is a view for explaining a state in which an electrode portion of the electrostimulation system according to the eleventh embodiment of the present invention is placed in the superior vena cava.

The operator introduces the electrode unit 402 while checking the position under the X-ray, and as shown in FIG. 67, the electrode portion 438 is roughly disposed at the superior vena cava $V_1$. Even in this case, since the outer diameter D1 of the electrode portion 438 is set as described above, the wire portions 433 are pushed to the axis C1 side by the superior vena cava $V_1$, and as shown in FIG. 61, the stimulation electrodes 434 exposed from the through hole 443a are disposed to oppose the inner wall of the superior vena cava $V_1$.

As shown in FIG. 67, a vagus nerve (a nervous tissue) VN and a cardiac branch of the vagus nerve P7 near the superior vena cava $V_1$ keep pace in parallel with each other.

Next, in the outside of the body of the patient P, the connector 448 of the interconnection portion 435 and the connector 421 of the electrostimulation device 420 are connected to each other, and a biphasic waveform group is generated from the electrostimulation device 420 to be applied between the pair of stimulation electrodes 434.

The operator manipulates the lead main body 445 and adjusts a position in a longitudinal direction of the superior vena cava $V_1$ in the electrode portion 438, and measures a heart rate by an electrocardiograph or the like attached to the patient P while rotating the lead main body 445 about the axis C1. When the pair of stimulation electrodes 434 are disposed to approach and oppose the vagus nerve VN or the cardiac branch of the vagus nerve P7 and an electrical stimulus transmitted to the vagus nerve VN or the cardiac branch of the vagus nerve P7 from the pair of stimulation electrodes 434 is increased, the heart rate of the patient P is extremely decreased. The operator adjusts a direction about the axis C1 of the electrode portion 438 to extremely decrease the heart rate, i.e., such that the pair of stimulation electrodes 434 are directed to the side of the vagus nerve VN or the cardiac branch of the vagus nerve P7.

In a state in which the position about the axis C1 of the electrode portion 438 is determined, the electrode unit 402 is placed in the superior vena cava $V_1$.

Then after the introducer or the dilator is removed, the sheath for withdrawal enters the position P1 at which the small incision is performed, and the incised portion is sutured in a state in which a portion of the sheath for withdrawal enters the vein. Since an O-ring is installed in the sheath for withdrawal, the blood is not exposed to the outside of the body.

Outside of the body of the patient P, when the inlet port 426a of the syringe piston pump 425 is connected to the connector 446 of the liquid feed tube 436 to slowly push the piston 427, the anticoagulant agent or a diluted solution thereof passes through the pipeline 436b of the liquid feed tube 436 to be discharged into the blood from the opening 436a. A discharge speed of the anticoagulant agent or the diluted solution thereof is, for example, about 0.05 to 40 ml per hour. The anticoagulant agent is continuously discharged while the electrode portion 438 is placed.

In an area of the superior vena cava $V_1$ in which the electrode portion 438 is disposed, the blood flows as shown by an arrow A1 of FIG. 67. Since a blood flow stagnates in the vicinity of the leading end attachment and the vicinity of the base end attachment, the thrombus is likely to be generated in these areas. As a liquid including an anticoagulant agent is continuously discharged from the opening 436a, stagnation of the blood flow in the vicinity of the leading end attachment and the vicinity of the attachment is prevented, the anticoagulant agent is present in the vicinity of the wire and the attachment at a high concentration, and solidification of the blood and generation of the thrombus at the wire portion 433 or the attachments 431 and 432 is suppressed.

In addition, a time for starting supply of the anticoagulant agent is not limited thereto but may be appropriately set such that supply of the anticoagulant agent is started when the electrode portion 438 is disposed in the superior vena cava $V_1$.

When an electrical stimulus is continuously applied to the vagus nerve VN for a certain period by the electrostimulation device 420, the electrostimulation device 420 and the syringe piston pump 425 are removed from the electrode unit 402.

When the electrode unit 402 is pulled back into the sheath for withdrawal, since the outer diameter of the electrode portion 438 is varied according to the inner diameter of the sheath for withdrawal, the electrode unit 402 can be removed even from a small wound to be easily extracted to the outside of the body of the patient P. There is no need for a re-operation with a large surgical invasion for removal of the electrode unit 402.

After that, an appropriate treatment such as suturing of the opening P1 is performed, and a series of procedures are completed.

As described above, according to the electrode unit 402 and the electrostimulation system 401 of the embodiment, the electrode portion 438 is disposed in the superior vena cava $V_1$ having an inner diameter smaller than the outer diameter D1 of the electrode portion 438 in the natural state. Here, in a state in which the stimulation electrode 434 side of each of the wire portions 433 abuts the inner wall of the superior vena cava $V_1$, the wire portion 433 is elastically varied to the axis C1 side and extends in the axis C1 direction. Accordingly, the stimulation electrode 434 can come in secure contact with the inner wall of the superior vena cava $V_1$.

The biphasic waveform group generated by the electrostimulation device 420 is applied between the pair of stimulation electrodes 434 via the interconnection portion 435, and the electrode unit 402 is rotated about the axis C1 to measure the heart rate of the patient P. As a result, a direction of the electrode portion 438 can be adjusted such that the stimulation electrode 434 can be directed to the vagus nerve VN side to effectively apply the electrical stimulus to the vagus nerve VN. The stimulation electrode 434 can be suppressed from coming in contact with the blood, and the voltage applied between the pair of stimulation electrodes 434 can be suppressed from being leaked to the blood side.

As the anticoagulant agent supplied from the syringe piston pump 425 is discharged into the blood from the opening 436a through the liquid feed tube 436, solidification of the blood and generation of the thrombus at the wire portion 433 or the attachments 431 and 432 can be suppressed. Since the thrombus is likely to be generated at an area at which interference with the blood flow is likely to occur, a discharge port of the anticoagulant agent can be actively and effectively formed at a place at which the attachments 431 and 432 and the wire portion 433 are collected.

As described above, as the electrical stimulus is applied to the vagus nerve VN via the tube wall of the superior vena cava $V_1$ from the pair of stimulation electrodes 434 disposed in the superior vena cava $V_1$, the electrical stimulus can be indirectly applied with no direct contact with the vagus nerve VN. Accordingly, minimally invasive treatment can be performed.

The wire portions 433 are disposed about the axis C1 at the same angular intervals. For this reason, four wire portions 433 are disposed in a four-fold rotationally symmetrical shape with respect to the axis C1. For this reason, even when the electrode portion 438 is rotated about the axis C1, variation in the shape is reduced, and manipulation performance of the electrode portion 438 is improved.

While the vein in the living body has various shapes according to the areas, since the wire portions 433 of the embodiment are disposed about the axis C1 at the same angular intervals, the wire portions 433 are deformed according to various vein shapes, and the stimulation electrode 434 securely abuts the inner wall of the vein, suppressing a leakage of electricity to the blood.

In addition, although the effect is decreased, even when the wire portions 433 are disposed about the axis C1 at irregular angles, it is needless to say that manipulation performance of the electrode portion 438 can be somewhat improved and the wire portions 433 can correspond to the shape of the vein.

Further, in the embodiment, while the four wire portions 433 are provided, it is needless to say that the electrode portion 438 can be fixed to an appropriate position in the vein as long as the number of wire portions 433 is two or more. As the number of wire portions 433 is increased, more stable manipulation performance can be realized, and fixing according to various vein shapes can be easily realized.

In recent times, in a field of treatment of heart failure, it has been known that, as an electrostimulation system of directly applying electronic intervention with respect to an autonomic nerve is used, abnormal circulation adjustment can be corrected and life prognosis of the patient can be improved.

In addition, in an acute myocardial infarction patient's condition, as vagus nerve stimulation treatment for several days after outbreak of an illness is performed using the electrostimulation system, arrhythmias generated according to reperfusion treatment and arrhythmia and heart remodeling generated after myocardial infarction can be reduced. It is already known that the vagus nerve stimulus suppresses generation of the arrhythmia according to the arrhythmia or reperfusion treatment after the myocardial infarction. The vagus nerve stimulus having an appropriate strength reduces a cardiac load via an increase in heart rate and an increase in peripheral vascular resistance to protect the myocardium by a centrifugal nerve stimulus effect and a centripetal nerve stimulus effect thereof, and reduces a myocardial infarction region (the myocardium amount necrosed by the myocardial infarction). In addition, acetylcholine discharged from a nerve ending to the heart by the centrifugal vagus nerve stimulus has an anti-inflammatory action and an anti-apoptotic effect, and directly protects the myocardial cell, and the vagus nerve stimulus suppresses the heart remodeling after the myocardial infarction and prevents progress of the heart failure via these plurality of mechanisms.

The vagus nerve stimulation can be performed at various areas along its length, and in general, vagus nerve stimulation at the cervix is performed. However, since the vagus nerve governs not only the heart but also various internal organs, the vagus nerve stimulus in an area near the center exerts an influence on many internal organs. In order to prevent generation of side effects due to stimulation of the vagus nerve governing internal organs other than a target internal organ, vagus nerve stimulation at an area nearer the target internal organ is preferable. When the vagus nerve stimulation is performed at the area nearer the heart, since it is not necessary to worry about side effects to the other internal organs, stimulation can be performed at a strength enabling accomplishment of substantial effects with respect to the heart. As the chest vagus nerve near the superior vena cava is stimulated, a recurrent laryngeal nerve stimulus generated by the cervix vagus nerve stimulus can be avoided, and side effects such as hoarseness can be prevented. Further, as only the cardiac branch of the vagus nerve near the superior vena cava is stimulated, stimulation of the vagus nerve governing the alimentary canal can be avoided, and side effects such as diarrhea, rumbling stomach, or the like can be prevented. Furthermore, a large amount of skeletal muscles are present around the vagus nerve in the cervix, and these muscles are stimulated by a leakage current upon nerve stimulation to cause symptoms such as twitching or pains. The vagus nerve near the superior vena cava is not surrounded by the skeletal muscle, and symptoms such as twitching or pains do not easily occur.

According to the electrostimulation system 401 of the embodiment, when the electrical stimulation is performed on the nervous tissue, desired nerve stimulation can be realized without large surgical invasion to the nervous tissue, which is a target. Installation of the electrode unit 402 can be realized by a general transvenous approach widely used in a catheter operation, and in order to apply an indirect electrical stimulus without direct contact with a nerve, the installation can be completed for a short time to remove the electrode unit 402 after completion of treatment, without worrying about damage to the nervous tissue upon installation of the electrode unit 402. Accordingly, the electrode unit 402 is appropriate for the case of a temporary nerve stimulation treatment or upon emergency requiring a treatment start for a short time, realizing minimally invasive treatment with respect to the patient.

Figure 68:
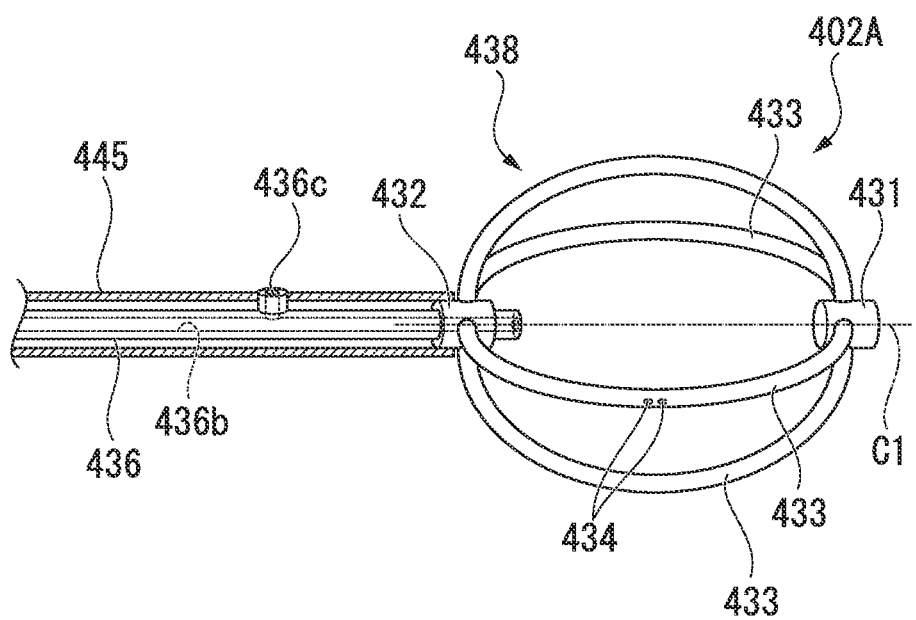
FIG. 68 is a cross-sectional view of major parts of an electrode unit according to a modification of the eleventh embodiment of the present invention.

In addition, in this embodiment, like an electrode unit 402A as shown in FIG. 68, a side opening 436c in communication with the pipeline 436b of the liquid feed tube 436 may be formed in an intermediate portion in the longitudinal direction of the liquid feed tube 436, and the side opening 436c may be exposed to the outside from the lead main body 445. A position at which the side opening 436c is formed may be disposed in the vein when the electrode unit 402A is introduced into the body.

According to the above-mentioned configuration, when the anticoagulant agent is supplied from the syringe piston pump 425, the anticoagulant agent is discharged even from the side opening 436c. Accordingly, generation of the thrombus in the wire portion 433 or the attachments 431 and 432 can be more securely suppressed.

In addition, it is needless to say that the number of side openings 436c formed in the liquid feed tube 436 is not limited thereto but may be plural.

Figure 69:
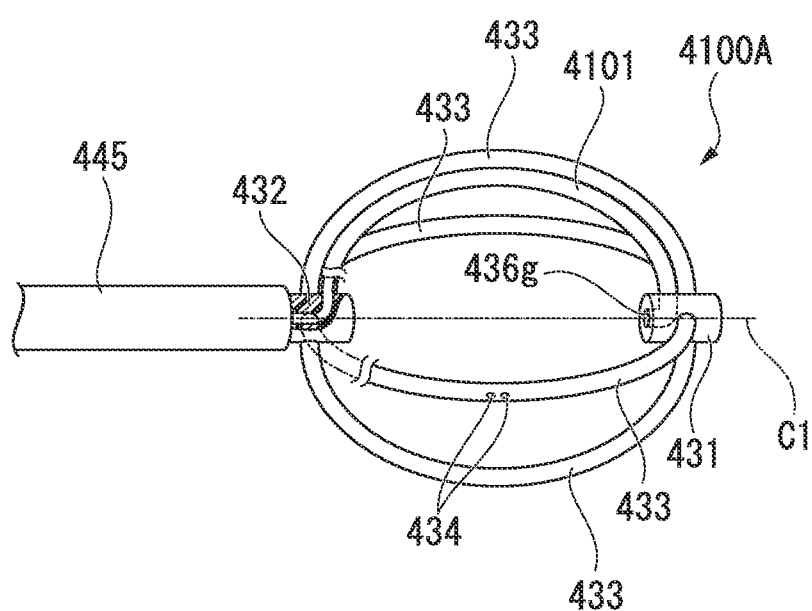
FIG. 69 is a view of the major parts of the electrode unit according to the modification of the eleventh embodiment of the present invention.

Further, in this embodiment, like an electrode unit 4100A as shown in FIG. 69, an opening 436g may be formed at the base end side (a side directed inward in the basket) of the leading end attachment 431.

The liquid feed tube 436 extends from the base end attachment 432, and is connected to the leading end attachment 431 by a liquid feed tube 4101 along the axis C of the wire portion 433 to the leading end attachment 431. A flow path inserted into the opening 436g formed in the base end side (a side directed inward in the basket) is formed in the leading end attachment 431.

In recent times, a medical antithrombotic coating agent having heparin as a base or a hydrophilic medical antithrombotic coating agent is used, and even in the embodiment, generation of the thrombus can be reduced by treating a lead surface, the wire portion 433, or surfaces of the attachments 431 and 432 with the coating agent. However, since the vicinity of the leading end attachment 431, which is most likely to interfere with the blood flow, has a structure in which the plurality of wire portions 433 are concentrated, it is difficult to completely prevent generation of the thrombus using only the medical antithrombotic coating agent. For this reason, the opening 436g configured to discharge the anticoagulant agent is formed at a surface side opposite to the blood flow of the leading end attachment 431 (a side directed inward in the basket), and the discharged anticoagulant agent stagnates in the vicinity of the leading end attachment 431 in a relatively high concentration state, more effectively preventing generation of the thrombus. In addition, since the anticoagulant agent flows along an external shape of the leading end attachment 431 by relatively increasing the discharged amount, adherence of the thrombus can also be further suppressed by the action of the flow.

Like the embodiment, when the vagus nerve near the superior vena cava or the cardiac branch of the vagus nerve is stimulated, the electrostimulation system should be placed in the superior vena cava. Here, since the superior vena cava is the vein directly connected to the heart, a large flow rate of blood intermittently flows. For this reason, different from the internal jugular vein through which a relatively small flow rate of blood continuously flows, a larger thrombus is easily formed in the superior vena cava. In this point, according to the electrostimulation system of the present invention, when placed in the superior vena cava, as the anticoagulant agent or the diluted solution thereof is discharged, formation of the thrombus can be appropriately prevented. For this reason, unlike the conventional electrostimulation system that should be placed in the internal jugular vein in which a large thrombus cannot be easily formed, the electrostimulation system according to the embodiment can be safely placed in the superior vena cava, and can more effectively apply the electrical stimulus to the vagus nerve or the cardiac branch of the vagus nerve.

(Twelfth Embodiment)

Next, while a twelfth embodiment of the present invention will be described with reference to FIGS. 70 to 74, like elements in the embodiment are designated by like reference numerals, description thereof will be omitted, and only differences will be described.

Figure 70:
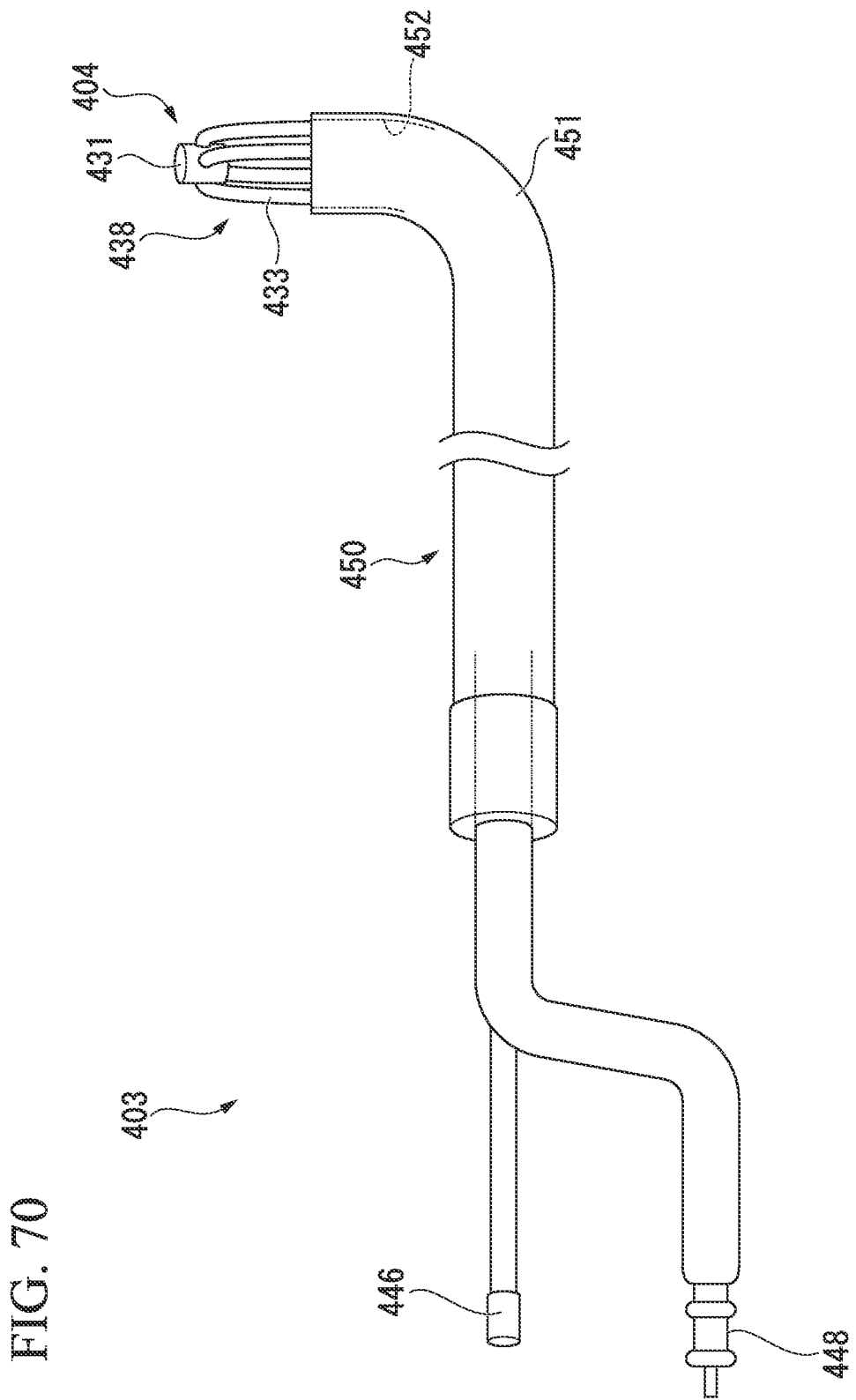
FIG. 70 is an overall view of an electrode unit according to a twelfth embodiment of the present invention.
Figure 71:
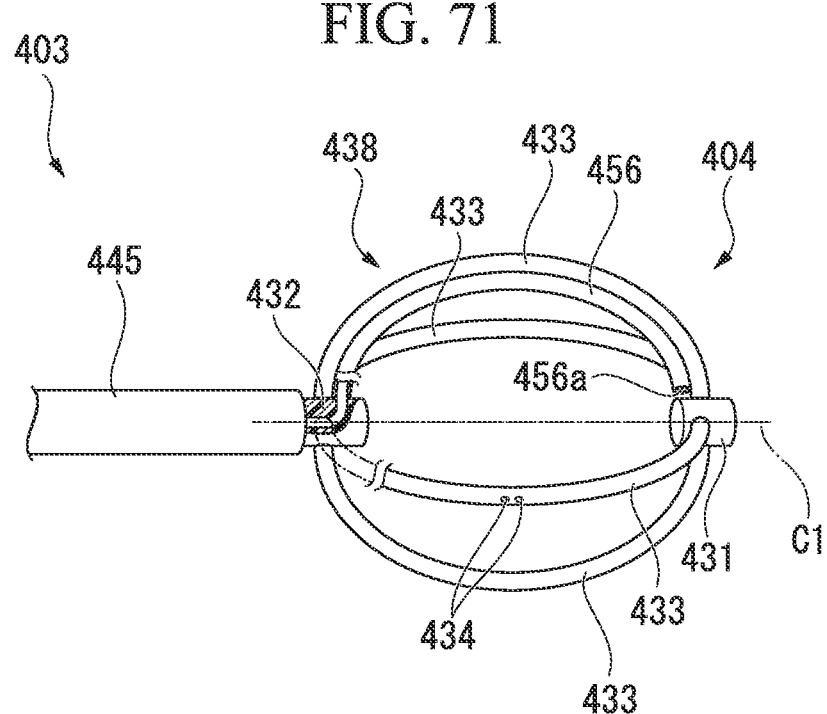
FIG. 71 is a view showing an electrode unit according to the twelfth embodiment of the present invention in a state that a guide sheath is removed and a portion of which is broken.

As shown in FIGS. 70 and 71, an electrode unit 404 used in an electrostimulation system 403 of the embodiment has a position of the opening 436a of the liquid feed tube 436 varied in the electrode unit 402 of the eleventh embodiment, and includes a guide sheath 450.

In this embodiment, a leading end side of a liquid feed tube 456 is attached to a surface of the axis C1 side of one wire portion 433. An opening 456a of a leading end side of the liquid feed tube 456 is disposed to oppose side surfaces of the leading end attachment 431.

A curved portion 451 curved in a natural state is installed at the leading end portion of the guide sheath 450. The curved portion 451 has a central angle set to about 45 to 90° to be easily directed to the internal jugular vein side (to be described later). An inner diameter of a channel 452 of the guide sheath 450 is set such that the electrode portion 438 having a reduced diameter can be inserted thereinto.

The guide sheath 450 can be formed of ETFE or the like as described above, and a thickness thereof is set such that the operator can easily tear the guide sheath 450 in a circumferential direction thereof. A groove extending in a longitudinal direction may be formed at an outer surface of the guide sheath 450 such that the guide sheath 450 is easily torn.

Figure 72:
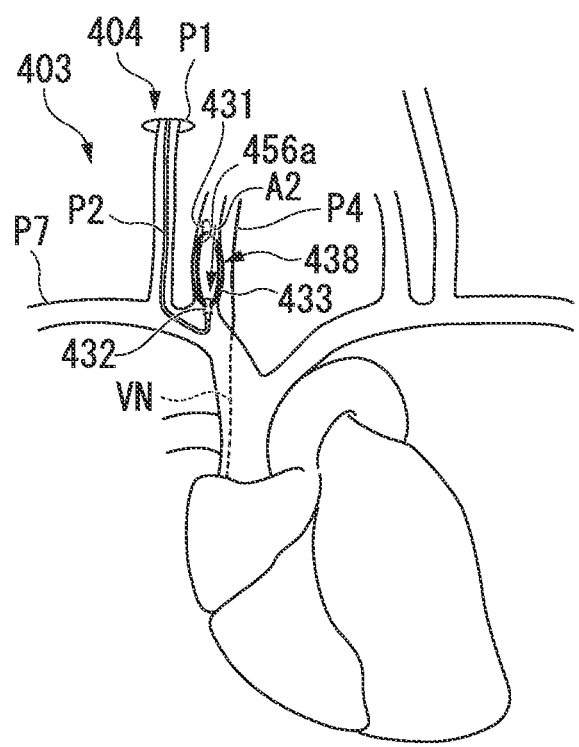
FIG. 72 is a view for explaining a state in which the electrode unit according to the twelfth embodiment of the present invention is placed in an internal jugular vein.

Next, a procedure of placing the electrode portion 438 in the internal jugular vein using the electrostimulation system 403 having the above-mentioned configuration will be described. In this case, the outer diameter D1 in the natural state of the electrode portion 438 is set to be larger than the inner diameter of the internal jugular vein. As shown in FIG. 72, the vagus nerves VN keep pace in parallel in the internal jugular vein P4.

The electrode unit 404 on which the guide sheath 450 is mounted is transvenously introduced through the right external jugular vein P2 from the opening P1. Alternatively, the opening P1 of the skin may be formed in the vicinity of the right clavicle, and may be transvenously introduced through the right subclavian vein P7. Since the curved portion 451 is installed at the leading end side of the guide sheath 450, the electrode portion 438 introduced into the right subclavian vein P7 can be directed to the internal jugular vein P4 side. The electrode unit 404 is pushed to place the electrode portion 438 in the internal jugular vein P4, and then the guide sheath 450 is torn and removed.

After that, similar to the eleventh embodiment, a direction about the axis C1 of the electrode portion 438 is adjusted. Even in the embodiment, as the pair of stimulation electrodes 434 face each other at the vagus nerve VN side to abut the vein inner wall, the heart rate of the patient P is remarkably reduced.

Continuously, when the syringe piston pump 425 is connected to the liquid feed tube 456 to push the piston 427, the anticoagulant agent is discharged into the blood from the opening 456a of the liquid feed tube 456. As shown by an arrow A2 of FIG. 72, the blood flows in the area at which the electrode portion 438 is disposed in the internal jugular vein P4. For this reason, the anticoagulant agent discharged from the opening 456a moves to the base end attachment 432 with the blood along the wire portion 433, and solidification of the blood and generation of the thrombus at the wire portion 433 or the attachments 431 and 432 are suppressed.

As described above, according to the electrode unit 404 and the electrostimulation system 403 of the embodiment, even when the electrode portion 438 is placed in the internal jugular vein P4, the electrical stimulus can be indirectly applied with no direct contact with the vagus nerve VN.

As the guide sheath 450 is included in the electrode unit 404, the electrode portion 438 introduced into the right subclavian vein P7 can be easily directed to the internal jugular vein P4 side, and the procedure can be easily performed.

In addition, it is needless to say that generation of the thrombus can be more effectively suppressed by further forming an opening near the base end attachment 432 to discharge the anticoagulant agent.

Figure 73:
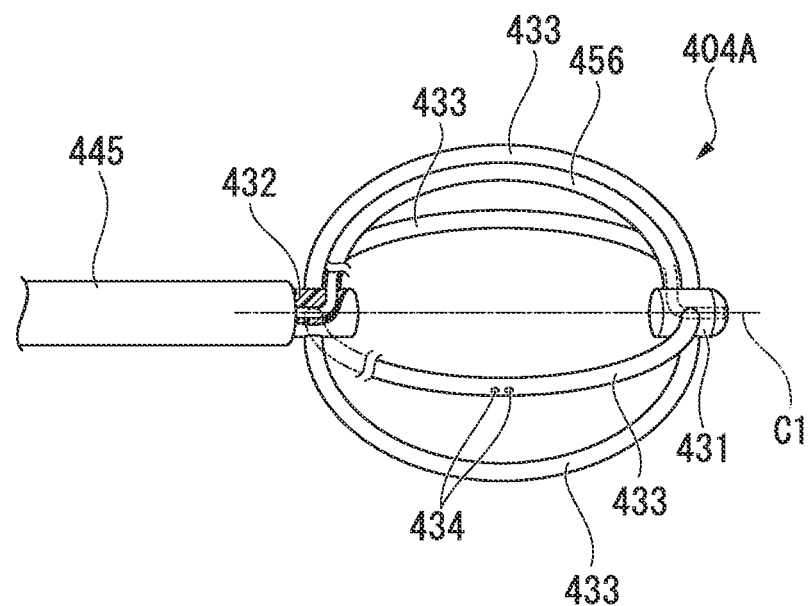
FIG. 73 is a side view of major parts of an electrode unit according to a modification of the twelfth embodiment of the present invention.
Figure 74:
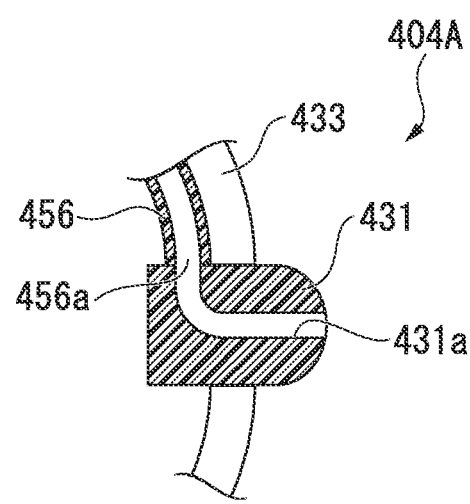
FIG. 74 is a cross-sectional view of major parts of FIG. 72.

Further, in this embodiment, like the electrode unit 404A as shown in FIGS. 73 and 74, an opening portion 431a opened at the leading end side is formed in the leading end attachment 431, and the opening 456a of the liquid feed tube 456 may be configured to be in communication with the opening portion 431a.

As the electrode unit 404A is configured as described above, when the electrode unit 404A is placed in the internal jugular vein P4, the anticoagulant agent can be discharged from the opening portion 431a. Accordingly, the thrombus generated at a connecting portion between the leading end attachment 431 and the wire portion 433 can also be effectively reduced.

In addition, the opening configured to discharge the anticoagulant agent is not limited thereto but may have, for example, the opening portion configured to open the base end attachment 432 side.

While also described in the eleventh embodiment, a place at which the thrombus is easily generated is positioned inside the attachment near the heart (downstream of the blood flow).

Here, since structure members are concentrated, the blood flow is delayed to easily generate the thrombus. While formation of the thrombus is related to the blood flow, a contact with a device, and an element of the blood, generation of the thrombus can be prevented by preventing stagnation of the blood through formation of an active flow in an area at which the thrombus is easily generated (improvement of the blood flow) or administering an anticoagulant to the area at which the thrombus is easily generated at a high concentration (improvement of the blood elements).

Accordingly, similar to the configuration shown in FIG. 59, as the liquid including the anticoagulant agent is continuously discharged from the opening 436a formed at the base end attachment 432 side, a flow prevented by stagnation of the blood flow is formed in the vicinity of the base end attachment, and the anticoagulant agent acts at a high concentration.

As described above, according to the blood flow of the vein in which the electrode portion is installed, as the opening configured to actively discharge the anticoagulant agent is formed at the area at which the thrombus is easily generated, generation of the thrombus can be effectively suppressed.

(Thirteenth Embodiment)

Next, while a thirteenth embodiment of the present invention will be described with reference to FIGS. 75 to 78, like elements in the embodiment are designated by like reference numerals, description thereof will be omitted, and only differences will be described.

Figure 75:
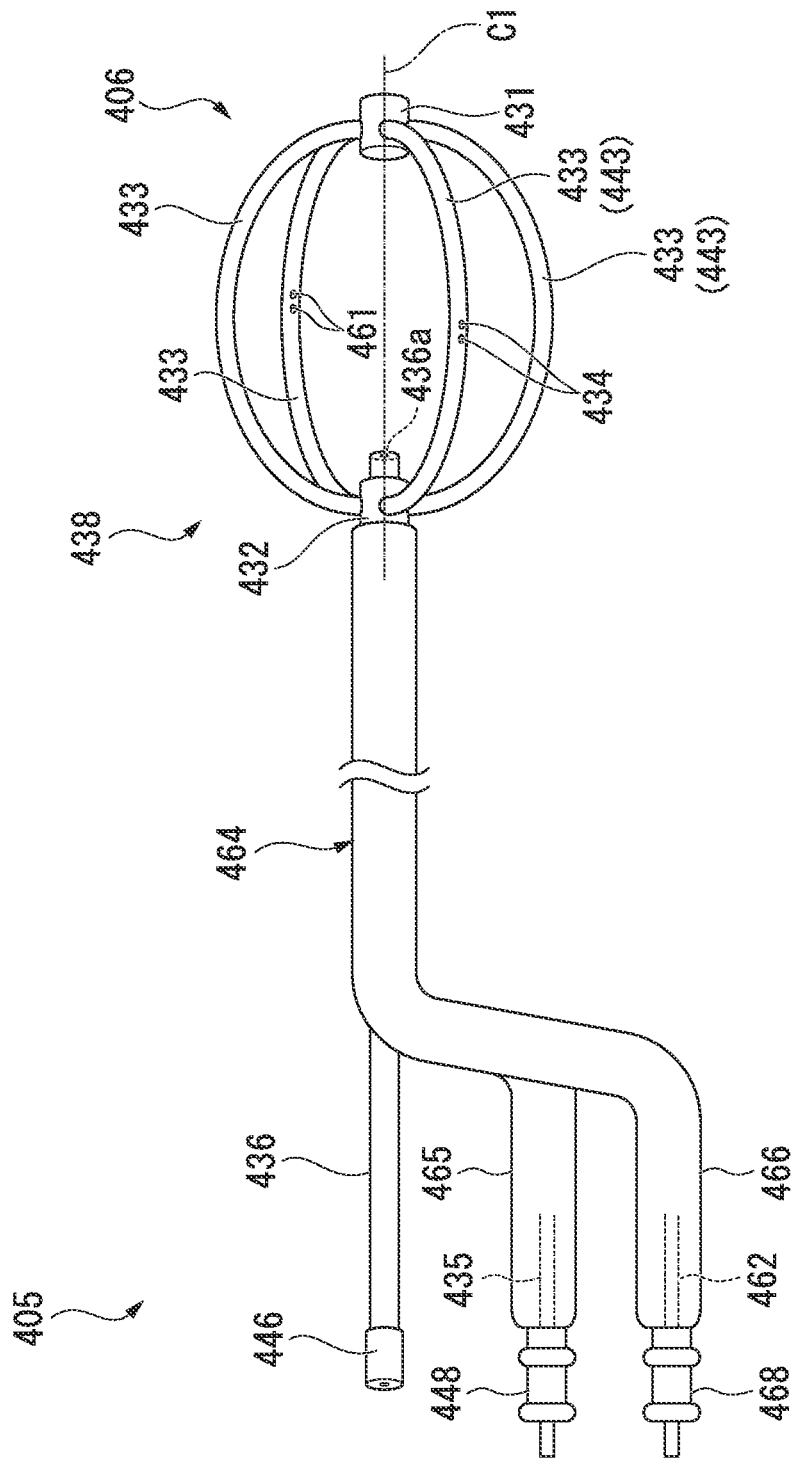
FIG. 75 is an overall view of an electrode unit according to a thirteenth embodiment of the present invention.

As shown in FIG. 75, an electrode unit 406 used in an electrostimulation system 405 of the embodiment includes, in addition to the components of the electrode unit 402 of the eleventh embodiment, a pair of measurement electrodes 461 installed at the wire portion 433 different from the wire portion 433 at which the pair of stimulation electrodes 434 are installed, and a second interconnection portion 462 having a leading end portion electrically connected to the pair of measurement electrodes 461.

Figure 76:
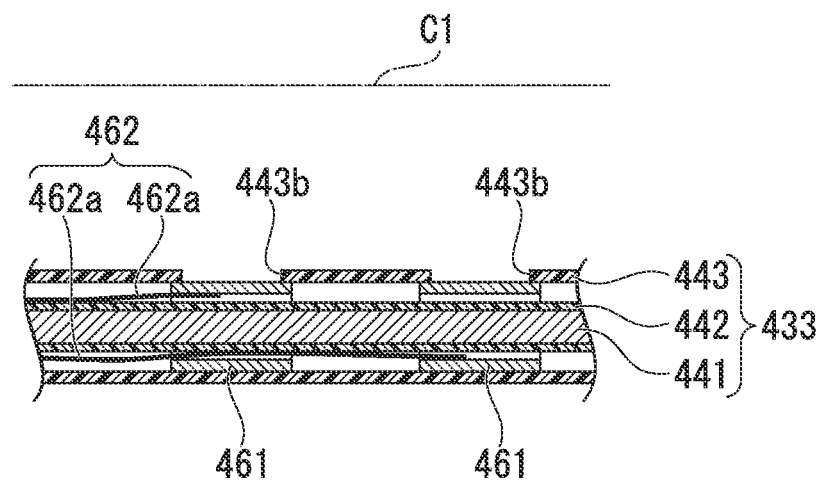
FIG. 76 is a cross-sectional view of a wire portion of the electrode unit according to the thirteenth embodiment of the present invention.
Figure 77:
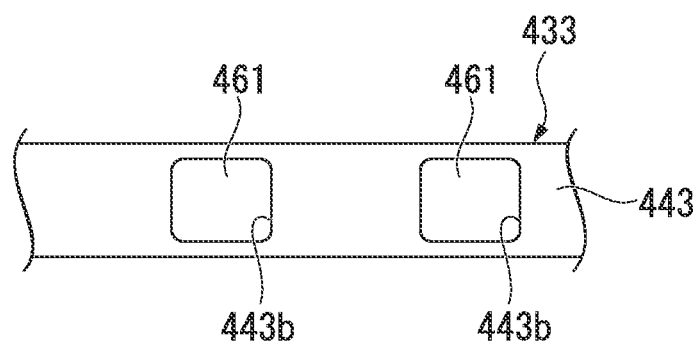
FIG. 77 is a side view of the wire portion of the electrode unit according to the thirteenth embodiment of the present invention.

As shown in FIGS. 76 and 77, in the outer capsule 443, a pair of through holes 443b are formed in parallel in the axis C1 direction at the axis C1 side of the intermediate portion in the axis C1 direction at an interval of 5 to 10 mm. The through holes 443b have a substantially rectangular shape, which is long in the axis C1 direction, when seen from a side view. The through hole 443b has, for example, a long side of 1.8 mm and a short side of 0.8 mm, which is larger than the through hole 443a.

As shown in FIG. 76, the measurement electrode 461 has a cylindrical shape and is disposed to be shifted in the axis C1 direction from the stimulation electrode 434. The measurement electrode 461 covers the through hole 443b and is exposed to the outside. An electrical interconnection 462a constituting the second interconnection portion 462 is electrically connected to the inner circumferential surface of the measurement electrode 461. Since the measurement electrode 461 and the second interconnection portion 462 have the same configurations as the stimulation electrode 434 and the interconnection portion 435, description thereof will be omitted.

As shown in FIG. 75, a lead main body 464 is branched into a first branch portion 465 and a second branch portion 466 in the base end side. The above-mentioned connector 448 is installed at the base end portion of the first branch portion 465, and the base end portion of the interconnection portion 435 is electrically connected to the connector 448. A connector 468 having the same shape as the connector 448 is installed at the base end portion of the second branch portion 466, and the base end portion of the second interconnection portion 462 is electrically connected to the connector 468. That is, in the embodiment, the electrode unit 406 is branched into three, i.e., the liquid feed tube 436, the first branch portion 465 and the second branch portion 466 in the base end side. The first branch portion 465 becomes an electrical stimulation lead, and the second branch portion 466 becomes a sensing lead.

While not shown, the electrostimulation device of the embodiment is detachable from both of the connectors 448 and 468. The electrostimulation device of the embodiment includes, in addition to the respective components of the electrostimulation device 420, a heart rate measurement unit configured to measure a heart rate using the pair of measurement electrodes 461, and a control unit configured to control output of the electrical stimulus supply unit based on the measured heart rate.

As the heart rate measurement unit detects a potential difference between the pair of measurement electrodes 461 upon contact with the blood, variation in potential varied by electrical activity of the heart, i.e., an electrocardiographic signal, can be obtained. In addition, the heart rate measurement unit can measure a heart rate from a time interval of a time at which, for example, a magnitude or a variation rate of a potential of the electrocardiographic signal becomes larger than a predetermined threshold, based on a waveform of the obtained electrocardiographic signal.

The control unit decreases energy of the electrical stimulus output from the electrical stimulus supply unit or stops supply thereof when the heart is in a bradycardiac state the heart rate is less than a certain rate. Accordingly, a cardiac heat rate drop is suppressed, and the heart rate is increased. In addition, when the heart is in a tachycardiac state in which the heart rate is raised, energy of an electrical stimulus output from the electrical stimulus supply unit is increased. Accordingly, the vagus nerve passing through the vicinity of the vein is stimulated to decrease the heart rate.

When the electrode portion 438 of the electrode unit 406 of the embodiment having the above-mentioned configuration is placed in the vein such as the superior vena cava $V_1$ or the internal jugular vein P4, the pair of stimulation electrodes 434 contact the inner wall of the vein and at the same time the pair of measurement electrodes 461 abut the blood. Accordingly, the pair of measurement electrodes 461 obtain cardiac activity, in other words, an electrocardiographic signal. The electrostimulation device 420 connected to the pair of measurement electrodes 461 measures the heart rate of the patient P from the electrocardiographic signal, and adjusts the energy of the electrical stimulus applied to the vagus nerve VN such that the patient P has a predetermined heart rate.

As described above, according to the electrode unit 406 and the electrostimulation system 405 of the embodiment, the same effect as the electrode unit 402 and the electrostimulation system 401 of the eleventh embodiment can be accomplished.

Further, as the pair of measurement electrodes 461 and the second interconnection portion 462 are provided, the heart rate of the patient P can be measured from a potential difference between the pair of measurement electrodes 461, and the energy of the electrical stimulus applied to the vagus nerve VN can be adjusted such that the patient P has a predetermined heart rate.

The electrostimulation device can observe that the patient P has extreme bradycardia, emit an alarm upon abnormality, and automatically vary electrical stimulus conditions to always maintain a state in which the heart rate is decreased by a certain ratio. In addition, according to activities of the patient P, even when the heart rate is varied, a predetermined amount of heartbeat drop effect, i.e., a reduction effect of a cardiac load, can always be maintained.

In comparison with the conventional electrocardiographic signal measured by installing an electrocardiogram pad on a body surface of the patient P, a heart electric waveform obtained via the blood of the present invention cannot be easily affected by noises due to the activities and can stably measure the heart rate.

In addition, electrical stimulus conditions varied by the electrostimulation device may include a magnitude, a frequency, a pulse width of an electrical stimulus pulse voltage or current, a stimulus termination time, a stimulus start time, a stimulus continuation time, an electrical stimulus stop, or the like.

Further, in the embodiment, while the stimulation electrode 434 and the measurement electrode 461 are formed at the different wire portions 433, the stimulation electrode 434 and the measurement electrode 461 may be formed at one wire portion 433. Here, the measurement electrodes 461 are formed at the leading end attachment 431 side and the base end attachment 432 side to sandwich the pair of stimulation electrodes 434, and an increase in an electrode interval between the measurement electrodes 461 enables acquisition of a good electrocardiogram waveform.

Figure 78:
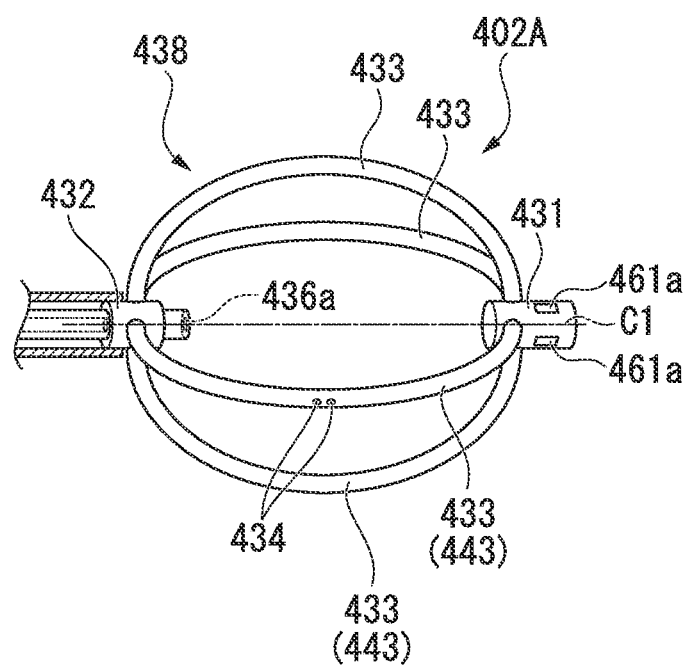
FIG. 78 is a view showing major parts of an electrostimulation system according to the thirteenth embodiment of the present invention.

FIG. 78 shows an example of the pair of measurement electrodes 461a having different configurations. The measurement electrode 461a has two electrodes having an arcuate shape and formed of platinum iridium, which are installed at the outer circumferential side surfaces of the leading end attachment 431. Even in the embodiment, the measurement electrode 461a can contact the blood, and can measure the heart rate of the patient P from the potential difference between the measurement electrodes 461a. Further, as a direction in which the respective electrodes of the measurement electrodes 461a are bound coincides with a direction (a left/right horizontal direction of the superior vena cava) coinciding with the direction from the right ventricle to the left ventricle direction of the heart, a behavior of the heart can be easily detected as a large heart electric waveform.

(Fourteenth Embodiment)

Next, while a fourteenth embodiment of the present invention will be described with reference to FIGS. 79 and 80, like elements in the embodiment are designated by like reference numerals, description thereof will be omitted, and only differences will be described.

Figure 79:
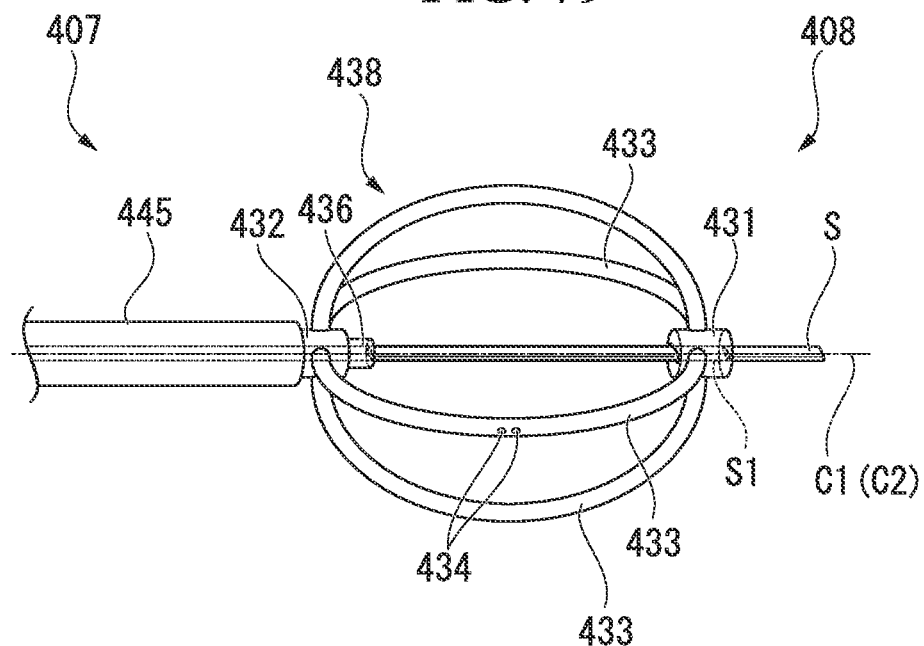
FIG. 79 is a side view of major parts of an electrode unit according to a fourteenth embodiment of the present invention.
Figure 80:
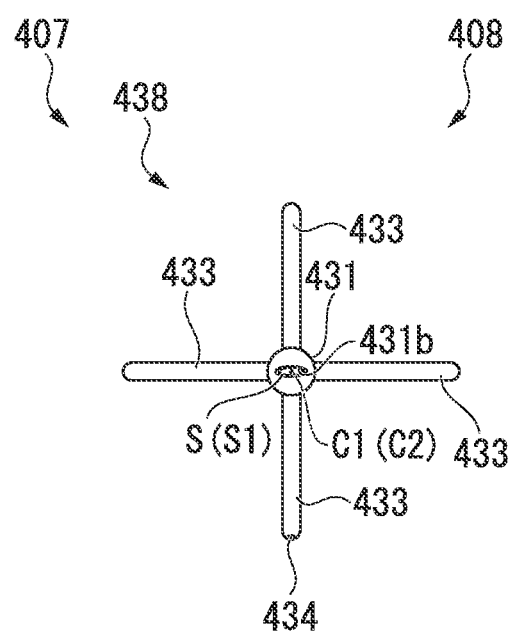
FIG. 80 is a front view of the electrode unit according to the fourteenth embodiment of the present invention.

As shown in FIGS. 79 and 80, in an electrode unit 408 used in an electrostimulation system 407 of the embodiment, a leading end through-hole 431b passing on the axis C1 is formed at the leading end attachment 431 of the electrode unit 402 of the eleventh embodiment.

A cross section of the inner surface of the leading end through-hole 431b perpendicular to the axis C1 has an oval shape.

In the electrostimulation system 407 of the embodiment, a stilet (a shaft-shaped member) S is inserted into the pipeline 436b of the liquid feed tube 436 and the leading end through-hole 431b and used. When the stilet S is inserted into the leading end through-hole 431b, the stilet S is used to sufficiently protrude in front of the leading end attachment 431. A cross section of an outer surface of a section S1 inserted into the leading end through-hole 431b in the stilet S has an oval shape slightly smaller than the cross section of the above-mentioned leading end through-hole 431b. The stilet S has strength such that certain flexibility can be provided and a torque about a central axis thereof can be transmitted. A member having substantially a hemispherical shape and no probability of damage to the vein inner wall may be used as a leading end portion of the stilet S.

A procedure using the electrostimulation system 407 having the above-mentioned configuration is performed as follows.

That is, outside of the body of the patient P, the stilet S is inserted into the pipeline 436b of the liquid feed tube 436 and the leading end through-hole 431b of the leading end attachment 431. Then, the electrode portion 438 is placed in a target vein. Since the stilet S has flexibility, in the vein, the stilet S can be easily bent with the electrode unit 408. In addition, when the electrode portion 438 is placed, as the electrode portion 438 extends in the axis C1 direction, the leading end attachment 431 moves forward with respect to the stilet S. However, since the stilet S sufficiently protrudes in front of the leading end attachment 431, the leading end attachment 431 is not dropped from the stilet S.

After the electrode portion 438 is schematically disposed, the operator grips both of the lead main body 445 and the stilet S to pivot them about a central axis C2 of the stilet S. Then, as the section S1 of the stilet S is engaged with the inner surface of the leading end through-hole 431b, the electrode portion 438 is pivoted about the axis C1 with the stilet S.

In addition, after the direction of the electrode portion 438 is adjusted, the stilet S is extracted from the liquid feed tube 436, and a flow path configured to supply the anticoagulant agent is secured.

As described above, according to the electrode unit 408 and the electrostimulation system 407 of the embodiment, the same effect as the embodiment can be accomplished.

Further, a rotational force acted by the operator can be effectively transmitted to the electrode portion 438 via the stilet S, and a direction about the axis C1 of the electrode portion 438 can be adjusted for a short time.

Furthermore, in this embodiment, a cross section of the inner surface of the leading end through-hole 431b perpendicular to the axis C1 has an oval shape. However, the cross section is not limited to the oval shape but may be a convex polygonal shape such as a rectangular shape as long as the polygonal shape is not a circular shape. In this case, a cross section of the outer surface of the section S1 of the stilet S has a shape slightly smaller than the cross section of the inner surface of the leading end through-hole 31b to be engaged with the inner surface of the leading end through-hole 431b.

As described above, while the eleventh embodiment to the fourteenth embodiment of the present invention have been described in detail with reference to the drawings, a specific configuration is not limited to the embodiments but includes modifications of components within the scope without departing from the gist of the present invention. Further, it is needless to say that the respective components shown in the embodiments can be appropriately assembled and used.

Figure 81:
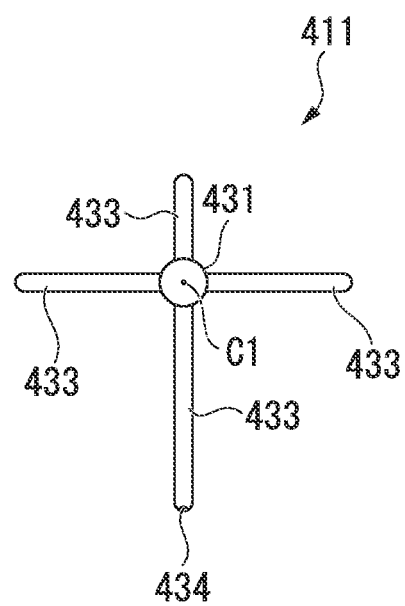
FIG. 81 is a front view of an electrostimulation system according to a modification of an embodiment of the present invention.

For example, like an electrode unit 411 shown in FIG. 81, an extent to which some wire portions 433 of four wire portions 433 are bent to be spaced apart from the axis C1 may be smaller than that of the other wire portions 433.

Figure 82:
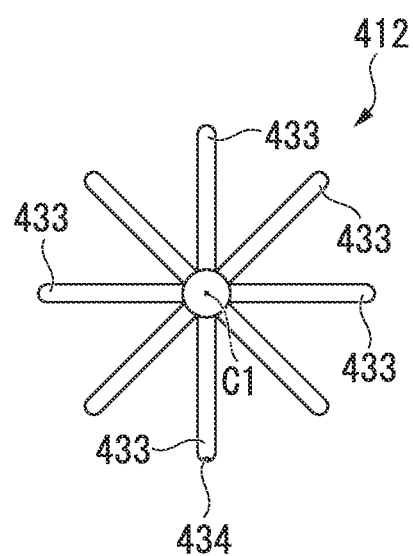
FIG. 82 is a front view of the electrostimulation system according to the modification of the embodiment of the present invention.

In addition, as shown in FIG. 82, the number of wire portions 433 included in an electrode unit 412 is not limited but may be plural. As the number of wire portions 433 is increased, the electrode unit 412 can be stably placed in the vein. When placed in the vein having a large inner diameter, the number of wire portions 433 may be increased, and when placed in the vein having a small inner diameter, the number of wire portions 433 may be reduced.

The wire portions 433 may not be disposed about the axis C1 at the same angular intervals, and the wire portions 433 may be disposed to support the tube wall of the vein about the axis C1.

Figure 83:
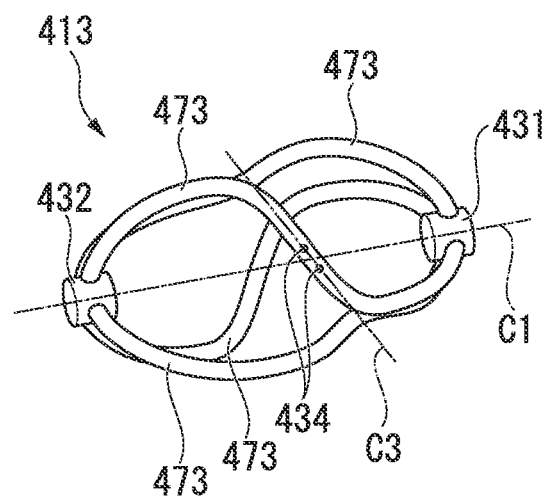
FIG. 83 is a perspective view of major parts of the electrostimulation system according to the modification of the embodiment of the present invention.
Figure 84:
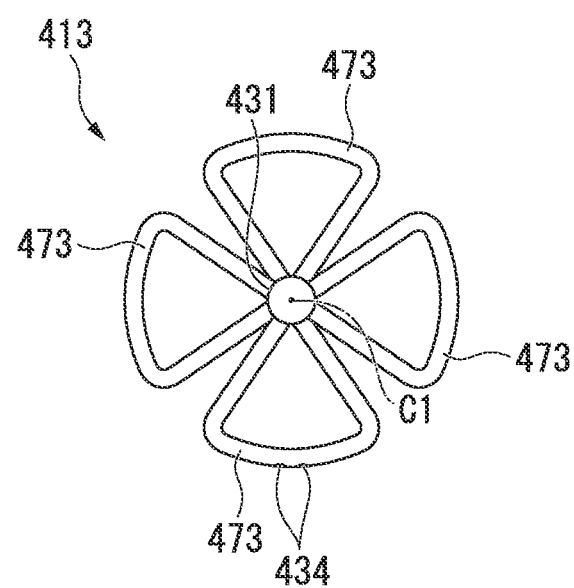
FIG. 84 is a front view of the same major parts.

Like an electrode unit 413 shown in FIGS. 83 and 84, the four wire portions 473 may have an S shape and an arcuate shape when seen from a front view. In this case, when seen to oppose the pair of stimulation electrodes 434 in a direction perpendicular to the axis C1, the pair of stimulation electrodes 434 are disposed such that a reference line C3 passing through the pair of stimulation electrodes 434 crosses the axis C1.

When the electrode unit 413 having the above-mentioned configuration is placed in the vein, while the reference line C3 is disposed to be inclined with respect to the axis C1, i.e., the longitudinal direction of the vein, it is effective when the vagus nerve VN is inclined and parallelly keeps pace with respect to the vein.

In addition, even both when the vagus nerves VN keeps pace in parallel with respect to the vein and when it inclinedly keeps pace with respect to the vein, the pair of stimulation electrodes 434 can be disposed to flank the vagus nerve VN, and the vagus nerve VN can be securely stimulated by the pair of stimulation electrodes 434.

Further, when seen in a direction perpendicular to the axis C1, it is needless to say that a concept in which the reference line C3 passing through the pair of stimulation electrodes 434 crosses the axis C1 is not limited to the embodiment, but may be realized in various shapes by a crossing angle of the reference line C3 or a shape of the wire portion.

Furthermore, it is needless to say that the above-mentioned measurement electrode 461 may be formed at the axis C1 side of the wire portion 473 at which the stimulation electrode 434 is not formed.

Figure 85:
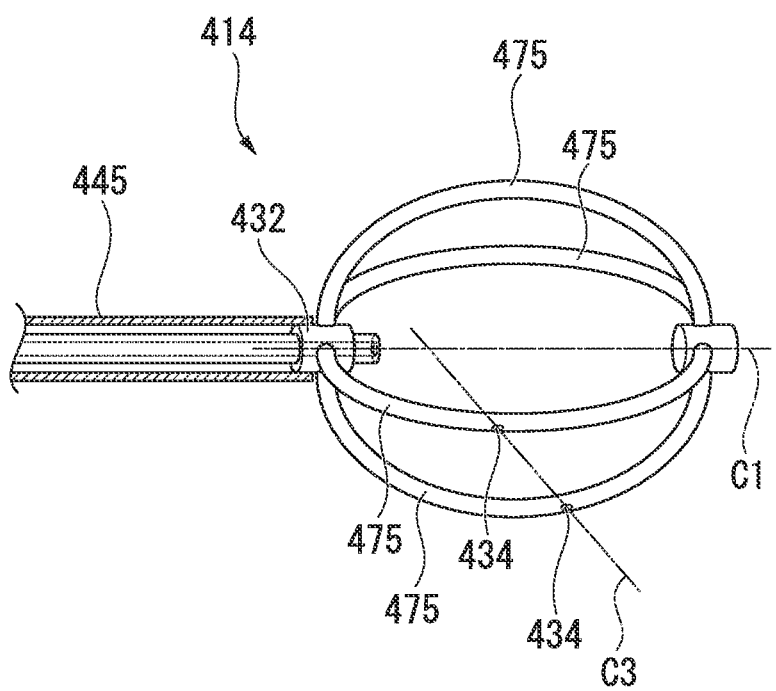
FIG. 85 is a perspective view of the major parts of the electrostimulation system according to the modification of the embodiment of the present invention.

In addition, in an electrode unit 414 shown in FIG. 85, the pair of stimulation electrodes 434 are formed at two of the four wire portions 475 one by one. The reference line C3 passing through the pair of stimulation electrodes 434 is disposed to cross the axis C1 as described above, and similarly, is effective when the vagus nerve VN inclinedly keeps pace with respect to the vein.

Further, in the eleventh embodiment to the fourteenth embodiment, the pair of stimulation electrodes 434 or the pair of measurement electrodes 461 may be plurally installed at two or more wire portions 433. Here, as the IS1 type of connectors corresponding to the number of pairs of the stimulation electrodes 434 and the measurement electrodes 461 are installed at the base end portion of the lead main body and the connector connected to the electrostimulation device is selected, the stimulation electrode 434 at an appropriate position or the measurement electrode 461 at which the heart electric waveform can be largely detected is appropriately selected, and more effective nerve stimulation can be started for a shorter time.

In addition, coating for preventing solidification of the blood is of course effectively performed on outer surfaces of the attachments 431 and 432, the wire portion, the lead main body, or the like.

The electrostimulation system introduces the electrode unit from the opening P1 in the vicinity of the neck. However, the electrode unit may be introduced into the body from the opening or the like formed under the vicinity of the clavicle.

While preferred embodiments of the invention have been described and illustrated above, it should be understood that these are exemplary of the invention and are not to be considered as limiting. Additions, omissions, substitutions, and other modifications can be made within the scope without departing from the gist or scope of the present invention.

Accordingly, the invention is not to be considered as being limited by the foregoing description, and is only limited by the scope of the appended claims.

What is claimed is:

1. A method of placing an electrostimulation system comprising:
   an electrode unit insertion step of inserting an electrode unit into a vein, wherein the electrode unit includes:
      a lead main body having a longitudinal axis, the lead main body including an electrostimulation lead and a rotary member; and
      an electrode portion provided at a distal end of the lead main body and including a stimulation electrode provided so as to be exposed at a predetermined part of the electrode portion in a direction around the longitudinal axis,
      wherein the rotary member includes an engagement portion which is detachably engaged with the electrode portion, and an insertion slot portion into which the electrostimulation lead and the stimulation electrode are inserted;
   an electrode unit disposition step of disposing the electrode unit in a superior vena cava in vicinity of a vagus nerve;
   a thrombus formation prevention step of discharging an anticoagulant agent into the superior vena cava such that the anticoagulant agent moves along the electrode portion;
   an electrode unit biasing step of biasing the stimulation electrode in a direction of the vagus nerve;
   subsequent to the electrode unit biasing step, an adjustment step of adjusting a position of the biased stimulation electrode in the direction around the longitudinal axis such that the stimulation electrode is directed to the vagus nerve by rotating the rotary member around the longitudinal axis while the engagement portion is engaged with the electrode portion; and
   subsequent to the adjustment step, an electrical stimulation step of applying electrical stimulus energy to the vagus nerve.

2. The method of placing the electrostimulation system according to claim 1, wherein the thrombus formation prevention step is an anticoagulant agent discharge step of discharging the anticoagulant agent from a liquid feed tube opening formed in the electrode unit.

3. The method of placing the electrostimulation system according to claim 1, wherein the adjustment step further includes:
   applying a voltage to the stimulation electrode;
   measuring a heart rate of a subject; and
   adjusting the position of the stimulation electrode in the direction around the longitudinal axis within the vein such that the heart rate is decreased as much as possible by rotating the lead main body around the longitudinal axis.

4. The method of placing the electrostimulation system according to claim 1, wherein the anticoagulant agent is discharged into the superior vena cava such that the anticoagulant agent flows to a downstream side from an upstream side of the electrode portion.

* * * * *